US010577604B2

(12) United States Patent
Bennett et al.

(10) Patent No.: US 10,577,604 B2
(45) Date of Patent: Mar. 3, 2020

(54) METHODS FOR MONITORING C9ORF72 EXPRESSION

(71) Applicants: Ionis Pharmaceuticals Inc., Carlsbad, CA (US); The Johns Hopkins University, Baltimore, MD (US)

(72) Inventors: C. Frank Bennett, Carlsbad, CA (US); Susan M. Freier, San Diego, CA (US); Jeffrey D. Rothstein, Catonsville, MD (US); Christopher Donnelly, Newtown Square, PA (US); Rita G. Sattler, Phoenix, AZ (US)

(73) Assignees: Ionis Pharmaceuticals, Inc., Carlsbad, CA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/436,039

(22) PCT Filed: Oct. 15, 2013

(86) PCT No.: PCT/US2013/065131
§ 371 (c)(1),
(2) Date: Apr. 15, 2015

(87) PCT Pub. No.: WO2014/062736
PCT Pub. Date: Apr. 24, 2014

(65) Prior Publication Data
US 2016/0024496 A1    Jan. 28, 2016

Related U.S. Application Data

(60) Provisional application No. 61/714,142, filed on Oct. 15, 2012.

(51) Int. Cl.
*C12N 15/113* (2010.01)
*C12Q 1/6883* (2018.01)
*A61K 31/7088* (2006.01)

(52) U.S. Cl.
CPC ........ *C12N 15/113* (2013.01); *A61K 31/7088* (2013.01); *C12Q 1/6883* (2013.01); *C12N 2310/11* (2013.01); *C12N 2310/111* (2013.01); *C12N 2310/113* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,801,154 A | 9/1998 | Baracchini et al. | |
| 5,998,148 A | 12/1999 | Bennett et al. | |
| 6,268,490 B1 | 7/2001 | Imanishi et al. | |
| 6,525,191 B1 | 2/2003 | Ramasamy | |
| 6,582,908 B2 | 6/2003 | Fodor et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,696,345 B2 | 4/2010 | Allerson et al. | |
| 7,759,478 B1 | 7/2010 | Bentwich et al. | |
| 8,501,805 B2 | 8/2013 | Seth et al. | |
| 8,530,640 B2 | 9/2013 | Seth et al. | |
| 8,546,556 B2 | 10/2013 | Seth et al. | |
| 9,012,421 B2 | 4/2015 | Migawa et al. | |
| 9,605,263 B2 | 3/2017 | Rigo | |
| 9,896,729 B2 | 2/2018 | Pickering-Brown et al. | |
| 9,963,699 B2 | 5/2018 | Bennett et al. | |
| 10,138,482 B2 | 11/2018 | Rigo | |
| 10,221,414 B2 | 3/2019 | Freier et al. | |
| 2001/0053519 A1 | 12/2001 | Fodor et al. | |
| 2003/0228597 A1 | 12/2003 | Cowsert et al. | |
| 2004/0038274 A1 | 2/2004 | Cook et al. | |
| 2004/0171570 A1 | 9/2004 | Allerson et al. | |
| 2004/0181048 A1 | 9/2004 | Wang | |
| 2005/0130923 A1 | 6/2005 | Bhat et al. | |
| 2006/0003322 A1 | 1/2006 | Bentwich et al. | |
| 2007/0031844 A1 | 2/2007 | Khvorova et al. | |
| 2008/0039618 A1 | 2/2008 | Allerson et al. | |
| 2009/0012281 A1 | 1/2009 | Swayze et al. | |
| 2010/0216864 A1 | 8/2010 | Staarup et al. | |
| 2012/0149757 A1 | 6/2012 | Krainer et al. | |
| 2012/0214865 A1 | 8/2012 | Bennett et al. | |
| 2013/0035366 A1 | 2/2013 | Swayze et al. | |
| 2014/0255936 A1 | 9/2014 | Rademakers | |
| 2014/0303238 A1* | 10/2014 | Linsley ................. | C07H 21/04 514/44 A |
| 2015/0148404 A1* | 5/2015 | de Visser ............. | C12N 15/113 514/44 A |
| 2015/0251655 A1 | 9/2015 | Freier et al. | |
| 2015/0259679 A1 | 9/2015 | Bennett et al. | |
| 2015/0267197 A1 | 9/2015 | Bennett et al. | |
| 2016/0108396 A1 | 4/2016 | Jensen et al. | |
| 2016/0251655 A1 | 9/2016 | Freier et al. | |
| 2016/0304871 A1 | 10/2016 | Rigo | |
| 2017/0349897 A1 | 12/2017 | Rigo | |
| 2018/0318330 A1 | 11/2018 | Prakash et al. | |
| 2019/0142856 A1 | 5/2019 | Bennett et al. | |
| 2019/0264204 A1 | 8/2019 | Rigo | |

FOREIGN PATENT DOCUMENTS

| | | |
|---|---|---|
| EP | 1752536 | 2/2007 |
| WO | WO 2016/024205 | 2/1916 |

(Continued)

OTHER PUBLICATIONS

Kurreck (Eur. J. Biochem. vol. 270:1628-1644, 2003).*

(Continued)

*Primary Examiner* — Sean McGarry
(74) *Attorney, Agent, or Firm* — McNeill Baur PLLC

(57) ABSTRACT

Disclosed herein are methods for monitoring expression of C9ORF72 mRNA and protein in an animal with C9ORF72 specific inhibitors. Such C9ORF72 specific inhibitors include antisense compounds.

19 Claims, 9 Drawing Sheets

Specification includes a Sequence Listing.

(56) References Cited

FOREIGN PATENT DOCUMENTS

| WO | WO 2016/050822 | 4/1916 |
|---|---|---|
| WO | WO 2016/060919 | 4/1916 |
| WO | WO 2018/064600 | 4/1918 |
| WO | WO 1996/014329 | 5/1996 |
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/113016 | 12/2005 |
| WO | WO 2005/121368 | 12/2005 |
| WO | WO 2007/056113 | 5/2007 |
| WO | WO 2007/089584 | 8/2007 |
| WO | WO 2007/131237 | 11/2007 |
| WO | WO 2007/134181 | 11/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/007855 | 1/2009 |
| WO | WO 2009/049166 | 4/2009 |
| WO | WO 2009/060124 | 5/2009 |
| WO | WO 2010/148013 | 12/2010 |
| WO | WO 2011/005793 | 1/2011 |
| WO | WO 2011/135396 | 11/2011 |
| WO | WO 2012/005898 | 1/2012 |
| WO | WO 2012/012443 | 1/2012 |
| WO | WO 2012/012467 | 1/2012 |
| WO | WO 2012/087983 | 6/2012 |
| WO | WO 2012/092367 | 7/2012 |
| WO | WO 2012/135736 | 10/2012 |
| WO | WO 2013/030588 | 3/2013 |
| WO | WO 2013/036833 | 3/2013 |
| WO | WO 2013/075079 | 5/2013 |
| WO | WO 2013/082548 | 6/2013 |
| WO | WO 2013/086207 | 6/2013 |
| WO | WO 2013/173608 | 11/2013 |
| WO | WO 2014/062686 | 4/2014 |
| WO | WO 2014/062691 | 4/2014 |
| WO | WO 2014/062736 | 4/2014 |
| WO | WO 2014/114660 | 7/2014 |
| WO | WO 2015/054676 | 4/2015 |
| WO | WO 2016/168592 | 10/2016 |
| WO | WO 2017/079291 | 5/2017 |
| WO | WO 2017/180835 | 10/2017 |

OTHER PUBLICATIONS

"The ALS Association and the Packard Center Partner to Develop Animal Model Systems for Most Common Cause of Familial ALS", http://www.alsa.org/news/archive/new-animal-model-systems.html (printed Oct. 23, 2015).
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals " Chimia. (1996) 50(4):168-176.
Altmann et al., "Second-generation antisense oligonucleotides: structure-activity relationships and the design of improved signal-transduction inhibitors" Biochem. Soc. Trans. (1996) 24:630-637.
Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Bieniek et al., "Tau pathology in frontotemporal lobar degeneration with C9ORF72 hexanucleotide repeat expansion" (2013) 125(2):289-302.
Boxer et al. "Clinical, neuroimaging and neuropathological features of a new chromosome 9p-linked FTD-ALS family" J. Neurol. Neurosurg. Psychiatry (2011) 82:196-203.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Chio et al., "Prevalence of SOD1 mutations in the Italian ALS population" Neurology (2008) 70:533-537.
Crooke et al., "Basic Principles of Antisense Therapeutics" Antisense Research and Application (1998) Chapter 1:1-50.
Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.
Donnelly et al., "Limited availability of ZBP1 restricts axonal mRNA localization and nerve regeneration capacity" EMBO J. (2011) 30:4665-4677.
Donnelly et al., "RNA toxicity from the ALS/FTD C9ORF72 expansion is mitigated by antisense intervention" (2013) 80(2):415-428.
Elayadi et al., "Application of PNA and LNA oligomers to chemotherapy" Curr. Opinion Invens. Drugs (2001) 2:558-561.
Freier et al., "The ups and downs of nucleic acid duplex stability: structure-stability studies on chemically-modified DNA:RNA duplexes " Nucleic Acids Research (1997) 25(22):4429-4443.
Frieden et al., "Expanding the design horizon of antisense oligonucleotides with alpha-L-LNA" Nucleic Acids Research (2003)31(21):6365-6372.
Gautschi et al., "Activity of a novel bcl-2/bcl-xLbispecific antisense oligonucleotide against tumors of diverse histologic origins" J. Natl. Cancer Inst. (2001) 93:463-471.
Hirtz et al., "How common are the "common" neurologic disorders?" Neurology (2007) 68:326-337.
International Search Report for application PCT/US2013/065131 dated Feb. 14, 2014.
Jeong et al., "Rapid Identification of Monospecific Monoclonal Antibodies Using a Human Proteome Microarray." Mol. Cell. Proteomics (2012) 11(6): O111.016253-1 to O111.016253-10.
Johnson et al., "Exome sequencing reveals VCP mutations as a cause of familial ALS" Neuron (2010) 68:857-864.
Jones et al., "RNA quantitation by fluorescence-based solution assay: RiboGreen reagent characterization" Analytical Biochemistry (1998) 265(2):368-374.
Klein et al., "Gain of RNA function in pathological cases: Focus on myotonic dystrophy" Biochimie (2011) 93(11):2006-2012.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Kwiatkowski et al., "Mutations in the FUS/TLS gene on chromosome 16 cause familial amyotrophic lateral sclerosis" Science (2009) 323:1205-1208.
Laaksovirta et al, "Chromosome 9p21 in amyotrophic lateral sclerosis in Finland: a genome-wide association study" Lancet Neurol. (2010) 9:978-985.
Leumann et al., "DNA Analogues: From Supramolecular Principles to Biological Properties" Bioorganic & Medicinal Chemistry (2002) 10:841-854.

(56) References Cited

OTHER PUBLICATIONS

Lillo et al., "Frontotemporal dementia and motor neurone disease: overlapping clinic-pathological disorders" J. Clin. Neurosci. (2009) 16:1131-1135.
Madson, "Antisense Against C9ORF72", http://alsn.mda.org/article/antisense-against-c9Orf72 (printed Oct. 28, 2015).
Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.
Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Helv. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Mulders et al., "Triplet-repeat oligonucleotide-mediated reversal of RNA toxicity in myotonic dystrophy" (2009) 106(33):13915-13920.
Neumann et al., "Ubiquitinated TDP-43 in frontotemporal lobar degeneration and amyotrophic lateral sclerosis" Science (2006) 314:130-133.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Pearson et al., "Familial frontotemporal dementia with amyotrophic lateral sclerosis and a shared haplotype on chromosome 9p" J. Nerol. (2011) 258:647-655.
Rabin et al., "Sporadic ALS has compartment-specific aberrant exon splicing and altered cell-matrix adhesion biology" Hum Mol Genet. (2010) 19(2):313-328.
Renton et al., "A Hexanucleotide Repeat Expansion in C9ORF72 Is the Cause of Chromosome 9p21-Linked ALS-FTD" Neuron (2011) 72:257-268.
Reynolds et al., "Rational siRNA design for RNA interference" Nature Biotechnology (2004) 22(3):326-330.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sanghvi et al., "Heterocyclic Base Modifications in Nucleic Acids and Their Applications in Antisense Oligonucleotides" Antisense Research and Applications (1993) pp. 273-288.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of biosequences" Adv. Appl. Math. (1981) 2(4):482-489.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Natl. Acad. Sci. USA (2000) 97: 5633-5638.
Woolf et al., "Specificity of antisense oligonucleotides in vivo" PNAS (1992) 89: 7305-7309.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.
Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.
Baloh, R.H., "Targeting RNA foci shows a therapeutic effect in iPSC-derived motor neurons from C9orf72 repeat patients" ALSMND meeting, Milan, Dec. 6, 2013.
Baloh, R.H., "Induced Pluripotent stem cell models from C9orf72 patients." Oral presentation, California ALS PAC10 Research Summit, Los Angeles, CA, Nov. 11, 2012.
Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.
Baughn et al, "Sense and Anti-Sense RNA Foci in c9ALS/FTD: More Light in a House of Mirrors" Annals of Neurology (Dec. 2013) 74(17): pS60.
Brettschneider et al., "Microglial activation correlates with disease progression and upper motor neuron clinical symptoms in Amyotrophic Lateral Sclerosis", PLOS ONE (2012) 7:e39216.
Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4dle-9569-9albleb21d80&cKey=c5c69155-5d2b-467c-8d1f-87299c514c7f&mKey=%7b70007181-01C9-4DE9-A0A2-EEBFA14CD9F1%7d.
Donnelly et al., "Development of C9ORF72 ALS Biomarkers and Therapeutics" American Neurological Association 2012 Annual Meeting, Poster Presentation, Boston, MA Oct. 10, 2012.
Donnelly et al., "Development of C9orf72 ALS Biomarkers and Therapeutics" Annals of Neuology (Oct. 10, 2012) 72(16):567-568.
Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.
Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.
European Search Report for application No. 13847957.1 dated Jul. 13, 2016.
European Search Report for application No. 13846313.8 dated May 11, 2016.
European Search Report for application No. 13847099.2 dated May 25, 2016.
File History of U.S. Appl. No. 14/436,030, filed Apr. 15, 2015.
File History of U.S. Appl. No. 14/436,024, filed Apr. 15, 2015.
Ganesalingam et al., "Combination of neurofilament heavy chain and complement C3 as CSF biomarkers for ALS" Journal of Neurochemistry (2011) 117: 528-537.
Ince et al., "Molecular pathology and genetic advances in amyotrophic lateral sclerosis: an emerging molecular pathway and the significance of glial pathology," Acta Neuro. (2011) 122:657-671.

(56) References Cited

OTHER PUBLICATIONS

Jiang et al., "Antisense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.
Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.
Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.
Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.
Lagier-Tourenne, C. "Therapy Development for ALS/MND and Frontotemporal Dementia with C9orf72 Expansion: Antisense Oligonucleotide Mediated Reduction in Nuclear RNA Foci." ALS FD (Nov. 4, 2013) 14(sup2): p. 17.
Lindquist et al, "Corticobasal and ataxia syndromes widen the spectrum of C9ORF72 hexanucleotide expansion disease." Clin Genet (2013) 83:279-283.
O'Rourke et al., "C9orf72 BAC Transgenic Mice Display Typical Pathologic Features of ALS/FTD." Neuron (2015) 88(5):892-901.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Ravits, J., "Expanding Neurodegeneration: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Riboldi et al., "Antisense Oligonucleotide Therapy for the Treatment of C9ORF72 ALS/FTD Diseses." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, The Netherlands; Oct. 11-14, 2015.
Sareen, et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Simon-Sanchez et al., "The clinical and pathological phenoype of C9OFR72 hexanucleotide repeat expansions", Brain: Journal of Neurology (2012) 135:723-735.
Todd et al. "RNA mediated neurodegeneration in repeat expansion disorders," Annals of Neruology (2009) 67(3):291-300.
Wojciechowska et al., "Cellular toxicity of expanded RNA repeats: focus on RNA foci" Human Molecular Genetics (2011) 1-11.
Zhang et al., "The C9orf72 repeat expansion disrupts nucleocytoplasmic transport." Nature (2015) 525(7567):56-61.
International Search Report for application No. PCT/US2013/065073 dated Apr. 22, 2014.
International Search Report for application PCT/US13/65067 dated Jan. 24, 2014.
Lagier-Tourenne et al., "Targeted Degradation of Sense and Antisense C9ORF72 RNA Foci as Therapy for ALS and Frontotemporal Degeneration" PNAS (2013) 1-10.
File History of U.S. Appl. No. 15/028,626, filed Apr. 11, 2016.
File History of U.S. Appl. No. 15/130,818, filed Apr. 15, 2016.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=1&satkey=24474174).
International Search Report for application on. PCT/US2014/060194 dated Apr. 14, 2015.
Nelson et al., "The unstable repeats—three evolving faces of neurological disease." Neuron (2013) 77(5):825-43.
"The ALS Association and the Packard Center Partner to Develop Animal Model Systems for Most Common Cause of Familial ALS," http://www.alsa.org/news/archive/new-animal-model-systems.html Mar. 1, 2012 (printed Oct. 25, 2015), 4 pages.
International Search Report for application in PCT/US2016/027747 dated Sep. 30, 2016 12 pages.
International Search Report for application in PCT/US2017/027355 dated Jul. 26, 2017, 11 pages.
Ash et al., "Unconventional Translation of C9ORF72 GGGGCC Expansion Generates Insoluble Ploypeptides Specific to c9FTD/ALS" Neuron (2013) 77(4): 639-646.
Extended European Search Report for application No. 14652924.1 dated Jun. 20, 2017, 13 pages.
Fernandes et al., "Oligonucleotide-Based Therapy for FTD/ALS Caused by the C9orf72 Repeat Expansion: A Perspective" Journal of Nucleic Acids (2013) :1-11.
Gendron et al., "Poly(GP) proteins are a useful pharmacodynamic marker for C9ORF72-associated amyotrophic lateral sclerosis" Sci Tran Med (2017) 9(383):1-12.
Lee et al., "Antisense Therapy in Neurology" Journal of Personalized Medicine (2013) 3(3): 144-176.
Mahoney et al., "Frontotemporal Dementia with the C9ORF72 Hexanucleotide Repeat Expansion: Clinical, Neuroanatomical and Neuropathological Features," Brain, 2012, 135:736-750.
Sha et al., "Treatment implications of C9ORF72" Alzheimers Res Ther (2012) 4(6): 46.
Thomsen, "Dramatically improved RNA in 1-15 situ hybridization signals using LNA-modified probes" RNA (2005) 11(11): 1745-1746.
GenBank: Accession No. NT_008413, Jul. 24, 2012, 5 pages.
International Search Report for Application No. PCT/US2016/060106 dated Feb. 1, 2017, 10 pages.
Bennett et al., "Antisense oligonucleotides as a tool for gene functionalization and target validation," Biochimica et Biophysica Acta (1999) 1489: 19-30.
Ciura et al., "Loss of function of C9orf72 causes motor deficits in a zebrafish model of amyotrophic lateral sclerosis" Ann Neurol (2013) 74(2): 180-187.
Extended European Search Report for application No. 16780833.6 dated Nov. 15, 2018.
Watts et al., "Silencing disease genes in the laboratory and the clinic" J Pathol (2012) 226(2): 365-379.

* cited by examiner

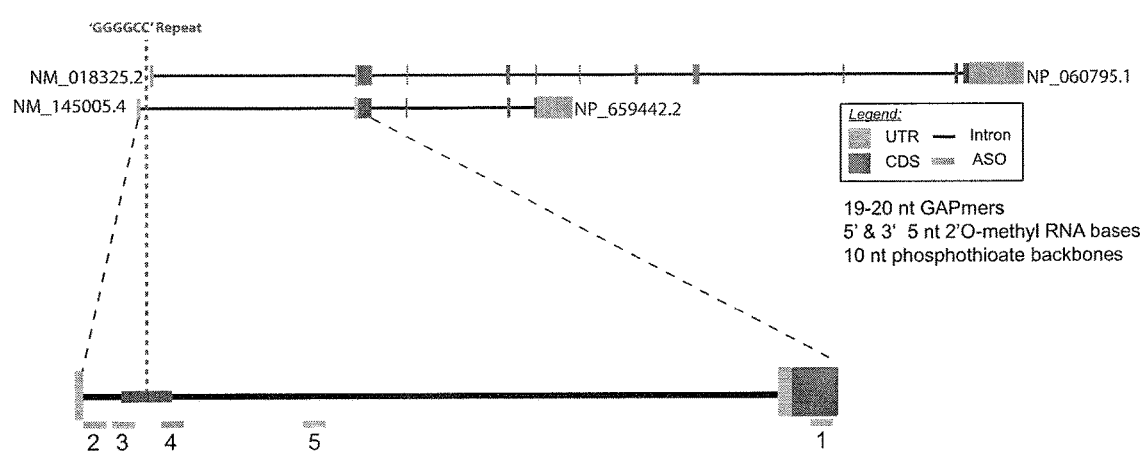
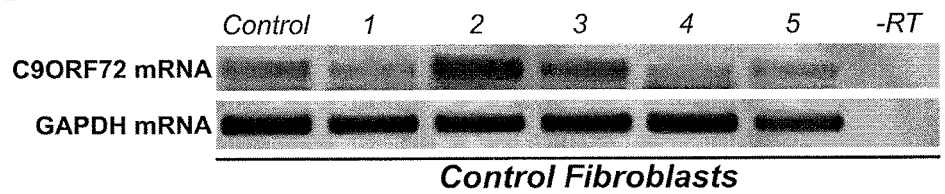
Figure 1 a-b

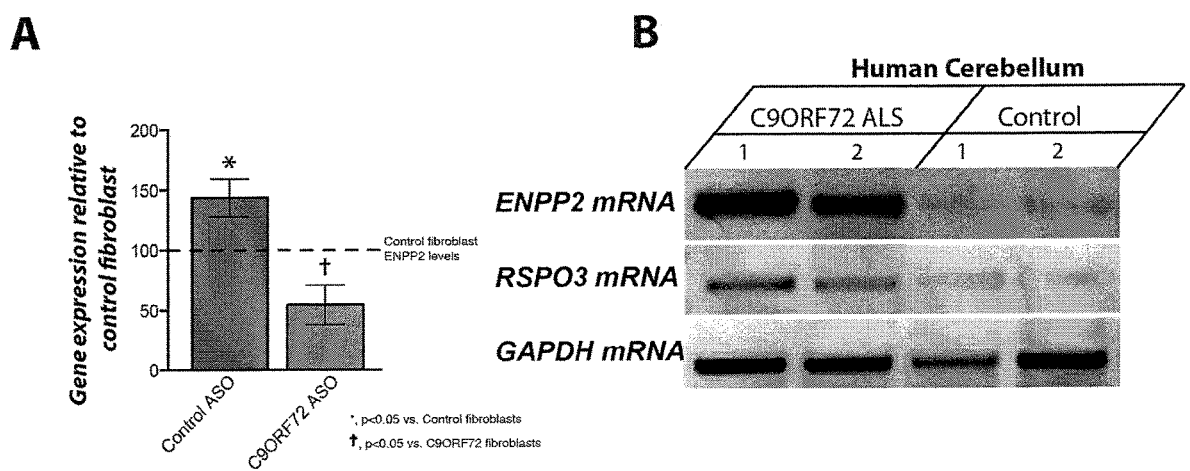
Figure 2 a-b

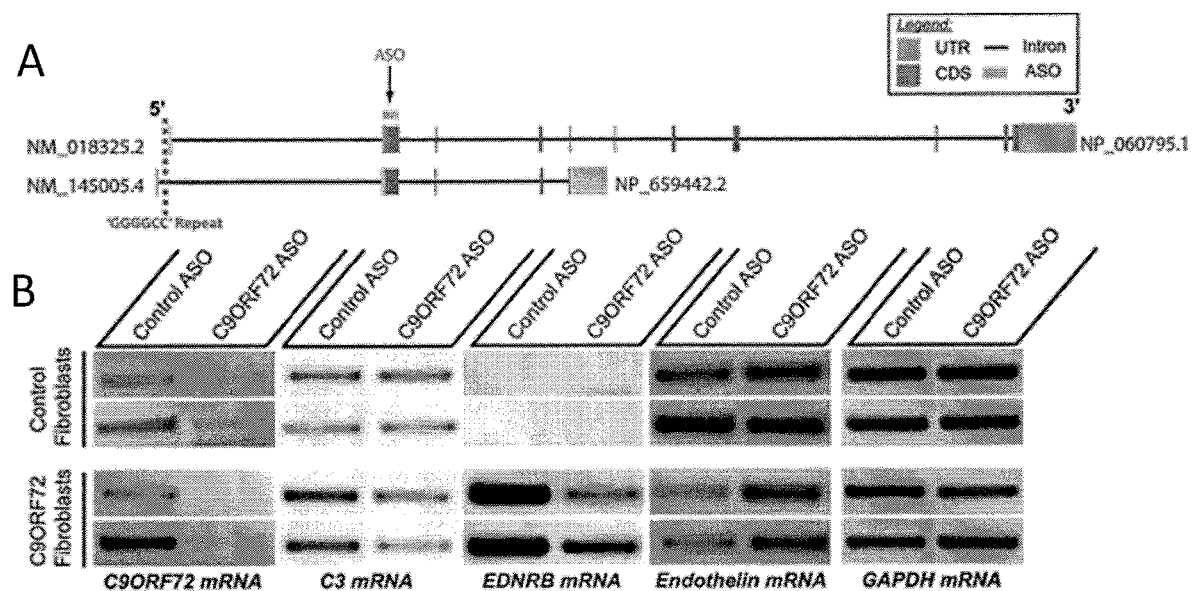
Figure 3 a-b

SEQUENCE LISTING

```
<160> NUMBER OF SEQ ID NOS: 31

<210> SEQ ID NO 1
<211> LENGTH: 3339
<212> TYPE: DNA
<213> ORGANISM: Homo sapiens
<220> FEATURE:
<221> NAME/KEY: CDS
<222> LOCATION: (203)..(1648)

<400> SEQUENCE: 1
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata     180
atgtgacagt tggaatgcag tg atg tcg act ctt tgc cca ccg cca tct cca    232
                          Met Ser Thr Leu Cys Pro Pro Pro Ser Pro
                            1               5                  10 gct gtt gcc aag aca gag att gct tta agt ggc aaa tca cct tta tta    280
Ala Val Ala Lys Thr Glu Ile Ala Leu Ser Gly Lys Ser Pro Leu Leu
                15                  20                  25 gca gct act ttt gct tac tgg gac aat att ctt ggt cct aga gta agg    328
Ala Ala Thr Phe Ala Tyr Trp Asp Asn Ile Leu Gly Pro Arg Val Arg
            30                  35                  40 cac att tgg gct cca aag aca gaa cag gta ctt ctc agt gat gga gaa    376
His Ile Trp Ala Pro Lys Thr Glu Gln Val Leu Leu Ser Asp Gly Glu
        45                  50                  55
```

-continued

| | | |
|---|---|---|
| ata act ttt ctt gcc aac cac act cta aat gga gaa atc ctt cga aat<br>Ile Thr Phe Leu Ala Asn His Thr Leu Asn Gly Glu Ile Leu Arg Asn<br>    60              65              70 | 424 |
| gca gag agt ggt gct ata gat gta aag ttt ttt gtc ttg tct gaa aag<br>Ala Glu Ser Gly Ala Ile Asp Val Lys Phe Phe Val Leu Ser Glu Lys<br>75              80              85              90 | 472 |
| gga gtg att att gtt tca tta atc ttt gat gga aac tgg aat ggg gat<br>Gly Val Ile Ile Val Ser Leu Ile Phe Asp Gly Asn Trp Asn Gly Asp<br>            95              100             105 | 520 |
| cgc agc aca tat gga cta tca att ata ctt cca cag aca gaa ctt agt<br>Arg Ser Thr Tyr Gly Leu Ser Ile Ile Leu Pro Gln Thr Glu Leu Ser<br>        110             115             120 | 568 |
| ttc tac ctc cca ctt cat aga gtg tgt gtt gat aga tta aca cat ata<br>Phe Tyr Leu Pro Leu His Arg Val Cys Val Asp Arg Leu Thr His Ile<br>    125             130             135 | 616 |
| atc cgg aaa gga aga ata tgg atg cat aag gaa aga caa gaa aat gtc<br>Ile Arg Lys Gly Arg Ile Trp Met His Lys Glu Arg Gln Glu Asn Val<br>140             145             150 | 664 |
| cag aag att atc tta gaa ggc aca gag aga atg gaa gat cag ggt cag<br>Gln Lys Ile Ile Leu Glu Gly Thr Glu Arg Met Glu Asp Gln Gly Gln<br>155             160             165             170 | 712 |
| agt att att cca atg ctt act gga gaa gtg att cct gta atg gaa ctg<br>Ser Ile Ile Pro Met Leu Thr Gly Glu Val Ile Pro Val Met Glu Leu<br>            175             180             185 | 760 |
| ctt tca tct atg aaa tca cac agt gtt cct gaa gaa ata gat ata gct<br>Leu Ser Ser Met Lys Ser His Ser Val Pro Glu Glu Ile Asp Ile Ala<br>        190             195             200 | 808 |
| gat aca gta ctc aat gat gat gat att ggt gac agc tgt cat gaa ggc<br>Asp Thr Val Leu Asn Asp Asp Asp Ile Gly Asp Ser Cys His Glu Gly<br>    205             210             215 | 856 |
| ttt ctt ctc aat gcc atc agc tca cac ttg caa acc tgt ggc tgt tcc<br>Phe Leu Leu Asn Ala Ile Ser Ser His Leu Gln Thr Cys Gly Cys Ser<br>220             225             230 | 904 |
| gtt gta gta ggt agc agt gca gag aaa gta aat aag ata gtc aga aca<br>Val Val Val Gly Ser Ser Ala Glu Lys Val Asn Lys Ile Val Arg Thr<br>235             240             245             250 | 952 |
| tta tgc ctt ttt ctg act cca gca gag aga aaa tgc tcc agg tta tgt<br>Leu Cys Leu Phe Leu Thr Pro Ala Glu Arg Lys Cys Ser Arg Leu Cys<br>            255             260             265 | 1000 |
| gaa gca gaa tca tca ttt aaa tat gag tca ggg ctc ttt gta caa ggc<br>Glu Ala Glu Ser Ser Phe Lys Tyr Glu Ser Gly Leu Phe Val Gln Gly<br>        270             275             280 | 1048 |
| ctg cta aag gat tca act gga agc ttt gtg ctg cct ttc cgg caa gtc<br>Leu Leu Lys Asp Ser Thr Gly Ser Phe Val Leu Pro Phe Arg Gln Val<br>    285             290             295 | 1096 |
| atg tat gct cca tat ccc acc aca cac ata gat gtg gat gtc aat act<br>Met Tyr Ala Pro Tyr Pro Thr Thr His Ile Asp Val Asp Val Asn Thr<br>300             305             310 | 1144 |
| gtg aag cag atg cca ccc tgt cat gaa cat att tat aat cag cgt aga<br>Val Lys Gln Met Pro Pro Cys His Glu His Ile Tyr Asn Gln Arg Arg<br>315             320             325             330 | 1192 |
| tac atg aga tcc gag ctg aca gcc ttc tgg aga gcc act tca gaa gaa<br>Tyr Met Arg Ser Glu Leu Thr Ala Phe Trp Arg Ala Thr Ser Glu Glu<br>            335             340             345 | 1240 |
| gac atg gct cag gat acg atc atc tac act gac gaa agc ttt act cct<br>Asp Met Ala Gln Asp Thr Ile Ile Tyr Thr Asp Glu Ser Phe Thr Pro<br>        350             355             360 | 1288 |
| gat ttg aat att ttt caa gat gtc tta cac aga gac act cta gtg aaa<br>Asp Leu Asn Ile Phe Gln Asp Val Leu His Arg Asp Thr Leu Val Lys<br>    365             370             375 | 1336 |

```
gcc ttc ctg gat cag gtc ttt cag ctg aaa cct ggc tta tct ctc aga      1384
Ala Phe Leu Asp Gln Val Phe Gln Leu Lys Pro Gly Leu Ser Leu Arg
    380                 385                 390 agt act ttc ctt gca cag ttt cta ctt gtc ctt cac aga aaa gcc ttg      1432
Ser Thr Phe Leu Ala Gln Phe Leu Leu Val Leu His Arg Lys Ala Leu
395                 400                 405                 410 aca cta ata aaa tat ata gaa gac gat acg cag aag gga aaa aag ccc      1480
Thr Leu Ile Lys Tyr Ile Glu Asp Asp Thr Gln Lys Gly Lys Lys Pro
                415                 420                 425 ttt aaa tct ctt cgg aac ctg aag ata gac ctt gat tta aca gca gag      1528
Phe Lys Ser Leu Arg Asn Leu Lys Ile Asp Leu Asp Leu Thr Ala Glu
            430                 435                 440 ggc gat ctt aac ata ata atg gct ctg gct gag aaa att aaa cca ggc      1576
Gly Asp Leu Asn Ile Ile Met Ala Leu Ala Glu Lys Ile Lys Pro Gly
        445                 450                 455 cta cac tct ttt atc ttt gga aga cct ttc tac act agt gtg caa gaa      1624
Leu His Ser Phe Ile Phe Gly Arg Pro Phe Tyr Thr Ser Val Gln Glu
    460                 465                 470 cga gat gtt cta atg act ttt taa atgtgtaact taataagcct attccatcac     1678
Arg Asp Val Leu Met Thr Phe
475                 480
```
aatcatgatc gctggtaaag tagctcagtg gtgtggggaa acgttcccct ggatcatact    1738
ccagaattct gctctcagca attgcagtta agtaagttac actacagttc tcacaagagc    1798
ctgtgagggg atgtcaggtg catcattaca ttgggtgtct cttttcctag atttatgctt    1858
ttgggataca gacctatgtt tacaatataa taaatattat tgctatcttt taaagatata    1918
ataataggat gtaaacttga ccacaactac tgttttttg aaatacatga ttcatggttt     1978
acatgtgtca aggtgaaatc tgagttggct tttacagata gttgactttc tatcttttgg    2038
cattctttgg tgtgtagaat tactgtaata cttctgcaat caactgaaaa ctagagcctt    2098
taaatgattt caattccaca gaaagaaagt gagcttgaac ataggatgag ctttagaaag    2158
aaaattgatc aagcagatgt taattggaa ttgattatta gatcctactt tgtggattta    2218
gtccctggga ttcagtctgt agaaatgtct aatagttctc tatagtcctt gttcctggtg    2278
aaccacagtt agggtgtttt gtttatttta ttgttcttgc tattgttgat attctatgta    2338
gttgagctct gtaaaggaa attgtatttt atgttttagt aattgttgcc aacttttaa     2398 attaattttc attattttg agccaaattg aaatgtgcac ctcctgtgcc ttttttctcc    2458
ttagaaaatc taattacttg gaacaagttc agatttcact ggtcagtcat tttcatcttg    2518
ttttcttctt gctaagtctt accatgtacc tgctttggca atcattgcaa ctctgagatt    2578
ataaaatgcc ttagagaata tactaactaa taagatcttt ttttcagaaa cagaaaatag    2638
ttccttgagt acttccttct tgcatttctg cctatgtttt tgaagttgtt gctgtttgcc    2698
tgcaataggc tataaggaat agcaggagaa attttactga agtgctgttt tcctaggtgc    2758
tactttggca gagctaagtt atcttttgtt ttcttaatgc gtttggacca ttttgctggc    2818
tataaaataa ctgattaata taattctaac acaatgttga cattgtagtt acacaaacac    2878
aaataaatat tttatttaaa attctggaag taatataaaa gggaaaatat atttataaga    2938
aagggataaa ggtaatagag cccttctgcc ccccacccac caaatttaca caacaaaatg    2998
acatgttcga atgtgaaagg tcataatagc tttcccatca tgaatcagaa agatgtggac    3058
agcttgatgt tttagacaac cactgaacta gatgactgtt gtactgtagc tcagtcattt    3118
aaaaaatata taaatactac cttgtagtgt cccatactgt gttttttaca tggtagattc    3178
ttatttaagt gctaactggt tattttcttt ggctggttta ttgtactgtt atacagaatg    3238

| | |
|---|---:|
| taagttgtac agtgaaataa gttattaaag catgtgtaaa cattgttata tatctttctct | 3298 |
| cctaaatgga gaattttgaa taaaatatat ttgaaatttt g | 3339 |

<210> SEQ ID NO 2
<211> LENGTH: 30001
<212> TYPE: DNA
<213> ORGANISM: Homo sapiens

<400> SEQUENCE: 2

| | |
|---|---:|
| caaagaaaag ggggaggttt tgttaaaaaa gagaaatgtt acatagtgct ctttgagaaa | 60 |
| attcattggc actattaagg atctgaggag ctggtgagtt tcaactgtg agtgatggtg | 120 |
| gtagataaaa ttagagctgc agcaggtcat tttagcaact attagataaa actggtctca | 180 |
| ggtcacaacg ggcagttgca gcagctggac ttggagagaa ttacactgtg ggagcagtgt | 240 |
| catttgtcct aagtgctttt ctaccccta cccccactat tttagttggg tataaaaaga | 300 |
| atgacccaat ttgtatgatc aactttcaca aagcatagaa cagtaggaaa agggtctgtt | 360 |
| tctgcagaag gtgtagacgt tgagagccat tttgtgtatt tattcctccc tttcttcctc | 420 |
| ggtgaatgat taaaacgttc tgtgtgattt ttagtgatga aaaagattaa atgctactca | 480 |
| ctgtagtaag tgccatctca cacttgcaga tcaaaaggca cacagtttaa aaaacctttg | 540 |
| ttttttaca catctgagtg gtgtaaatgc tactcatctg tagtaagtgg aatctataca | 600 |
| cctgcagacc aaaagacgca aggtttcaaa aatctttgtg ttttttacac atcaaacaga | 660 |
| atggtacgtt tttcaaaagt taaaaaaaaa caactcatcc acatattgca actagcaaaa | 720 |
| atgacattcc ccagtgtgaa aatcatgctt gagagaattc ttacatgtaa aggcaaaatt | 780 |
| gcgatgactt tgcaggggac cgtgggattc ccgcccgcag tgccggagct gtcccctacc | 840 |
| agggtttgca gtggagtttt gaatgcactt aacagtgtct tacggtaaaa acaaaatttc | 900 |
| atccaccaat tatgtgttga gcgcccactg cctaccaagc acaaacaaaa ccattcaaaa | 960 |
| ccacgaaatc gtcttcactt tctccagatc cagcagcctc ccctattaag gttcgcacac | 1020 |
| gctattgcgc caacgctcct ccagagcggg tcttaagata aagaacagg acaagttgcc | 1080 |
| ccgccccatt tcgctagcct cgtgagaaaa cgtcatcgca catagaaaac agacagacgt | 1140 |
| aacctacggt gtcccgctag gaaagagagg tgcgtcaaac agcgacaagt tccgcccacg | 1200 |
| taaaagatga cgcttggtgt gtcagccgtc cctgctgccc ggttgcttct cttttggggg | 1260 |
| cggggtctag caagagcagg tgtgggttta ggaggtgtgt gtttttgttt ttcccacct | 1320 |
| ctctccccac tacttgctct cacagtactc gctgagggtg aacaagaaaa gacctgataa | 1380 |
| agattaacca gaagaaaaca aggagggaaa caaccgcagc ctgtagcaag ctctggaact | 1440 |
| caggagtcgc gcgctagggg ccggggccgg ggccggggcg tggtcggggc gggcccgggg | 1500 |
| gcgggcccgg ggcggggctg cggttgcggt gcctgcgccc gcggcggcgg aggcgcaggc | 1560 |
| ggtggcgagt gggtgagtga ggaggcggca tcctggcggg tggctgtttg gggttcggct | 1620 |
| gccgggaaga ggcgcgggta gaagcggggg ctctcctcag agctcgacgc attttttactt | 1680 |
| tccctctcat ttctctgacc gaagctgggt gtcgggcttt cgcctctagc gactggtgga | 1740 |
| attgcctgca tccgggcccc gggcttcccg gcggcggcgg cggcggcggc ggcgcaggga | 1800 |
| caagggatgg ggatctggcc tcttccttgc tttcccgccc tcagtacccg agctgtctcc | 1860 |
| ttcccgggga ccccctggga gcgctgccgc tgcgggctcg agaaaaggga gcctcgggta | 1920 |
| ctgagaggcc tcgcctgggg gaaggccgga gggtgggcgg cgcgcggctt ctgcggacca | 1980 |
| agtcggggtt cgctaggaac ccgagacggt ccctgccggc gaggagatca tgcgggatga | 2040 |

```
gatgggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tagggggat attaataacc    2640 tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctctttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat tttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga tttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg gctaattttt tgtatttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc attttttttt tcttattctg    4440
```

```
ttaggagtga gagtgtaact agcagtataa tagttcaatt ttcacaacgt ggtaaaagtt    4500
tccctataat tcaatcagat tttgctccag ggttcagttc tgttttagga aatactttta    4560
ttttcagttt aatgatgaaa tattagagtt gtaatattgc ctttatgatt atccaccttt    4620
ttaacctaaa agaatgaaag aaaaatatgt ttgcaatata attttatggt tgtatgttaa    4680
cttaattcat tatgttggcc tccagtttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920 attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgcttttccat cagactgaac tctcttgaca agatgtggat    5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatagtac aatcacacat tgcttaggaa    5340
tgcatcatta ggcgattttg tcattatgca aacatcatag agtgtactta cacaaaccta    5400
gatagtatag cctttatgta cctaggccgt atggtatagt ctgttgctcc taggccacaa    5460
acctgtacaa ctgttactgt actgaatact atagacagtt gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac tttttaactt tgtaaacttt ttaattttt aacttttaaa atacttagct    5820
tgaaacacaa atacattgta tagctataca aaaatatttt ttctttgtat ccttattcta    5880
gaagcttttt tctatttct atttttaaatt ttttttttta cttgttagtc gtttttgtta    5940
aaaactaaaa cacacacact ttcacctagg catagacagg attaggatca tcagtatcac    6000 tccctttccac ctcactgcct tccacctcca catcttgtcc cactggaagg ttttttaggg    6060
caataacaca catgtagctg tcacctatga taacagtgct ttctgttgaa tacctcctga    6120
aggacttgcc tgaggctgtt ttacatttaa cttaaaaaaa aaaaaagtag aaggagtgca    6180
ctctaaaata acaataaaag gcatagtata gtgaatacat aaaccagcaa tgtagtagtt    6240
tattatcaag tgttgtacac tgtaataatt gtatgtgcta tactttaaat aacttgcaaa    6300
atagtactaa gaccttatga tggttacagt gtcactaagg caatagcata ttttcaggtc    6360
cattgtaatc taatgggact accatcatat atgcagtcta ccattgactg aaacgttaca    6420
tggcacataa ctgtatttgc aagaatgatt tgttttacat taatatcaca taggatgtac    6480 cttttttagag tggtatgttt atgtggatta agatgtacaa gttgagcaag gggaccaaga    6540
gccctgggtt ctgtcttgga tgtgagcgtt tatgttcttc tcctcatgtc tgttttctca    6600
ttaaattcaa aggcttgaac gggccctatt tagcccttct gttttctacg tgttctaaat    6660
aactaaagct tttaaattct agccatttag tgtagaactc tctttgcagt gatgaaatgc    6720
tgtattggtt tcttggctag catattaaat atttttatct ttgtcttgat acttcaatgt    6780
cgttttaaac atcaggatcg ggcttcagta ttctcataac cagagagttc actgaggata    6840
```

```
caggactgtt tgcccatttt ttgttatggc tccagacttg tggtatttcc atgtcttttt    6900
tttttttttt tttttttgacc ttttagcggc tttaaagtat ttctgttgtt aggtgttgta    6960
ttacttttct aagattactt aacaaagcac cacaaactga gtggctttaa acaacagcaa    7020
tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgaccccatt ttaacatgat tacacttatt    7320
tctagataag gtcacattca cgtacaccaa gggttaggaa ttgaacatat cttttggggg    7380
gacacaattc aacccacaag tgtcagtctc tagctgagcc tttcccttcc tgttttttctc   7440 ctttttagtt gctatgggtt aggggccaaa tctccagtca tactagaatt gcacatggac    7500
tggatatttg ggaatactgc gggtctattc tatgagcttt agtatgtaac atttaatatc    7560
agtgtaaaga agccctttt taagttattt ctttgaattt ctaaatgtat gccctgaata     7620
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttggggtt ttgatggata tcttaaatt     7800 gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgatttttc    8340
agcttattaa tcatgttaac ctatctgttg aaagcttatt ttctggtaca tataaatctt    8400 attttttaa ttatatgcag tgaacatcaa acaataaatg ttatttattt tgcatttacc      8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata ccttttgttt ccctttcatt    8640
gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat ttttactat gtttgcaggc ttacttcctt ttttctcaca     9060
ttatgaaact cttaaaatca ggagaatctt ttaaacaaca tcataatgtt taatttgaaa    9120
agtgcaagtc attctttttcc ttttttgaaac tatgcagatg ttacattgac tgttttctgt   9180
gaagttatct ttttttcact gcagaataaa ggttgttttg attttatttt gtattgttta    9240
```

```
tgagaacatg catttgttgg gttaatttcc taccoctgcc cccattttt  ccctaaagta    9300 gaaagtattt ttcttgtgaa ctaaattact acacaagaac atgtctattg aaaaataagc    9360
aagtatcaaa atgttgtggg ttgttttttt aaataaattt tctcttgctc aggaaagaca    9420
agaaaatgtc cagaagatta tcttagaagg cacagagaga atggaagatc aggtatatgc    9480
aaattgcata ctgtcaaatg ttttttctcac agcatgtatc tgtataaggt tgatggctac   9540
atttgtcaag gccttggaga catacgaata agcctttaat ggagctttta tggaggtgta    9600
cagaataaac tggaggaaga tttccatatc ttaaacccaa agagttaaat cagtaaacaa    9660
aggaaaatag taattgcatc tacaaattaa tatttgctcc cttttttttt ctgtttgccc    9720
agaataaatt ttggataact tgttcatagt aaaaataaaa aaaattgtct ctgatatgtt    9780
ctttaaggta ctacttctcg aacctttccc tagaagtagc tgtaacagaa ggagagcata    9840 tgtaccoctg aggtatctgt ctggggtgta ggcccaggtc cacacaatat tcttctaag    9900 tcttatgttg tatcgttaag actcatgcaa tttacatttt attccataac tattttagta    9960
ttaaaatttg tcagtgatat ttcttaccct ctcctctagg aaaatgtgcc atgtttatcc    10020
cttggctttg aatgcccctc aggaacagac actaagagtt tgagaagcat ggttacaagg   10080
gtgtggcttc ccctgcggaa actaagtaca gactatttca ctgtaaagca gagaagttct   10140
tttgaaggag aatctccagt gaagaaagag ttcttcactt ttacttccat ttcctcttgt   10200
gggtgaccct caatgctcct tgtaaaactc caatatttta aacatggctg ttttgccttt   10260
ctttgcttct ttttagcatg aatgagacag atgatacttt aaaaaagtaa ttaaaaaaaa   10320
aaacttgtga aaatacatgg ccataataca gaacccaata caatgatctc ctttaccaaa   10380
ttgttatgtt tgtacttttg tagatagctt tccaattcag agacagttat tctgtgtaaa   10440
ggtctgactt aacaagaaaa gatttcccctt tacccaaaga atcccagtcc ttatttgctg   10500
gtcaataagc agggtcccca ggaatggggt aactttcagc accctctaac ccactagtta   10560
ttagtagact aattaagtaa acttatcgca agttgaggaa acttagaacc aactaaaatt   10620
ctgcttttac tgggattttg ttttttcaaa ccagaaacct ttacttaagt tgactactat   10680
taatgaattt tggtctctct tttaagtgct cttcttaaaa atgttatctt actgctgaga   10740
agttcaagtt tgggaagtac aaggaggaat agaaacttaa gagattttct tttagagcct   10800
cttctgtatt tagccoctgta ggattttttt tttttttttt tttttggtg ttgttgagct   10860 tcagtgaggc tattcattca cttatactga taatgtctga gatactgtga atgaaatact   10920
atgtatgctt aaacctaaga ggaaatattt tcccaaaatt attcttcccg aaaaggagga   10980
gttgcctttt gattgagttc ttgcaaatct cacaacgact ttattttgaa caatactgtt   11040 tgggatgat gcattagttt gaacaacctt cagttgtagc tgtcatctga taaaattgct    11100
tcacagggaa ggaaatttaa cacggatcta gtcattattc ttgttagatt gaatgtgtga   11160
attgtaattg taaacaggca tgataattat tactttaaaa actaaaaaca gtaatagtt    11220 agttgtggag gttactaaag gatggttttt ttttaaataa aactttcagc attatgcaaa   11280
tgggcatatg gcttaggata aaacttccag aagtagcatc acatttaaat tctcaagcaa   11340
cttaataata tggggctctg aaaaactggt taaggttact ccaaaaatgg ccctgggtct   11400
gacaaagatt ctaacttaaa gatgcttatg aagactttga gtaaaatcat ttcataaaat   11460
aagtgaggaa aaacaactag tattaaattc atcttaaata atgtatgatt taaaaaatat   11520
gtttagctaa aaatgcatag tcatttgaca atttcatttta tatctcaaaa aatttactta   11580
accaagttgg tcacaaaact gatgagactg gtggtggtag tgaataaatg agggaccatc   11640
```

-continued

```
catatttgag acactttaca tttgtgatgt gttatactga attttcagtt tgattctata    11700
gactacaaat ttcaaaatta caatttcaag atgtaataag tagtaatatc ttgaaatagc    11760
tctaaaggga atttttctgt tttattgatt cttaaaatat atgtgctgat tttgatttgc    11820
atttgggtag attatacttt tatgagtatg gaggttaggt attgattcaa gttttcctta    11880
cctatttggt aaggatttca aagtcttttt gtgcttggtt ttcctcattt ttaaatatga    11940
aatatattga tgacctttaa caaatttttt ttatctcaaa ttttaaagga gatcttttct    12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aaagtgagct ttggattgca    12360
tataaatcct ttagacatgt agtagacttg tttgatactg tgtttgaaca aattacgaag    12420
tattttcatc aaagaatgtt attgtttgat gttattttta tttttttattg cccagcttct    12480
ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660
ttttggggtt atagtattat tatgtatatt attaatattc taattttaat agtaaggact    12720
ttgtcataca tactattcac atacagtatt agccacttta gcaaataagc acacacaaaa    12780
tcctggattt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtcttttga acaaaactg tgtgccaaag tagtaaccat    12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
gcacagagat tgttttttgg ggagtcttga ttctcggaaa tgaaggcagt gtgttatatt    13260
gaatccagac ttccgaaaac ttgtatatta aaagtgttat ttcaacacta tgttacagcc    13320
agactaattt ттттатттттт тgатgcатттт tagatagctg atacagtact caatgatgat    13380
gататттggтg acagctgtca tgaaggcttt cttctcaagt aagaattttt cttttcataa    13440
aagctggatg aagcagatac catcttatgc tcacctatga сaагаtттgg aagaaagaaa    13500
атаасаgасt gtctactta g атт gt tctag gacattacg tatttgaact gttgctaaaa    13560
тт tgtgttat ттттсастса tt ататтт ст ататататтт ggtgttat tc сатт тgстат    13620
ttaaagaaac cgagtttcca tcccagacaa gaaatcatgg cccctt gctt gatt ct ggтт    13680
т стт gт ттт та ст т ст сатт а аag стаасag aat сст тт са т атт аagт т g т ас т gт аgат    13740
gаастт аagт т ат тт аgg cg т аgаасаааа тт атт сат ат т татас тgат сттттт ссат    13800
ссаgсаgт gg agtt т аgт ac тт ааgаgтт т gt gcccttaa accagactcc ctggattaat    13860
gст gт gt асс сgт gggcaag gt gcct gаат т ст стат аса сст ат тт сст сат ст gт ааа    13920
ат ggсаат aa т аgт aat agt ассtaat gt g т aggggttgtt at aagcat т g аgт ааgат aa    13980
ат аат ат ааа gcacttagaa cagt gcctgg aacat аааа а сасtтаат аа т аg стсат аg    14040
```

```
ctaacatttc ctatttacat ttcttctaga aatagccagt atttgttgag tgcctacatg    14100
ttagttcctt tactagttgc tttacatgta ttatcttata ttctgtttta aagtttcttc    14160
acagttacag attttcatga aattttactt ttaataaaag agaagtaaaa gtataaagta    14220 ttcacttta tgttcacagt cttttccttt aggctcatga tggagtatca gaggcatgag     14280
tgtgtttaac ctaagagcct aatggcttg aatcagaagc actttagtcc tgtatctgtt    14340
cagtgtcagc ctttcataca tcattttaaa tcccatttga ctttaagtaa gtcacttaat    14400
ctctctacat gtcaatttct tcagctataa aatgatggta tttcaataaa taaatacatt    14460
aattaaatga tattatactg actaattggg ctgttttaag gctcaataag aaaatttctg    14520
tgaaaggtct ctagaaaatg taggttccta tacaaataaa agataacatt gtgcttatag    14580
cttcggtgtt tatcatataa agctattctg agttatttga agagctcacc tactttttt    14640 tgtttttagt ttgttaaatt gttttatagg caatgttttt aatctgtttt ctttaactta    14700
cagtgccatc agctcacact tgcaaacctg tggctgttcc gttgtagtag gtagcagtgc    14760
agagaaagta aataaggtag tttatttat aatctagcaa atgatttgac tctttaagac     14820
tgatgatata tcatggattg tcatttaaat ggtaggttgc aattaaaatg atctagtagt    14880
ataaggaggc aatgtaatct catcaaattg ctaagacacc ttgtggcaac agtgagtttg    14940
aaataaactg agtaagaatc atttatcagt ttattttgat agctcggaaa taccagtgtc    15000
agtagtgtat aaatggtttt gagaatatat taaaatcaga tatataaaaa aaattactct    15060
tctatttccc aatgttatct ttaacaaatc tgaagatagt catgtacttt tggtagtagt    15120
tccaaagaaa tgttatttgt ttattcatct tgatttcatt gtcttcgctt tccttctaaa    15180
tctgtccctt ctagggagct attgggatta agtggtcatt gattattata ctttattcag    15240
taatgtttct gacccttcc ttcagtgcta cttgagttaa ttaaggatta atgaacagtt     15300
acatttccaa gcattagcta ataaactaaa ggattttgca cttttcttca ctgaccatta    15360
gttagaaaga gttcagagat aagtatgtgt atctttcaat ttcagcaaac ctaatttttt    15420
aaaaaaagtt ttacatagga aatatgttgg aaatgatact ttacaaagat attcataatt    15480 ttttttgta atcagctact ttgtatattt acatgagcct taatttatat ttctcatata    15540
accatttatg agagcttagt atacctgtgt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt tttaaacat ttttcccatc ctccatcctc ttgagggaga atagcttacc     15780
ttttatcttg ttttaatttg agaaagaagt tgccaccact ctaggttgaa aaccactcct    15840
ttaacataat aactgtggat atggtttgaa tttcaagata gttacatgcc ttttattt     15900 tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtctttttac ttcatgtttt aatgctaaaa    16380
tatttctttt tatagatagt cagaacatta tgccttttc tgactccagc agagagaaaa     16440
```

```
tgctccaggt tatgtgaagc agaatcatca tttaaatatg agtcagggct ctttgtacaa   16500
ggcctgctaa aggtatagtt tctagttatc acaagtgaaa ccacttttct aaaatcattt   16560
ttgagactct ttatagacaa atcttaaata ttagcattta atgtatctca tattgacatg   16620
cccagagact gacttccttt acacagttct gcacatagac tatatgtctt atggatttat   16680
agttagtatc atcagtgaaa caccatagaa taccctttgt gttccaggtg ggtccctgtt   16740
cctacatgtc tagcctcagg acttttttt ttttaacaca tgcttaaatc aggttgcaca   16800
tcaaaaataa gatcatttct ttttaactaa atagatttga attttattga aaaaaatttt   16860
taaacatctt taagaagctt ataggattta agcaattcct atgtatgtgt actaaaatat   16920
atatatttct atatataata tatattagaa aaaaattgta ttttttctttt atttgagtct   16980 actgtcaagg agcaaaacag agaaatgtaa attagcaatt atttataata cttaaaggga   17040
agaaagttgt tcaccttgtt gaatctatta ttgttatttc aattatagtc ccaagacgtg   17100
aagaaatagc tttcctaatg gttatgtgat tgtctcatag tgactacttt cttgaggatg   17160
tagccacggc aaaatgaaat aaaaaaattt aaaaattgtt gcaaatacaa gttatattag   17220
gcttttgtgc attttcaata atgtgctgct atgaactcag aatgatagta tttaaatata   17280
gaaactagtt aaaggaaacg tagtttctat ttgagttata catatctgta aattagaact   17340
tctcctgtta aaggcataat aaagtgctta atactttttgt ttcctcagca ccctctcatt   17400
taattatata attttagttc tgaaagggac ctataccaga tgcctagagg aaatttcaaa   17460
actatgatct aatgaaaaaa tatttaatag ttctccatgc aaatacaaat catatagttt   17520
tccagaaaat acctttgaca ttatacaaag atgattatca cagcattata atagtaaaaa   17580
aatggaaata gcctctttct tctgttctgt tcatagcaca gtgcctcata cgcagtaggt   17640
tattattaca tggtaactgg ctaccccaac tgattaggaa agaagtaaat ttgttttata   17700
aaaatacata ctcattgagg tgcatagaat aattaagaaa ttaaaagaca cttgtaattt   17760
tgaatccagt gaatacccac tgttaatatt tggtatatct cttctagtc ttttttttccc    17820 ttttgcatgt attttcttta agactcccac ccccactgga tcatctctgc atgttctaat   17880 ctgcttttttt cacagcagat tctaagcctc tttgaatatc aacacaaact tcaacaactt   17940
catctataga tgccaaataa taaattcatt tttatttact taaccacttc ctttggatgc   18000
ttaggtcatt ctgatgtttt gctattgaaa ccaatgctat actgaacact tctgtcacta   18060
aaactttgca cacactcatg aatagcttct taggataaat ttttagagat ggatttgcta   18120
aatcagagac cattttttaa aattaaaaaa caattattca tatcgtttgg catgtaagac   18180
agtaaatttt cctttatttt tgacaggatt caactggaag ctttgtgctg cctttccggc   18240
aagtcatgta tgctccatat cccaccacac acatagatgt ggatgtcaat actgtgaagc   18300
agatgccacc ctgtcatgaa catatttata atcagcgtag atacatgaga tccgagctga   18360
cagccttctg gagagccact tcagaagaag acatggctca ggatacgatc atctacactg   18420
acgaaagctt tactcctgat ttgtacgtaa tgctctgcct gctggtactg tagtcaagca   18480
atatgaaatt gtgtctttta cgaataaaaa caaaacagaa gttgcattta aaagaaaga   18540 aatattacca gcagaattat gcttgaagaa acatttaatc aagcattttt tcttaaatg   18600 ttcttctttt tccatacaat tgtgtttacc ctaaaatagg taagattaac ccttaaagta   18660
aatatttaac tatttgttta ataaatatat attgagctcc taggcactgt tctaggtacc   18720
gggcttaata gtgccaacc agacagcccc agccccagcc cctacattgt gtatagtcta   18780
ttatgtaaca gttattgaat ggacttatta acaaaaccaa agaagtaatt ctaagtctttt   18840
```

```
tttttcttga catatgaata taaaatacag caaaactgtt aaaatatatt aatggaacat    18900 tttttttactt tgcatttttat attgttattc acttcttatt ttttttttaaa aaaaaaagcc    18960 tgaacagtaa attcaaaagg aaaagtaatg ataattaatt gttgagcatg gacccaactt    19020
gaaaaaaaaa atgatgatga taaatctata atcctaaaac cctaagtaaa cacttaaaag    19080
atgttctgaa atcaggaaaa gaattatagt atactttttgt gtttctcttt tatcagttga    19140
aaaaaggcac agtagctcat gcctgtaaga acagagcttt gggagtgcaa ggcaggcgga    19200
tcacttgagg ccaggagttc cagaccagcc tgggcaacat agtgaaaccc catctctaca    19260
aaaaataaaa aagaattatt ggaatgtgtt tctgtgtgcc tgtaatccta gctattccga    19320
aagctgaggc aggaggatct tttgagccca ggagtttgag gttacaggga gttatgatgt    19380
gccagtgtac tccagcctgg ggaacaccga gactctgtct tatttaaaaa aaaaaaaaaa    19440
aaaatgcttg caataatgcc tggcacatag aaggtaacag taagtgttaa ctgtaataac    19500
ccaggtctaa gtgtgtaagg caatagaaaa attggggcaa ataagcctga cctatgtatc    19560
tacagaatca gtttgagctt aggtaacaga cctgtggagc accagtaatt acacagtaag    19620
tgttaaccaa aagcatagaa taggaatatc ttgttcaagg gaccccccagc cttatacatc    19680 tcaaggtgca gaaagatgac ttaatatagg acccattttt tcctagttct ccagagtttt    19740
tattggttct tgagaaagta gtaggggaat gttttagaaa atgaattggt ccaactgaaa    19800
ttacatgtca gtaagttttt atatattggt aaatttttagt agacatgtag aagttttcta    19860
attaatctgt gccttgaaac atttttcttt ttcctaaagt gcttagtatt ttttccgttt    19920
tttgattggt tacttgggag cttttttgag gaaatttagt gaactgcaga atgggtttgc    19980
aaccatttgg tattttttgtt ttgttttttta gaggatgtat gtgtatttta acatttctta    20040 atcatttttta gccagctatg tttgttttgc tgatttgaca aactacagtt agacagctat    20100
tctcattttg ctgatcatga caaaataata tcctgaattt ttaaattttg catccagctc    20160
taaattttct aaacataaaa ttgtccaaaa aatagtattt tcagccacta gattgtgtgt    20220
taagtctatt gtcacagagt cattttactt ttaagtatat gttttttacat gttaattatg    20280 tttgttattt ttaattttaa ctttttttaaaa taattccagt cactgccaat acatgaaaaa    20340
ttggtcactg gaatttttttt tttgactttt attttaggtt catgtgtaca tgtgcaggtg    20400
tgttatacag gtaaattgcg tgtcatgagg gtttggtgta caggtgattt cattacccag    20460
gtaataagca tagtacccaa taggtagttt tttgatcctc acccttctcc cacccctcaag    20520 taggccctgg tgttgctgtt tccttctttg tgtccatgta tactcagtgt ttagctccca    20580
cttagaagtg agaacatgcg gtagttggtt ttctgttcct ggattagttc acttaggata    20640
atgacctcta gctccatctg gttttttatgg ctgcatagta ttccatggtg tatatgtatc    20700
acattttctt tatccagtct accattgata ggcatttagg ttgattccct gtctttgtta    20760
tcatgaatag tgctgtgatg aacatacaca tgcatgtgtc tttatggtag aaaaatttgt    20820 attccttttag gtacatatag aataatgggg ttgctagggt gaatggtagt tctatttttca    20880 gttatttgag aaatcttcaa actgcttttc ataatagcta aactaattta cagtcccgcc    20940
agcagtgtat aagtgttccc ttttctccac aaccttgcca acatctgtga ttttttgact    21000
ttttaataat agccattcct agagaattga tttgcaattc tctattagtg atattaagca    21060 tttttttcata tgcttttttag ctgtctgtat atattcttct gaaaaatttt catgtccttt    21120
gcccagtttg tagtgggggtg ggttgttttt tgcttgttaa ttagttttaa gttccttcca    21180
gattctgcat atcccttttgt tggatacatg gtttgcagat attttttctcc cattgtgtag    21240
```

```
gttgtcttt  actctgttga  tagtttcttt  tgccatgcag  gagctcgtta  ggtcccattt    21300
gtgtttgttt  ttgttgcagt  tgcttttggc  gtcttcatca  taaaatctgt  gccagggcct    21360
atgtccagaa  tggtatttcc  taggttgtct  tccagggttt  ttacaatttt  agattttacg    21420
tttatgtctt  taatccatct  tgagttgatt  tttgtatatg  gcacaaggaa  ggggtccagt    21480
ttcactccaa  ttcctatggc  tagcaattat  cccagcacca  tttattgaat  acggagtcct    21540
ttccccattg  cttgttttt  gtcaactttg  ttgaagatca  gatggttgta  agtgtgtggc    21600
tttatttctt  ggctctctat  tctccattgg  tctatgtgtc  tgttttata  acagtaccct    21660 gctgttcagg  ttcctatagc  cttttagtat  aaaatcggct  aatgtgatgc  ctccagcttt    21720 gttcttttg  cttaggattg  ctttggctat  ttgggctcct  ttttgggtcc  atattaattt    21780
taaaacagtt  ttttctggtt  ttgtgaagga  tatcattggt  agtttatagg  aatagcattg    21840
aatctgtaga  ttgctttggg  cagtatggcc  attttaacaa  tattaattct  tcctatctat    21900
gaatatggaa  tgttttcca  tgtgtttgtg  tcatctcttt  atacctgatg  tataaagaaa    21960
agctggtatt  attcctactc  aatctgttcc  aaaaaattga  ggaggaggaa  ctcttcccta    22020
atgaggccag  catcattctg  ataccaaaac  ctggcagaga  cacaacagaa  aaagaaaac    22080 ttcaggccaa  tatccttgat  gaatatagat  gcaaaaatcc  tcaacaaaat  actagcaaac    22140
caaatccagc  agcacatcaa  aaagctgatc  tactttgatc  aagtaggctt  tatccctggg    22200
atgcaaggtt  ggttcaacat  acacaaatca  ataagtgtga  ttcatcacat  aaacagagct    22260
aaaaacaaaa  accacaagat  tatctcaata  ggtagagaaa  aggttgtcaa  taaaatttaa    22320
catcctccat  gttaaaaacc  ttcagtaggt  caggtgtagt  gactcacacc  tgtaatccca    22380
gcactttggg  aggccaaggc  gggcatatct  cttaagccca  ggagttcaag  acgagcctag    22440
gcagcatggt  gaaaccccat  ctctacaaaa  aaaaaaaaaa  aaaaaaatta  gcttggtatg    22500
gtgacatgca  cctatagtcc  cagctattca  ggaggttgag  gtgggaggat  tgtttgagcc    22560
cgggaggcag  aggttggcag  cgagctgaga  tcatgccacc  gcactccagc  ctgggcaacg    22620
gagtgagacc  ctgtctcaaa  aagaaaaat  cacaaacaat  cctaaacaaa  ctaggcattg    22680
aaggaacatg  cctcaaaaaa  ataagaacca  tctatgacag  acccatagcc  aatatcttac    22740
caaatgggca  aaagctggaa  gtattctcct  tgagaaccgt  aacaagacaa  ggatgtccac    22800
tctcaccact  ccttttcagc  atagttctgg  aagtcctagc  cagagcaatc  aggaaagaga    22860
aagaaagaaa  gacattcaga  taggaagaga  agaagtcaaa  ctatttctgt  ttgcaggcag    22920
tataattctg  tacctagaaa  atctcatagt  ctctgcccag  aaactcctaa  atctgttaaa    22980
aatttcagca  aagttttggc  attctctata  ctccaacacc  ttccaaagtg  agagcaaaat    23040
caagaacaca  gtcccattca  caatagccgc  aaaacgaata  aaatacctag  gaatccagct    23100
aaccagggag  gtgaaagatc  tctatgagaa  ttacaaaaca  ctgctgaaag  aaatcagaga    23160
tgacacaaac  aaatggaaat  gttctttttt  aacaccttgc  tttatctaat  tcacttatga    23220
tgaagatact  cattcagtgg  aacaggtata  ataagtccac  tcgattaaat  ataagcctta    23280
ttctctttcc  agagcccaag  aagggggcact  atcagtgccc  agtcaataat  gacgaaatgc    23340 taatatttt  ccccttttacg  gtttctttct  tctgtagtgt  ggtacactcg  tttcttaaga    23400
taaggaaact  tgaactacct  tcctgtttgc  ttctacacat  acccattctc  ttttttgcc    23460 actctggtca  ggtataggat  gatccctacc  actttcagtt  aaaaactcct  cctcttacta    23520
aatgttctct  taccctctgg  cctgagtaga  acctaggaa  aatggaagag  aaaaagatga    23580
aagggaggtg  gggcctggga  agggaataag  tagtcctgtt  tgtttgtgtg  tttgctttag    23640
```

```
cacctgctat atcctaggtg ctgtgttagg cacacattat tttaagtggc cattatatta    23700
ctactactca ctctggtcgt tgccaaggta ggtagtactt tcttggatag ttggttcatg    23760
ttacttacag atggtgggct tgttgaggca aacccagtgg ataatcatcg gagtgtgttc    23820
tctaatctca ctcaaatttt tcttcacatt ttttggtttg ttttggtttt tgatggtagt    23880
ggcttatttt tgttgctggt ttgttttttg tttttttttg agatggcaag aattggtagt    23940
tttatttatt aattgcctaa gggtctctac ttttttttaaa agatgagagt agtaaaatag    24000
attgatagat acatacatac ccttactggg gactgcttat attctttaga gaaaaaatta    24060
catattagcc tgacaaacac cagtaaaatg taaatatatc cttgagtaaa taatgaatg     24120 tatattttgt gtctccaaat atatatatct atattcttac aaatgtgttt atatgtaata    24180
tcaatttata agaacttaaa atgttggctc aagtgaggga ttgtggaagg tagcattata    24240
tggccatttc aacatttgaa cttttttctt ttcttcattt tcttctttttc ttcaggaata   24300 tttttcaaga tgtcttacac agagacactc tagtgaaagc cttcctggat caggtaaatg    24360
ttgaacttga gattgtcaga gtgaatgata tgacatgttt tctttttttaa tatatcctac   24420 aatgcctgtt ctatatattt atattcccct ggatcatgcc ccagagttct gctcagcaat    24480
tgcagttaag ttagttacac tacagttctc agaagagtct gtgagggcat gtcaagtgca    24540
tcattacatt ggttgcctct tgtcctagat ttatgcttcg ggaattcaga cctttgttta    24600
caatataata aatattattg ctatctttta aagatataat aataagatat aaagttgacc    24660
acaactactg tttttttgaaa catagaattc ctggtttaca tgtatcaaag tgaaatctga   24720
cttagctttt acagatataa tatatacata tatatatccct gcaatgcttg tactatatat   24780
gtagtacaag tatatatata tgtttgtgtg tgtatatata tatagtacga gcatatatac    24840
atattaccag cattgtagga tatatatatg tttatatatt aaaaaaaagt tataaactta    24900
aaaccctatt atgttatgta gagtatatgt tatatatgat atgtaaaata tataacatat    24960
actctatgat agagtgtaat atattttta tatatatttt aacatttata aaatgataga    25020
attaagaatt gagtcctaat ctgttttatt aggtgctttt tgtagtgtct ggtctttcta    25080
aagtgtctaa atgattttttc cttttgactt attaatgggg aagagcctgt atattaacaa   25140
ttaagagtgc agcattccat acgtcaaaca acaaacattt taattcaagc attaacctat    25200
aacaagtaag tttttttttt tttttgaga aagggaggtt gtttatttgc ctgaaatgac     25260 tcaaaatat ttttgaaaca tagtgtactt atttaaataa catctttatt gtttcattct     25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt tgggagtccg aggtgggtgg    25920
atcacaaggt caggagatcg agaccatcct gccaacatgt gaaacccccg tctctactaa    25980
gtatacaaaa attagctggg cgtggcagcg tgtgcctgta atcccagcta cctgggaggc    26040
```

```
tgaggcagga gaatcgcttg aacccaggag gtgtaggttg cagtgagtca agatcgcgcc    26100
actgcacttt agcctggtga cagagctaga ctccgtctca aaaaaaaaaa aaaatatcag    26160
attgttccta cacctagtgc ttctatacca cactcctgtt aggggggcatc agtggaaatg    26220 gttaaggaga tgtttagtgt gtattgtctg ccaagcactg tcaacactgt catagaaact    26280
tctgtacgag tagaatgtga gcaaattatg tgttgaaatg gttcctctcc ctgcaggtct    26340
ttcagctgaa acctggctta tctctcagaa gtactttcct tgcacagttt ctacttgtcc    26400
ttcacagaaa agccttgaca ctaataaaat atatagaaga cgatacgtga gtaaaactcc    26460 tacacgaag aaaaacccttt gtacattgtt ttttgtttt gtttcctttg tacattttct    26520
atatcataat ttttgcgctt cttttttttt tttttttttt ttttttccca ttattttag    26580 gcagaaggga aaaagccct ttaaatctct tcggaacctg aagatagacc ttgatttaac    26640
agcagagggc gatcttaaca taataatggc tctggctgag aaaattaaac caggcctaca    26700 ctctttatc tttggaagac ctttctacac tagtgtgcaa gaacgagatg ttctaatgac    26760
tttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatctttttaa agatataata ataggatgta aacttgacca    27060
caactactgt ttttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctactttgt ggatttagtc cctgggattc agtctgtaga    27360
aatgtctaat agttctctat agtccttgtt cctggtgaac cacagttagg gtgttttgtt    27420
tattttattg ttcttgctat tgttgatatt ctatgtagtt gagctctgta aaaggaaatt    27480 gtatttatg ttttagtaat tgttgccaac ttttaaatt aattttcatt attttttgagc    27540 caaattgaaa tgtgcacctc ctgtgccttt tttctcctta gaaaatctaa ttacttggaa    27600
caagttcaga tttcactggt cagtcatttt catcttgttt tcttcttgct aagtcttacc    27660
atgtacctgc tttggcaatc attgcaactc tgagattata aaatgcctta gagaatatac    27720
taactaataa gatcttttttt tcagaaacag aaaatagttc cttgagtact tccttcttgc    27780
atttctgcct atgttttga agttgttgct gtttgcctgc aataggctat aaggaatagc    27840
aggagaaatt ttactgaagt gctgttttcc taggtgctac tttggcagag ctaagttatc    27900
ttttgttttc ttaatgcgtt tggaccattt tgctggctat aaaataactg attaatataa    27960
ttctaacaca atgttgacat tgtagttaca caaacacaaa taaatatttt atttaaaatt    28020
ctggaagtaa tataaaaggg aaaatatatt tataagaaag ggataaaggt aatagagccc    28080
ttctgccccc cacccaccaa atttacacaa caaaatgaca tgttcgaatg tgaaaggtca    28140
taatagcttt cccatcatga atcagaaaga tgtggacagc ttgatgtttt agacaaccac    28200
tgaactagat gactgttgta ctgtagctca gtcatttaaa aaatatataa atactacctt    28260
gtagtgtccc atactgtgtt ttttacatgg tagattctta tttaagtgct aactggttat    28320
tttctttggc tggtttattg tactgttata cagaatgtaa gttgtacagt gaaataagtt    28380
attaaagcat gtgtaaacat tgttatatat cttttctcct aaatggagaa ttttgaataa    28440
```

```
aatatatttg aaattttgcc tctttcagtt gttcattcag aaaaaaatac tatgatattt     28500
gaagactgat cagcttctgt tcagctgaca gtcatgctgg atctaaactt tttttaaaat     28560
taattttgtc ttttcaaaga aaaatatttt aaagaagctt tataatataa tcttatgtta     28620
aaaaaacttt ctgcttaact ctctggattt cattttgatt tttcaaatta tatattaata     28680
tttcaaatgt aaaatactat ttagataaat tgttttttaaa cattcttatt attataatat     28740
taatataacc taaactgaag ttattcatcc caggtatcta atacatgtat ccaaagtaaa     28800
aatccaagga atctgaacac tttcatctgc aaagctagga ataggtttga cattttcact     28860
ccaagaaaaa gttttttttt gaaaatagaa tagttgggat gagaggtttc tttaaaagaa     28920
gactaactga tcacattact atgattctca aagaagaaac caaaacttca tataatacta     28980
taaagtaaat ataaaatagt tccttctata gtatatttct ataatgctac agtttaaaca     29040
gatcactctt atataatact attttgattt tgatgtagaa ttgcacaaat tgatatttct     29100
cctatgatct gcagggtata gcttaaagta acaaaaacag tcaaccacct ccatttaaca     29160
cacagtaaca ctatgggact agttttatta cttccatttt acaaatgagg aaactaaagc     29220
ttaaagatgt gtaatacacc gcccaaggtc acacagctgg taaaggtgga tttcatccca     29280
gacagttaca gtcattgcca tgggcacagc tcctaactta gtaactccat gtaactggta     29340
ctcagtgtag ctgaattgaa aggagagtaa ggaagcaggt tttacaggtc tacttgcact     29400
attcagagcc cgagtgtgaa tccctgctgt gctgcttgga gaagttactt aacctatgca     29460
aggttcattt tgtaaatatt ggaaatggag tgataatacg tacttcacca gaggatttaa     29520
tgagacctta tacgatcctt agttcagtac ctgactagtg cttcataaat gctttttcat     29580
ccaatctgac aatctccagc ttgtaattgg ggcatttaga acatttaata tgattattgg     29640
catggtaggt taaagctgtc atcttgctgt tttctatttg ttcttttttgt tttctcctta     29700 cttttggatt ttttttattct actatgtctt ttctattgtc ttattaacta tactctttga     29760
tttattttag tggttgtttt agggttatac ctctttctaa tttaccagtt tataaccagt     29820
ttatatacta cttgacatat agcttaagaa acttactgtt gttgtctttt tgctgttatg     29880
gtcttaacgt ttttatttct acaaacatta taaactccac actttattgt tttttaattt     29940
tacttataca gtcaattatc ttttaaagat atttaaatat aaacattcaa aacaccccaa     30000
t                                                                    30001
```

<210> SEQ ID NO 3
<211> LENGTH: 1031
<212> TYPE: DNA
<213> ORGANISM: Homo sapiens

<400> SEQUENCE: 3

```
attcccggga tacgtaacct acggtgtccc gctaggaaag agaggtgcgt caaacagcga      60
caagttccgc ccacgtaaaa gatgacgctt ggtgtgtcag ccgtccctgc tgcccggttg     120
cttctctttt gggggcgggg tctagcaaga gcaggtgtgg gttaggagaa tatctccgga     180
gcatttggat aatgtgacag ttggaatgca gtgatgtcga ctctttgccc accgccatct     240
ccagctgttg ccaagacaga gattgcttta agtggcaaat caccttttatt agcagctact     300 tttgcttact gggacaatat tcttggtcct agagtaaggc acatttgggc tccaaagaca     360
gaacaggtac ttctcagtga tggagaaata acttttcttg ccaaccacac tctaaatgga     420
gaaatccttc gaaatgcaga gagtggtgct atagatgtaa agtttttttgt cttgtctgaa     480 aagggagtga ttattgtttc attaatcttt gatggaaact ggaatgggga tcgcagcaca     540
```

-continued

```
tatggactat caattatact tccacagaca gaacttagtt tctacctccc acttcatgaga    600
gtgtgtgttg atagattaac acatataatc cggaaaggaa gaatatggat gcataaggaa    660
agacaagaaa aatgtccaga agattatctt agaaggcaca gagagaatgg aagatcaggg    720
tcagagtatt attccaatgc ttactggaga agtgattcct gtaatggaaa ctgctttcct    780
ctatgaaatt ccccgggtt cctggaggaa atagatatag gctgatacag ttacccaatg    840
atggatgaat attgggggac cgcctggtca ttgaaaggct ttcttttctc caggaaagaa    900
atttttttcc ttttccataa aaagcttggg aatggaagac aacaattccc attcttttt    960
tgcgttccac ccctatgtga acacagaaat ttttggggaa acaacaacga aaaattta   1020
tcccgcgcgc a                                                      1031
```

<210> SEQ ID NO 4
<211> LENGTH: 3244
<212> TYPE: DNA
<213> ORGANISM: Homo sapiens
<220> FEATURE:
<221> NAME/KEY: CDS
<222> LOCATION: (108)..(1553)

<400> SEQUENCE: 4

```
gggcggggct gcggttgcgg tgcctgcgcc cgcggcggcg gaggcgcagg cggtggcgag     60
tggatatctc cggagcattt ggataatgtg acagttggaa tgcagtg atg tcg act      116
                                                    Met Ser Thr
                                                      1 ctt tgc cca ccg cca tct cca gct gtt gcc aag aca gag att gct tta     164
Leu Cys Pro Pro Pro Ser Pro Ala Val Ala Lys Thr Glu Ile Ala Leu
  5                  10                  15 agt ggc aaa tca cct tta tta gca gct act ttt gct tac tgg gac aat     212
Ser Gly Lys Ser Pro Leu Leu Ala Ala Thr Phe Ala Tyr Trp Asp Asn
 20                  25                  30                  35 att ctt ggt cct aga gta agg cac att tgg gct cca aag aca gaa cag     260
Ile Leu Gly Pro Arg Val Arg His Ile Trp Ala Pro Lys Thr Glu Gln
         40                  45                  50 gta ctt ctc agt gat gga gaa ata act ttt ctt gcc aac cac act cta     308
Val Leu Leu Ser Asp Gly Glu Ile Thr Phe Leu Ala Asn His Thr Leu
     55                  60                  65 aat gga gaa atc ctt cga aat gca gag agt ggt gct ata gat gta aag     356
Asn Gly Glu Ile Leu Arg Asn Ala Glu Ser Gly Ala Ile Asp Val Lys
 70                  75                  80 ttt ttt gtc ttg tct gaa aag gga gtg att att gtt tca tta atc ttt     404
Phe Phe Val Leu Ser Glu Lys Gly Val Ile Ile Val Ser Leu Ile Phe
 85                  90                  95 gat gga aac tgg aat ggg gat cgc agc aca tat gga cta tca att ata     452
Asp Gly Asn Trp Asn Gly Asp Arg Ser Thr Tyr Gly Leu Ser Ile Ile
100                 105                 110                 115 ctt cca cag aca gaa ctt agt ttc tac ctc cca ctt cat aga gtg tgt     500
Leu Pro Gln Thr Glu Leu Ser Phe Tyr Leu Pro Leu His Arg Val Cys
             120                 125                 130 gtt gat aga tta aca cat ata atc cgg aaa gga aga ata tgg atg cat     548
Val Asp Arg Leu Thr His Ile Ile Arg Lys Gly Arg Ile Trp Met His
         135                 140                 145 aag gaa aga caa gaa aat gtc cag aag att atc tta gaa ggc aca gag     596
Lys Glu Arg Gln Glu Asn Val Gln Lys Ile Ile Leu Glu Gly Thr Glu
     150                 155                 160 aga atg gaa gat cag ggt cag agt att att cca atg ctt act gga gaa     644
Arg Met Glu Asp Gln Gly Gln Ser Ile Ile Pro Met Leu Thr Gly Glu
165                 170                 175
```

```
gtg att cct gta atg gaa ctg ctt tca tct atg aaa tca cac agt gtt      692
Val Ile Pro Val Met Glu Leu Leu Ser Ser Met Lys Ser His Ser Val
180             185                 190                 195 cct gaa gaa ata gat ata gct gat aca gta ctc aat gat gat gat att      740
Pro Glu Glu Ile Asp Ile Ala Asp Thr Val Leu Asn Asp Asp Asp Ile
        200                 205                 210 ggt gac agc tgt cat gaa ggc ttt ctt ctc aat gcc atc agc tca cac      788
Gly Asp Ser Cys His Glu Gly Phe Leu Leu Asn Ala Ile Ser Ser His
            215                 220                 225 ttg caa acc tgt ggc tgt tcc gta gta ggt agc agt gca gag aaa          836
Leu Gln Thr Cys Gly Cys Ser Val Val Gly Ser Ser Ala Glu Lys
        230                 235                 240 gta aat aag ata gtc aga aca tta tgc ctt ttt ctg act cca gca gag      884
Val Asn Lys Ile Val Arg Thr Leu Cys Leu Phe Leu Thr Pro Ala Glu
245                 250                 255 aga aaa tgc tcc agg tta tgt gaa gca gaa tca tca ttt aaa tat gag      932
Arg Lys Cys Ser Arg Leu Cys Glu Ala Glu Ser Ser Phe Lys Tyr Glu
260                 265                 270                 275 tca ggg ctc ttt gta caa ggc ctg cta aag gat tca act gga agc ttt      980
Ser Gly Leu Phe Val Gln Gly Leu Leu Lys Asp Ser Thr Gly Ser Phe
                280                 285                 290 gtg ctg cct ttc cgg caa gtc atg tat gct cca tat ccc acc aca cac     1028
Val Leu Pro Phe Arg Gln Val Met Tyr Ala Pro Tyr Pro Thr Thr His
            295                 300                 305 ata gat gtg gat gtc aat act gtg aag cag atg cca ccc tgt cat gaa     1076
Ile Asp Val Asp Val Asn Thr Val Lys Gln Met Pro Pro Cys His Glu
        310                 315                 320 cat att tat aat cag cgt aga tac atg aga tcc gag ctg aca gcc ttc     1124
His Ile Tyr Asn Gln Arg Arg Tyr Met Arg Ser Glu Leu Thr Ala Phe
325                 330                 335 tgg aga gcc act tca gaa gaa gac atg gct cag gat acg atc atc tac     1172
Trp Arg Ala Thr Ser Glu Glu Asp Met Ala Gln Asp Thr Ile Ile Tyr
340                 345                 350                 355 act gac gaa agc ttt act cct gat ttg aat att ttt caa gat gtc tta     1220
Thr Asp Glu Ser Phe Thr Pro Asp Leu Asn Ile Phe Gln Asp Val Leu
                360                 365                 370 cac aga gac act cta gtg aaa gcc ttc ctg gat cag gtc ttt cag ctg     1268
His Arg Asp Thr Leu Val Lys Ala Phe Leu Asp Gln Val Phe Gln Leu
            375                 380                 385 aaa cct ggc tta tct ctc aga agt act ttc ctt gca cag ttt cta ctt     1316
Lys Pro Gly Leu Ser Leu Arg Ser Thr Phe Leu Ala Gln Phe Leu Leu
        390                 395                 400 gtc ctt cac aga aaa gcc ttg aca cta ata aaa tat ata gaa gac gat     1364
Val Leu His Arg Lys Ala Leu Thr Leu Ile Lys Tyr Ile Glu Asp Asp
405                 410                 415 acg cag aag gga aaa aag ccc ttt aaa tct ctt cgg aac ctg aag ata     1412
Thr Gln Lys Gly Lys Lys Pro Phe Lys Ser Leu Arg Asn Leu Lys Ile
420                 425                 430                 435 gac ctt gat tta aca gca gag ggc gat ctt aac ata ata atg gct ctg     1460
Asp Leu Asp Leu Thr Ala Glu Gly Asp Leu Asn Ile Ile Met Ala Leu
                440                 445                 450 gct gag aaa att aaa cca ggc cta cac tct ttt atc ttt gga aga cct     1508
Ala Glu Lys Ile Lys Pro Gly Leu His Ser Phe Ile Phe Gly Arg Pro
            455                 460                 465 ttc tac act agt gtg caa gaa cga gat gtt cta atg act ttt taa         1553
Phe Tyr Thr Ser Val Gln Glu Arg Asp Val Leu Met Thr Phe
        470                 475                 480 atgtgtaact taataagcct attccatcac aatcatgatc gctggtaaag tagctcagtg   1613
gtgtggggaa acgttcccct ggatcatact ccagaattct gctctcagca attgcagtta  1673
```

| | |
|---|---|
| agtaagttac actacagttc tcacaagagc ctgtgagggg atgtcaggtg catcattaca | 1733 |
| ttgggtgtct cttttcctag atttatgctt ttgggataca gacctatgtt tacaatataa | 1793 |
| taaatattat tgctatcttt taaagatata ataataggat gtaaacttga ccacaactac | 1853 |
| tgttttttg aaatacatga ttcatggttt acatgtgtca aggtgaaatc tgagttggct | 1913 |
| tttacagata gttgactttc tatcttttgg cattctttgg tgtgtagaat tactgtaata | 1973 |
| cttctgcaat caactgaaaa ctagagcctt taaatgattt caattccaca gaaagaaagt | 2033 |
| gagcttgaac ataggatgag ctttagaaag aaaattgatc aagcagatgt ttaattggaa | 2093 |
| ttgattatta gatcctactt tgtggattta gtccctggga ttcagtctgt agaaatgtct | 2153 |
| aatagttctc tatagtcctt gttcctggtg aaccacagtt agggtgtttt gtttatttta | 2213 |
| ttgttcttgc tattgttgat attctatgta gttgagctct gtaaaaggaa attgtatttt | 2273 |
| atgttttagt aattgttgcc aacttttaa attaattttc attattttg agccaaattg | 2333 |
| aaatgtgcac ctcctgtgcc ttttttctcc ttagaaaatc taattacttg gaacaagttc | 2393 |
| agatttcact ggtcagtcat tttcatcttg ttttcttctt gctaagtctt accatgtacc | 2453 |
| tgctttggca atcattgcaa ctctgagatt ataaaatgcc ttagagaata tactaactaa | 2513 |
| taagatcttt ttttcagaaa cagaaaatag ttccttgagt acttccttct tgcatttctg | 2573 |
| cctatgtttt tgaagttgtt gctgtttgcc tgcaataggc tataaggaat agcaggagaa | 2633 |
| attttactga agtgctgttt tcctaggtgc tactttggca gagctaagtt atcttttgtt | 2693 |
| ttcttaatgc gtttggacca ttttgctggc tataaaataa ctgattaata taattctaac | 2753 |
| acaatgttga cattgtagtt acacaaacac aaataaatat tttatttaaa attctggaag | 2813 |
| taatataaaa gggaaaatat atttataaga aagggataaa ggtaatagag cccttctgcc | 2873 |
| ccccacccac caaatttaca caacaaatg acatgttcga atgtgaaagg tcataatagc | 2933 |
| tttcccatca tgaatcagaa agatgtggac agcttgatgt tttagacaac cactgaacta | 2993 |
| gatgactgtt gtactgtagc tcagtcattt aaaaaatata taaatactac cttgtagtgt | 3053 |
| cccatactgt gttttttaca tggtagattc ttatttaagt gctaactggt tatttctttt | 3113 |
| ggctggttta ttgtactgtt atacagaatg taagttgtac agtgaaataa gttattaaag | 3173 |
| catgtgtaaa cattgttata tatctttct cctaaatgga gaattttgaa taaaatatat | 3233 |
| ttgaaatttt g | 3244 |

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

| | |
|---|---|
| cacgaggctt tgatatttct tacaacgaat ttcatgtgta gacccactaa acagaagcta | 60 |
| taaaagttgc atggtcaaat aagtctgaga aagtctgcag atgatataat tcacctgaag | 120 |
| agtcacagta tgtagccaaa tgttaaaggt tttgagatgc catacagtaa atttaccaag | 180 |
| cattttctaa atttatttga ccacagaatc cctattttaa gcaacaactg ttacatccca | 240 |
| tggattccag gtgactaaag aatacttatt tcttaggata tgttttattg ataataacaa | 300 |

```
ttaaaatttc agatatcttt cataagcaaa tcagtggtct ttttacttca tgttttaatg      360
ctaaaatatt ttcttttata gatagtcaga acattatgcc ttttctgac tccagcagag       420 agaaaatgct ccaggttatg tgaagcagaa tcatcattta aatatgagtc agggctcttt     480
gtacaaggcc tgctaaagga ttcaactgga agctttgtgc tgccttccg gcaagtcatg      540 tatgctccat atcccaccac acacatagat gtggatgtca atactgtgaa gcagatgcca    600
ccctgtcatg aacatattta taatcagcgt agatacatga gatccgagct gacagccttc    660
tggagagcca cttcagaaga agacatggct cangatacga tcatctacac tgacgaaagc    720
tntactcctg atttgaatat ttttcaagat gtcttacaca g                         761

<210> SEQ ID NO 6
<211> LENGTH: 1901
<212> TYPE: DNA
<213> ORGANISM: Homo sapiens
<220> FEATURE:
<221> NAME/KEY: CDS
<222> LOCATION: (125)..(793)

<400> SEQUENCE: 6
acgtaaccta cggtgtcccg ctaggaaaga gaggtgcgtc aaacagcgac aagttccgcc    60
cacgtaaaag atgacgcttg atatctccgg agcatttgga taatgtgaca gttggaatgc   120 agtg atg tcg act ctt tgc cca ccg cca tct cca gct gtt gcc aag aca    169
     Met Ser Thr Leu Cys Pro Pro Pro Ser Pro Ala Val Ala Lys Thr
     1               5                   10                  15 gag att gct tta agt ggc aaa tca cct tta tta gca gct act ttt gct    217
Glu Ile Ala Leu Ser Gly Lys Ser Pro Leu Leu Ala Ala Thr Phe Ala
             20                  25                  30 tac tgg gac aat att ctt ggt cct aga gta agg cac att tgg gct cca    265
Tyr Trp Asp Asn Ile Leu Gly Pro Arg Val Arg His Ile Trp Ala Pro
         35                  40                  45 aag aca gaa cag gta ctt ctc agt gat gga gaa ata act ttt ctt gcc    313
Lys Thr Glu Gln Val Leu Leu Ser Asp Gly Glu Ile Thr Phe Leu Ala
     50                  55                  60 aac cac act cta aat gga gaa atc ctt cga aat gca gag agt ggt gct    361
Asn His Thr Leu Asn Gly Glu Ile Leu Arg Asn Ala Glu Ser Gly Ala
 65                  70                  75 ata gat gta aag ttt ttt gtc ttg tct gaa aag gga gtg att att gtt    409
Ile Asp Val Lys Phe Phe Val Leu Ser Glu Lys Gly Val Ile Ile Val
 80                  85                  90                  95 tca tta atc ttt gat gga aac tgg aat ggg gat cgc agc aca tat gga    457
Ser Leu Ile Phe Asp Gly Asn Trp Asn Gly Asp Arg Ser Thr Tyr Gly
                 100                 105                 110 cta tca att ata ctt cca cag aca gaa ctt agt ttc tac ctc cca ctt    505
Leu Ser Ile Ile Leu Pro Gln Thr Glu Leu Ser Phe Tyr Leu Pro Leu
             115                 120                 125 cat aga gtg tgt gtt gat aga tta aca cat ata atc cgg aaa gga aga    553
His Arg Val Cys Val Asp Arg Leu Thr His Ile Ile Arg Lys Gly Arg
         130                 135                 140 ata tgg atg cat aag gaa aga caa gaa aat gtc cag aag att atc tta    601
Ile Trp Met His Lys Glu Arg Gln Glu Asn Val Gln Lys Ile Ile Leu
     145                 150                 155 gaa ggc aca gag aga atg gaa gat cag ggt cag agt att att cca atg    649
Glu Gly Thr Glu Arg Met Glu Asp Gln Gly Gln Ser Ile Ile Pro Met
 160                 165                 170                 175 ctt act gga gaa gtg att cct gta atg gaa ctg ctt tca tct atg aaa    697
Leu Thr Gly Glu Val Ile Pro Val Met Glu Leu Leu Ser Ser Met Lys
                 180                 185                 190
```

-continued

| | | |
|---|---|---|
| tca cac agt gtt cct gaa gaa ata gat ata gct gat aca gta ctc aat<br>Ser His Ser Val Pro Glu Glu Ile Asp Ile Ala Asp Thr Val Leu Asn<br>                195                        200                      205 | 745 |
| gat gat gat att ggt gac agc tgt cat gaa ggc ttt ctt ctc aag taa<br>Asp Asp Asp Ile Gly Asp Ser Cys His Glu Gly Phe Leu Leu Lys<br>                210                        215                      220 | 793 |
| gaatttttct tttcataaaa gctggatgaa gcagatacca tcttatgctc acctatgaca | 853 |
| agatttggaa gaaagaaaat aacagactgt ctacttagat tgttctaggg acattacgta | 913 |
| tttgaactgt tgcttaaatt tgtgttattt ttcactcatt atatttctat atatatttgg | 973 |
| tgttattcca tttgctattt aaagaaaccg agtttccatc ccagacaaga aatcatggcc | 1033 |
| ccttgcttga ttctggtttc ttgttttact tctcattaaa gctaacagaa tcctttcata | 1093 |
| ttaagttgta ctgtagatga acttaagtta tttaggcgta gaacaaaatt attcatattt | 1153 |
| atactgatct ttttccatcc agcagtggag tttagtactt aagagtttgt gcccttaaac | 1213 |
| cagactccct ggattaatgc tgtgtacccg tgggcaaggt gcctgaattc tctatacacc | 1273 |
| tatttcctca tctgtaaaat ggcaataata gtaatagtac ctaatgtgta gggttgttat | 1333 |
| aagcattgag taagataaat aatataaagc acttagaaca gtgcctggaa cataaaaaca | 1393 |
| cttaataata gctcatagct aacatttcct atttacattt cttctagaaa tagccagtat | 1453 |
| ttgttgagtg cctacatgtt agttccttta ctagttgctt tacatgtatt atcttatatt | 1513 |
| ctgttttaaa gttcttcac agttacagat tttcatgaaa ttttactttt aataaaagag | 1573 |
| aagtaaaagt ataaagtatt cacttttatg ttcacagtct tttcctttag gctcatgatg | 1633 |
| gagtatcaga ggcatgagtg tgtttaacct aagagcctta atggcttgaa tcagaagcac | 1693 |
| tttagtcctg tatctgttca gtgtcagcct ttcatacatc attttaaatc ccatttgact | 1753 |
| ttaagtaagt cacttaatct ctctacatgt caatttcttc agctataaaa tgatggtatt | 1813 |
| tcaataaata aatacattaa ttaaatgata ttatactgac taattgggct gttttaaggc | 1873 |
| aaaaaaaaaa aaaaaaaaa aaaaaaaa | 1901 |

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

| | |
|---|---|
| agacgtaacc tacggtgtcc cgctaggaaa gagagatatc tccggagcat ttggataatg | 60 |
| tgacagttgg aatgcagtga tgtcgactct ttgcccaccg ccatctccag ctgttgccaa | 120 |
| gacagagatt gctttaagtg gcaaatcacc tttattagca gctacntttt gcttactggg | 180 |
| acaatattct tggtcctaga gtaaggcaca tttgggctcc aaagacagaa caggtacttc | 240 |
| tcagtgatgg agaaataact tttcttgcca accacactct aaatggagaa atccttcgaa | 300 |
| atgcagagag tggtgctata gatgtaaagt tttttgtctt gtctgaaaag ggagtgatta | 360 |
| ttgtttcatt aatctttgat ggaaactgga atggggatcg cagcacatat ggactatcaa | 420 |
| ttatacttcc acagacagaa cttagtttct acctcccact tcatagagtg tgtgttgata | 480 |
| gattaacaca tataatccgg aaaggaagaa tatggatgca taaggaaaga caagaaaatg | 540 |
| tccagaagat tatcttagaa gg | 562 |

<210> SEQ ID NO 8
<211> LENGTH: 798
<212> TYPE: DNA
<213> ORGANISM: Homo sapiens
<220> FEATURE:
<221> NAME/KEY: CDS
<222> LOCATION: (81)..(590)

<400> SEQUENCE: 8

```
gggctctctt tgggggcgg ggtctagcaa gagcagatat ctccggagca tttggataat      60
gtgacagttg gaatgcagtg atg tcg act ctt tgc cca ccg cca tct cca gct    113
                     Met Ser Thr Leu Cys Pro Pro Pro Ser Pro Ala
                       1               5                  10 gtt gcc aag aca gag att gct tta agt ggc aaa tca cct tta tta gca      161
Val Ala Lys Thr Glu Ile Ala Leu Ser Gly Lys Ser Pro Leu Leu Ala
             15                  20                  25 gct act ttt gct tac tgg gac aat att ctt ggt cct aga gta agg cac      209
Ala Thr Phe Ala Tyr Trp Asp Asn Ile Leu Gly Pro Arg Val Arg His
         30                  35                  40 att tgg gct cca aag aca gaa cag gta ctt ctc agt gat gga gaa ata      257
Ile Trp Ala Pro Lys Thr Glu Gln Val Leu Leu Ser Asp Gly Glu Ile
     45                  50                  55 act ttt ctt gcc aac cac act cta aat gga gaa atc ctt cga aat gca      305
Thr Phe Leu Ala Asn His Thr Leu Asn Gly Glu Ile Leu Arg Asn Ala
 60                  65                  70                  75 gag agt ggt gct ata gat gta aag ttt ttt gtc ttg tct gaa aag gga      353
Glu Ser Gly Ala Ile Asp Val Lys Phe Phe Val Leu Ser Glu Lys Gly
                 80                  85                  90 gtg att att gtt tca tta atc ttt gat gga aac tgg aat ggg gat cgc      401
Val Ile Ile Val Ser Leu Ile Phe Asp Gly Asn Trp Asn Gly Asp Arg
             95                 100                 105 agc aca tat gga cta tca att ata ctt cca cag aca gaa ctt agt ttc      449
Ser Thr Tyr Gly Leu Ser Ile Ile Leu Pro Gln Thr Glu Leu Ser Phe
         110                 115                 120 tac ctc cca ctt cat aga gtg tgt gtt gat aga tta aca cat ata atc      497
Tyr Leu Pro Leu His Arg Val Cys Val Asp Arg Leu Thr His Ile Ile
     125                 130                 135 cgg aaa gga aga ata tgg atg cat aag gaa aga caa gaa aat gtc cag      545
Arg Lys Gly Arg Ile Trp Met His Lys Glu Arg Gln Glu Asn Val Gln
140                 145                 150                 155 aag att atc tta gaa ggc aca gag aga atg gaa gat cag ggt cag         590
Lys Ile Ile Leu Glu Gly Thr Glu Arg Met Glu Asp Gln Gly Gln
                 160                 165                 170 agtattattc caatgcttac tggagaagtg attcctgtaa tgggactgct ttcatctatg    650
aaatcacaca gtgttcctga agaaatagat atagctgata cagtactcca tgatgatgat    710
atttggtgac agctgtcatg aaaggctttc ttctcaagta ggaatttttt cttttcataa    770
aagctgggat gaagccagat tcccatct                                      798
```

<210> SEQ ID NO 9
<211> LENGTH: 169
<212> TYPE: DNA
<213> ORGANISM: Homo sapiens

<400> SEQUENCE: 9

```
aaacagcgac aagttccgcc cacgtaaaag atgatgcttg gtgtgtcagc cgtccctgct      60
gcccggttgc ttctcttttg ggggcggggt ctagcaagag cagatatctc cggagcattt    120
ggataatgtg acagttggaa tgcggtgatg tcgactcttt gcccaccgc                 169
```

```
<210> SEQ ID NO 10
<211> LENGTH: 176
<212> TYPE: DNA
<213> ORGANISM: Homo sapiens

<400> SEQUENCE: 10
aaaacgtcat cgcacataga aaacagacag acgtaaccta cggtgtcccg ctaggaaaga    60
gaggtgcgtc aaacagcgac aagttccgcc cacgtaaaag atgacgcttg atatctccgg   120
agcatttgga taatgtgaca gttggaatgc agtgatgtcg actctttgcc caccgc       176

<210> SEQ ID NO 11
<211> LENGTH: 38001
<212> TYPE: DNA
<213> ORGANISM: Mus musculus

<400> SEQUENCE: 11
caaacacaca cacacacaca cacacacaca cacacacaca cacacacaca cacacactgg    60
catatcaagt ctctgttagg ctaggcgcat cctctcccac tgaggtcaga caagactgcc   120
cagctagaag aacatatccc acggacaggc aacagctttt gggacagcca cgctccagtt   180
gtttgggact cataaaagac taaactcaca cctgctacaa aagtgcaggg aggcctaggt   240
ccagcctgtg tgtgctcttt gcttagtggt gtctctgaga gccctaagga tcaaagtttg   300
ttgactctgt tggtcttcct gtggagttcc tatcccttc gtcccctcc ccaccctgca    360 atctttccct caactcttct ttaggcctgg tggtggtggt gtggtggcat ggaggaggtg   420
gtggaggggg tggggtctt taatcccggt tcttgtgaga ccgaagcagg gacgatttcg   480
gagctctgtg agtttgaggc cagcctggtc tatagatcta gttccaggac agtcagagct   540
acatagagaa accctgcccc gagggggggg gggcgcgggg aatggttaaa gattattgca   600
ggacccagct gatctgtgga agaggtaacg ggtgtttatg ttttcgaaa ctcattgaac    660 aatgcacttc aattgtgcgc actttagaaa tataaagcca ccacgcgaaa agctgcgccc   720
caacttaaag gcaatttcca aggtacttct gggtccttgc ggttcagtgg ctgtctaggt   780
tcagaaacga aactggatcc ccgccccgcc ccccgcccc ccccctcccc agcgccctga    840
ggcagtttcg atttcctatg gccagccggc taggcagctt tttcatcggg actccttgga   900
aagtccccac ttcgttcatc tctggcggat ttgcgggagc cagggcgctc atcgatcgcc   960
tggagccaca gaatgacagc ggagcagcgg cagaatctgc aagcattcag agactatatc  1020
aagaagattc tggaccccac ctacatcctc agctacatga gttcctggct cgaggatggt  1080
gagtggtccc caactggggc tctcaggctc tccaccttag cgaggggaaa acatcactca  1140
gatcagaaac aattgaaggc tctgcccccc ccctccccc gcgctgtcct taagttaatt   1200
tgtgtaaccc ggtgtatgtg agactcccag gccatattag agtagacagc atagggattt  1260
gatggtcagg aacaaaattc ctgcaagctg tagtaacttg cataaggatg ccactctttt  1320
ctttctttca atgctgggga aatagtttgt ttctcttatt tacaccttct agactgctgt  1380
gtgcctccct ttgtcctgtc atgagaaact gagaaatcag aatgcgcccg cccctcctta  1440
gattcctgta cagagcaaag agcaaggctt ggggctcggg ccaaaggtgg aggtgggggc  1500
cgcaggaagc aagaggactg actgacacgc acatttctgt caaaggatgt tgctcacagg  1560
aagtccgtgg aagaaaactt tctccagact ccgtgtgttc agagtttaac acagttgttc  1620
atatctagct ttggggattt gattggtgga taatagactc tttgtaaatt gcactgggtg  1680
tttccacctg agcaaacaga cctccccacc tcaccccac ccccagggag aagggagagg   1740
```

```
gcgtttgaag gggtgaccga gggcgtgcgg cagctacttt tcattttgcc agttaaagcc    1800
tagatgtctt tcctggcgtt ggacgacggt ggcaactgca ggttaattct gactctcttg    1860
agttccgaag cctaacaggc tatgcagaga ggagtaaaag agcactaccc agggctaccc    1920
acatcccggt tgtgttagag agaagcagca aaaaagccct aatgattggg ggcggggtct    1980
gaggagagga aacccaccca agaggtttct taacaccagg gtcacttgcc tttcaatcct    2040
ttaatctgat ctttagtcat ttacattagc atacaaagta actagtttca atactgaaac    2100
aaagtaacta gtttgttcag ccattcctgc cattgctctt tgttcttatt taattgcctc    2160
ttctgtggct cttccacccc ctttacctgt ccctctctgg atgccctccc ccccaaatgg    2220
taccccgttc tgctttctta aacatgagg ttcatcacac tccctccctc cctccctccc     2280
ccatttaaag tatcatcctt tcctctcagg gtgcctgttt tagtttcatg aattttaggg    2340
ttttggtttt ttgtctgttt agttatgaga tttttttaaa aatgtggatt atgttgaatt    2400
tgtagattgt tcttggtgct agaggccttt ttatagtatt atttccaccc atcttgggag    2460
atctttctga aatcttccag tgtcttcaag aattttttt  tcccactgcc ttagaagttt    2520
gcattgtagc tatcgttcac ctcttttggtt agggtttgtt gttatttgtt tgtttgaggc    2580
tattgtgaat agaactccct ccttccccca tatctttctg ggccaggttg ttcttagtat    2640
gtaagtaagc tactggtttc tgtatgttta tttagaaccc tgcctcttgg ttgactttt     2700
atgagggctg agagtttgtg gtagtctttg gggggtcttt ataggattat ataagaatca    2760
tttgactcat tcctttccta tttgtctaac ttttgtttgt ttgtttgttt gtttttttga    2820
gacagggttt ctctgtatag ccctggcagt cctggaactc actttgtaga ccaggctggc    2880
ctcgaactca gaaatctgcc tgcctctgcc tcccgagtgc tgggattaaa ggcgtgcacc    2940
accacacccg gccatcattt ccaagttaaa gatttgatct acattagacg ccgccacgca    3000
gaaaaccttg agacttggtg gaaaggccaa aggccattaa aataaatttt cttttttctt    3060
tcttccattc tttcctttat tccttccttc ctttctttt  gttttctttc ttttcttttt    3120
cctttttcct gagacagggt ttctctgtat agccctggca tcctggaact cactctgtag    3180
accaggctgg cctcgaactc agaaatccac cagcctttgc ctcccaagtg ttgggattaa    3240
aggcattcgc caccactgcc caaatatttt atttatttat ttatttattt attttatat     3300
atgtgatgag tacactggaa attccatcaa aaagagcagg tttgactggt gtcactagat    3360
ttactattga tagggatccc taaaggagag ctaaggtaaa gggctctccc tctcctaggt    3420
cttctgcata ccttccttga gtgttctggg ccagatctcc taagctctaa gaatgtgctg    3480
aaaacacact gggaactggc tccctccttg ggaatttgta ctccctctgc tgtgggaaac    3540
ttggatataa gaggctacag gaggacagtg agttataccc caggcacaga gttagcgtgt    3600
acattcaaaa cgcataccat tttgaaagta gcagctgcta gcatttcctg tcacctggtc    3660
aacctggtct ctttagctgc cccaccccTt ccacttttct gctgtgtttc ttttactctc    3720
ttagcaaaaa ttggaatgaa agaccacaaa tgtatttgta attcaaaatg cttgctgcat    3780
cagctatact cgttactgtt gccataggc gttcattccc acccacccccc aacccccttag    3840
tccagcagtt gctcagagt tttgaagaag aggaggaagc ctttcttctt ccatgtgaca     3900
ccctccactg cgacttctgc ttactgtggg gaacttgagt ggaggacggg agtgtgcata    3960
gatgaaagag tggaggacgg gagtgtgcat agatgaagga gtggaggacg ggagtgtgca    4020
tacatgaagg agtggaggac gggagtgtgc atacatgaag gagtggagga cgggagtgtg    4080
catacatgaa ggagtggagg acgggagtgt gcatacatga aggagtggag gatgggagtg    4140
```

```
tgcatacatg aaggagtgga ggacgggagt gtgcatacat gaaggagtgg aggacgggag      4200
tgtgcataca tgaaggagag gaggacggga gtgtgcatag atgaaggaga ggaggacggg      4260
agtgtgcata gatgaaggag aggaggacgg gagtgtgcat agatgaagga gaggaggacg      4320
ggagtgtgca tagatgaagg agaggaggac gggagtgtgc atagatgaag gagtggagga      4380
cgggagtgtg catacatgaa ggagtggagg acgggagtgt gcatacatga aggagtggag      4440
gacgggagtg tgcatacatg aaggagtgga ggacgggagt gtgcatacat gaaggagtgg      4500
aggacgggag tgtgcataca tgaaggagag gaggacggga gtgtgcatag atgaaggaga      4560
ggaggacggg agtgtgcata gatgaaggag aggaggacgg gagtgtgcat agatgaagga      4620
gaggaggacg ggagtgtgca tacatgaagg aaaggaggac gggagtgtgc atagatgaag      4680
gagtggagga cgggagtgtg catacatgaa ggagtggagg acgggagtgt gcatacatga      4740
aggagtggag gacgggagtg tgcatatgaa ggagtggagg acgggagtgt gcatacatga      4800
aggagtggag gacgggagtg tgcatagatg aaggagagga ggacgggagt gtgcatagat      4860
gaaggagagg aggacgggag agtgcataga tgaaggagtg gaggacggga gtgtgcatac      4920
atgaaggagt ggaggacggg agtgtgcata catgaaggag tggaggacgg gagtgtgcat      4980
agatgaagga gaggaggacg ggagtgtgca tagatgaagg agaggaggac gggagagtgc      5040
atagatgaag gagtggagga cgggagtgtg catagatgaa ggagtggagg acgagagtgt      5100
gcatacatga aggagtggag gacgggagtg tgcgaggatg gatgagtgga gtctgctgcc      5160
tctcaaaggt cttctggttc catgagttgt tatgactccc agacccacat gggaaggtct      5220
ggtctgttat cttccagtga ctagtgcttc tgcaggctac tcacttgccc ttgcttctgt      5280
ttgcagagga ggtgcagtac attcaggctg agaagaacaa caagggccca atggaagctg      5340
cctcactctt cctccagtac ctgttgaagc tgcagtcaga gggctggttc caggcctttt      5400
tggatgccct gtaccatgca ggttggttcc ttcttcttcc tcacagttca gagtacttca      5460
ctctgctgcc tcagaaggct gagggagaaa agtgactcg ttctgtgaca tctgtgtgtg      5520
gcttctgcct caggcgggaa atgtaaagac tattttgaat cagataagag aatggtttat      5580
accagaaata tccaaagcaa tctacagagt tgtaactact aggagaggtg acaatattag      5640
tagcatgccg gtatctttca agaggagaac gagtaaataa atcggtttta taatgtttac      5700
agtgctccat tatactgcaa tgaagcgtgt ggacatgtct gtaaatgaca acccagctga      5760
actgtaggca cgcagcattt aaatttgaat atcataaact ataatagcta taaagttcca      5820
catgagtcaa actaaacata tagggaagga aactggatct tgggcgaccc tggctgacca      5880
gtcctgggga gtaagcttaa taaactctcc ctgtctgact gagatcggtg tcctgtggtt      5940
tgtgaggcaa ttcctggact ctaacactta ggcaattaca tttcttgccc ctctgccact      6000
ctagcttatt cactggtgaa agaaggagaa tactttagtg ttaccaacaa tggggggggg      6060
ggggcggggg atgggaaatg ggaaaaagca ggcccggccc agtgtagtaa gaaagaaaca      6120
ccaaagaaag ccaagggctc ctgttgcttt cattgtattg gagtgtttgt cagtcggctg      6180
ggggatgggg tgggggtgg ggaagcacac ctttaatccc agctctgggg aggcagaggc      6240
aggcagatcc ctgtgagctc caccagtcat ggctggcctc agcaagaact gtatccatca      6300
catcctaaca caggtgtgtt gaattaacat ggtactgtta aagcaaacac gctgccttcc      6360
tcgggtgctg cggtccctag gaagccacac attggcagca tgttggcagc agttgtataa      6420
aaactaatgc tttttttttcc ttttcttttt aattcggtaa aagggtttaa atgtcatttg      6480
ttataaaact tggtttcctg ctatttccag gattaacaat tgacttattc tttctatttc      6540
```

```
ctgctttata gaccatcatt ttgatacatt atctatttgc atctcagtga tacatgctta   6600
tcttacccct ttatttcgtt ttaagaattg tgtgtgtgtg tgtgtgtgtg tgtgtgtgtg   6660
tgtgtgtgtg tgtgtgtgtg tgtctgagag tgggcatgca tttatgagtg cattgcctag   6720
aggtcagaca ttccctgga gctggagtta atggcagttg tgagggactg acgtgggtgc    6780
tgggatctga ccccagtccc ctgcaagaac acgatgaacc ttacttgcta agccatctcc   6840 ccagcctta gctgttgcag ttactctcca ttccaaataa gccctggcaa tgaaaacaag    6900
acttaattca tatgaataca tgctgtgcac ctagattggg cagatctacc gctacactac   6960
catcttctcc atctatgaga ctccccttt ttttttcttt tttttcttt ttgtggttt     7020 ggtttttga dacagggttt ctctgtatag ccctggctgt cctggaactc actttgtaga   7080
ccaggctggc ctcgaactca gaaatccgcc tgcctctgcc tcccaagtgc tgggaattaa   7140
ggcgtgcgcc accaggcggt ttctccaggc tgtgtgcttc tgctccactt tcttcctcc    7200 tcctctgtgg tatcctctcc ctcttcctct ttctccttct ctcttcccac cttcctctcc   7260 aacttcccttt tatcagccca atcaccagct ctcctttatt ttactaattg aggtgggaag  7320
caggtttaca ggaaatcacc ggagtgctga ctcattcctt gttcgcagcc actcaatgca   7380
gaatggaatt accatcaaat ataattagcc ccagggctat ccacaacact tacctagcac   7440
atcaaatggc ccagcagggg atcaagagaa aaggaaactc aacttctgct tattttcctc   7500
atctcttatg tagcccatc agagaagctg ttgttttcct tttgtgggct ctaactaatt    7560
tgaatattat atttaagatc tattctctta agtaaaaatg gcacagctaa ctttaactgt   7620
aaaattatat gaggtttact aggaaaagtc ttgagtttaa gcaagaaagg gaattttaaa   7680
acatttgtat tggaacataa gtgctggaac atctctcttt gcaagtgagg tgctttgtgt   7740
gtacaaccct aagagtttct ttttttttt ttttttaattt atttacttca tatttcagac   7800
agatctcatt tcaggtggtt gtgagccacc atgtggttgc tgggatttga actcaggacc   7860
tctggaagag cagtcagtgc tcctctgcgc tgagccatct ctccagcccc cctaagagtt   7920
tcataaagga atagtctgca ttaataaatt cagaaaaggc tcagaatata aagccaatat   7980
catcaagtag gttccagtt tatgtattaa caaataatgc aaaaaagatt ttaagcaagc    8040
gattcctttt ataacagcac caagaacaat aaagttagga atgccagtgc tcctaactgc   8100
tgaaccacct cagcaatgca aactttaca tcttagcact aagtccagct cctaattcgt    8160
gaatgtaaga tgtcattcat gtccgtgtcc ctatggttcg tttcagaagt ggtttatggt   8220
cttcgggtca taggtctttc ccctgctcag ctttgcttat tcctaacttt atttaaagtt   8280
ctcactgttg ttataaaagg aatcacttgg ggctggcgag atggctcagt gggtaagagc   8340
acccgactgc tcttccgaag gtcctgagtt caaatcccag caaccacatg gtggctcaca   8400
accatccgta acgagatctg actccctctt ctggagtgtc ggaagacagc tacagtgtat   8460
ttacatataa taaataaata aataaataaa tcttcaaaaa aattctaaaa aaatatggaa   8520 aaaaaggaa tcacttagtt aaaaatctca ttcctagccg gttgtggtgg cacataccct    8580
taatcccagc acttgggtgg cagaggcagg cggatttcta agtttgaggt ctacaaagtg   8640
agttccaggt ctctgaaaac cacaaaaaaa aaaaaaaaa atagcactgg ctgctcttcc   8700
gaaggttctg agttcaaatc cctccaacca catagtggct cacaaccata tgtaatggga   8760
tctgatgccc tcttctggtg tgtctgaaga cagtaacagt gtacttacat ataataaata   8820
aataaatctt tgggtgggag tgagcggggc tggagagaga aggaaaagta tctgaagaca   8880
actacagtgt acttacatat aatagataaa taaatcttta aaaaaatcaa taaatgaaag   8940
```

```
atgccaatat acccagagt tggcacagtg ataccttca taatgccaaa ttttggtggc    9000
aggattgttt gtttattaaa caggaataga aaaatttact ctcaaatttg tatgaaatct    9060
taaatggtca aaatattgga aagagaaact cacttggaaa ccttggggga cttatacttc    9120
ctggtgtcaa aacagtacag aacctccata aagccagata attagaccat tagcccagaa    9180
gtaaactctg aaggatatgg ccaaaggttc ttcaacaagg gtaccatgac cacccaaaag    9240
ggggaaaaaa aacccagtcc ctttaatatg aaaatacatt ggggtaagtg ggtatacata    9300
tgggaatgag aggtatcagg cataatcttg tgctatgatg tgaatttgaa atgttctcat    9360
cacattcatg ttttgagtgc ttggtcccca gcttgtgggg ttttaggagg tagagcctag    9420
ctagccaaag taacacgtgt atacgttcat gcatgtgtgc acacaggtat gagggtactt    9480
gtgtgtagcc cagaggctga cattcagtgt cttccttagg agctctccac cgtatgtttt    9540
tgggaatgga tctctcatta gacccagaat ttaccctctc gggctcgact ggctgggatt    9600
atagggtcat gctgctacac ttggcttttt acatgatagc tggggacagg aactcaggtc    9660
ccagccttgt gtggtgagca cttttctact aagcaccttc ttggtcctgg agctattttg    9720
attgttttag tttttgggt ctataggggg gagaaaaaaa aaaaaaccac attgtcttcc    9780
cagggccttg aatgaagtaa atgagggtct gagaggcagg cacgcctggt ggatctgtcc    9840
aaaaacccca gagtacggca ttcttggatt cttttagtca gaagtcattt tccttctcca    9900
tttgcccatt gacttaatct tttcttggaa tggtgtggaa ggaaacactt ttcaagggca    9960
ggatgtaaga tttgtatttc ctctggtctt ctttactgtt tcctcttgag aagataaaca    10020
tgatgaattt gactaattta aaagtaaatt gagatgacaa agagatggct ctgtgattaa    10080
gagcacttgc tgatcttgca gaggacccag gtttggttcc tagacttaca tggtagctca    10140
caaccatctg taacttcagt tccaggaatc tgaccctctc ttctgctctc caaagatacc    10200
agacacactc acgatacaca gacacatgca aagtaaaata gaaataaata ttaaaaaaaa    10260
atatattgtg ggttgttgtt aaagtgcgtg aggggcattt tgaagatttt attctaaggt    10320
caaatacaag gcctcatatc tgtccttagg acttgaccct gaaagataat gaattttagg    10380
agacctaaac tgttgggtac caaaaatgag tattactccc attttggaaa atcatgaata    10440
gctgtattag ttgactttaa ctactgtgag taaatgcccg aggaaataaa aagcagaaaa    10500
atgagagcca agaggatctg tagcttctgc acccgtgcgt ggtgaggcag ggcaccatgg    10560
cgggagcatg tgggaaaagc cgcactttct ggtagacagg tggcaaaggg tgccgggcag    10620
gggccctgga caagatgcat tcttcaaagc acatctccag tgactcactt ctcccagaga    10680
gggtacagtt ctcagttgct ccttctgtat gaactcaatg tgctgccagt ggtgacgcca    10740
ggactcgaag gatgtggtca ccaggtcccg cagggtgtgg tcacctctaa agactgtcac    10800
cagctggtgt ccaagcctgc aacctgtcag cctcatggtc tggctcccca gactgtccag    10860
tgactgaggc catttgcaga tggttttcag ttcccttgcc actgatttga acaggattcc    10920
catgattttg acttcaaagc atttttatgt tggatttgct taagaaatcc ccatttctct    10980 tttcttttc aggttactgt ggactttgtg aagccatcga agttgggac tttcaaaaaa    11040 ttgaaaagtt agaggaacac agattacttt taagacgttt agaaccagaa tttaaggcca    11100
cagttgatcc aaatgatatc ctttctgaac tatccgaatg tttgattaat caggaatgtg    11160
aagaaatcag acaggtaaac caatgccagg tactaaattt gaagaaaaat gcagagacat    11220
tggaaatgcc cattttctg tcttgtttta ggcccaagga taattgaaac ccataaaagc    11280
tctcatctag cagatataat gactagaata gaattttta agtgaatggg gtaattttg    11340
```

```
tgctagacta ttagaaaatt atttaaccta tttgcagtta aagttgcccc cttactttaa    11400
aaaaaatagt ggtttatgca taatgcaaat cacaccaaac agtgcaacaa ttaaaaggaa    11460
aaatatgtca ggctcttggg catagataca tttattacag tctcgcagtc acttaactag    11520
tgatgtgatg ccaggcagtt ctctaagcat ctgtggggtt tttgttgttg ttgttgttgt    11580
tgtttgtttg tttgtttttc atgtctaaag taagaaaatt tatcttttgt ttttgtttt    11640 tttgttttt tagatttctt tattttattt tattatatgt gagtacactg tagctgtctt    11700
cagacactcc agaagagggc gtcagatctt gttacggatg gttgtgagcc actatgtggt    11760
tgctgggatt tgaactcagg accttcggaa gaacagtcgg tgctctcaac ccctgagcca    11820
tctctccagc cccctttgt ttttgttttt gttttgttt ttgtttttt gtttgtttgg    11880 ttttttgtc gttgttgttg tttgtttgtt ttgtttttc gagatagggt ttctctgtgt    11940
agccctggct gtcctggaac tcactctgta gaccaggctg gccttgaact cagaaatccg    12000
cctgcctctg cctcccgagt actgggatta aaggcatgca ccaccacgcc cgacgaaaat    12060
gtaccttatt agcactcttt tagggctaaa tgagaggtca tgcacaaaat gtgtatgtca    12120
gcttgatgca tagcagtcta tgcacaatgc atttcagtta tcattagaaa gaaaagtcat    12180
agaacatctg cttagaaaag agacctgctg ctgtgctgtt aggcatttcc aaatggctct    12240
gtgtgccgat acatccttag ggtgaatggt tagcgtctgg gttaacgctt ttaccccagg    12300
attgctcttg gtcagggata taaggattca gaagatgaga acatttgcct tggcatattg    12360
ataacacatt ataaggaca aaggtgaaga aaggaatatc ttaaaagcta gtgctggaca    12420
gggcaaaaag atgatgctaa ctaagcccta ctcaactata cttcacagtg atttcaatca    12480
gataccgctt ccacaaaagc ttgccagagg aaaggctgag ctgcctgatc agtgtgctgc    12540
atttgtctcc cccagatccg agacactaaa gggagaatgg caggtgcgga gaagatggcc    12600
gaatgtctta tcagatccga caaggaaaac tggccaaagg tcttgcaact gcttttggag    12660
aaagacaaca gcaagtttag tgaattgtgg attgttgata aaggtggggt gctccaagaa    12720
agaaccctgg accctgctgc gctcctccca gttctcccca cttacttc catcagaggc    12780 gctgttcact tcagatacca aaggctatat ccctaggata caagcagtgg aaagctgaat    12840
tctgggagga agggaactac atggcatgga attaacccga ccaggtcaaa gaatctaggg    12900
aaggcttcca gccccaattt gttatcagag aaatagcttg agaattctag acctaaaggt    12960
tcaaactgca agacttacct ccctatcaga gcagaggctg agtgttgggg gtgatagcta    13020
tggactggtg ctcttgcccg gaagccatct ggactccgac agagcaagag taaacgaaga    13080
ttttctgtgt ttaagccaac ctcatttggc ttccggaaac tcacttcttg ctttaaacag    13140
accttgataa atacctgagt ttctagtttc ctttctcacc tagatttcct tagaacataa    13200
attattccag aaactctcta catcgttggt cagagatgga atcctgtctc tttagtgtgc    13260
tcaggaatga cgcccctgcg ttattggcgt gagttccgga gtggggaggg gctccggatg    13320
caaactgctg agagccccgg gttccacact tggagtcgcg tagttccaga tgaaactgga    13380
attcaattgc caagttgagc ttcaaactca gaataatcct tgcagttgtt ttaagccgtc    13440
aaagtggggc tctctagatg gctcagtgga taaggttcct gccactgatc ctgaagaccc    13500
aaattcaacg tccagggcct acatgataga accaatcccc aaacagtgtc ctcatccctc    13560
ggcacactca ctgtgtcgtg tgtgacacac acagtaaaca aatccatttc aaaaataaat    13620
aaaatgttaa gaaagtgcaa gaccgtgatt gtaagagctc aacggaaatt tagatgttta    13680
gtgttagtgt taggactttt tgggacttcc ccaaccaaaa ccataatcac attgcgcatg    13740
```

```
cttttaatcc cagcactcag gaggcagagg caggtggatt tctgagttcg aggccagcct   13800
ggtctacaga gtgagttcca ggacagccag ggctatacag agaaaccctg cctcgaccac   13860
caccccttc  caaaaaaaaa aaaaaaagat tctaagctgt aagctgttat tgtgtttat    13920
gattgtttgc ttgcctgttt atcacaaagg tttcaaaagg gctgaaagca aggctgatga   13980
ggatgatgga gcggaggcgt ccagcatcca gattttcatt caggaagagc cagagtgtca   14040
gaatctcagt cagaatcccg ggcctccttc aggtaccaag catcgtttgc tctcatccat   14100
gatggtgtcc cccagcactt tgatgcccttt tgaaaaaaag tcttttaaa  ggatgattaa   14160
gaaaagaaag aatttgtggg gcaataggga cttcataatt agaatccctg ctcctgtctt   14220
ccatggcctc tgcatggcct tcaaccctcc ccctcctctc ccctcccctc ccctccctc    14280
cagtatgtat gccttcatct gtaccgtgtt cccagaactt cagtgtccat gacttctcaa   14340
agcagccttg ctctctaaag aacacttctg ctcactaagc aatggctttg agaatctggg   14400
ctgacagctg gttttcctcg gctgtttttg atgatctgtt cttactttgt tccaagtggc   14460
tttgttttga attaggccat tcttgctgtc ctttttcttg ataaagtttc cacgattaag   14520
aaagaattca tggggctgga gagatagatg gttcagcgtt taagagcacc gactgttctt   14580
tcagagatcc cgagttcaat tcctagcaac cacatagtga ctccagcgtc tgggttaatg   14640
tttttacccc atctgtaatg ggctctggtg tactcttctg gtgtgtcaga ggacagcgac   14700
aatgtgtata ttcatataca ttaaataata aataaatctt caaagagaaa agaaggaagg   14760
aagaagtaac agagagagag agagagagag agagagagag agagagagag agagagagag   14820
agagaacaca ctttggccaa gatcccaaac ctcaaacagg ggcattgttg ctagagtcag   14880
aactcatgtc cactgaatgg cagttgcacc atgattcctt gtagcatgaa cccttcgata   14940
actttgtccc ctctatatta cagaagcgtc ttctaataat ttacacagcc cattgaaacc   15000
aagaaattac caactggagc ttgccctgcc tgccaagaaa gggaaaaata caataatatg   15060
tgcccctact ggtaagtcag ttgctgtcac tcacagaact ctctggcttc gcttttttctt  15120
ccccctttgg gggctgtaaa aggaggagtt ttccccgtgg cccatgctgc ccatgggaga   15180
gctggtctag cagcttaagg aacctggaca gcgataagga gggagataag tgtcttcttt   15240
agtttgctttt tggttcttgc tacctgagtg cacgttactt aggaagtagc ttggcacttt  15300
tcagccattg tttaaactgt cattgttagt gcggaggagg gattattagt ttatttgtat   15360
cccagtggtc atagagaagc caaaataagt accattctgg aaaaacagct aacacaggtt   15420
atctgttggt ttttttttct tttcttttttt tttcttttttt cttccctact aaaaggttgt   15480
ggaaaaacct ttgtgtcgct tcttatatgt gaacaccatc ttaaaaaatt cccatgtgga   15540
caaaaaggga aagtggtctt cttcgctaac caaattcctg tctatgagca gcaggcaact   15600
gtgttctcac gatattttga aagacttggg tatgtactac tacaatcaat ctaactgctt   15660
tgattttgg ttttttgttttt gtttatgttt gtattttaaa ttctagcccc tttggctggt   15720
tttgggggct ttgttgtgtc tggttttggg ggctttgttg tgtctggttt tggggctttt   15780
gttgtgtctg gttttggggg ctttgttgtg tgttttctga cagtgtat cacgtagcct     15840
tgagttgtct ccaacccact gtgtagctga ggttggccta aagagatga tcttcttgct     15900
tctacaagtg ctgagattac agtgtgcact ggcatgcctg gctgttctct gattttcttt   15960
cttttttttt ttttttaagat ttatttattt attatatgta agtacactgt agctgtcttc   16020
agacactcca gaagagggca tcagatctca ttatgggtgg ttgtgagcca ccatgtggtt   16080
gctgggattt gaacttcgga ccttcggaag agcagtcagg tgctcttacc cactgagcca   16140
```

```
tctcaccagc cctctctgat tttcaaagct atgattaaag gaaaatcgcc atggacttaa    16200
cttttagagg tagttccttt gtgcaataac attttttggtt taactttacc agaaatgcta    16260
agccctcatg tcatgctctg acagttaatg aacttggtgg ccaaatttaa catgtaggcg    16320
atacacaggt catccttaat gatgttatac ttgattggct attactcttt tcaaaatcat    16380
ttctctctta atgacttgaa agaataaata cactgtgatc agctataacc tcttgcattt    16440
cctgactccc cggctttgtg tcaggcctgt gagaaagttc aaggtactac ccagttgtac    16500
tcttttgggc ttgggctgac ttctttaatt gctgctctga cctagacttc tactttgtct    16560
ccttgttcat tcacatcaag gttgatgata agggatttct gtcattcccc aggtacaaca    16620
ttgcgagcat ttctggggca acatctgata gcgtctcagt gcagcacatc attgaagaca    16680
atgatatcat catcctgaca ccccagattc ttgtgaacaa tctcaacaac ggagccatcc    16740
cctcgttgtc tgtcttcact ctgatgatat ttgatgagtg tcataacact agcaaaaacc    16800
acccatacaa tcagatcatg ttcagatacc tagaccacaa acttggagag tcacgggacc    16860
cactgcctca ggtatttcca atcttctaag aagaaccaca gttttcaga gtcccactta    16920 gttgctcttt tgtagccaca tttgagcttg ccctcctcgg ggtctcagtc catcggtaca    16980
actcagtggt caatgttggt tcattcattt gaccaacagt tgtcccttgg tgtccagggt    17040
agatgccctt cacaaaaaac aaaatctagg ctgcttaagt ctcttgtatg agatgacatt    17100
gcatttatat ataatctaca cactttcctc ttgcatactt taaatcttct ctagattact    17160
gatattgtac agtatgatga aaattttata taaatagttc tagtactgta attttttaggg    17220 aataaaggtg ggaaattcat acatgtttag tacttatgaa gttttaaaaa atattttga    17280 tccatggttg tatgaattca catttatata acctctggat ttggagggcc agctgtataa    17340
accatgggct tccatggacc ttgtgcattg ttctaggctc tgggcacacca atacagaaga    17400 tatagtcctg gctctcatac agttaagttt gcagggagcc aggaacatag tagtcacagc    17460
ttatcatgag gtatgctgca gagacaggta aagggtgttg tcagaacata aggggtaata    17520
aggcatagaa atgaagggaa ctgacagggg cttgccaggt agatagcttc tggtttctag    17580
taagagggtc ctgtgtgtcc aggggctcag ggaaatggaa gggcctgaca tgccccagaa    17640
ccttaaaact ctacagtatc acttgagggt agagtgtgaa gcagggaaca acagtcaagc    17700
tgattgttat gacagatgac ccagagacac caggagggca gagcgtcagt gggcaagtgg    17760
atggcttagc acagggaaca agcagcagcc ttctgatgtc atatgagaag agtcacttca    17820
gagtcattct tacatgtgac aagaggagta caaattctcc ttctgtctat cataggagag    17880
ggggtgcttt gctgaaagtc aacgatatag aaacaggagg gggctagaga ggatgaggac    17940
ggtttgactc aggcactgat agatgcaata agaatgacg gtagtgtatc tatcaggggc    18000
cccaagaagc tgtaaaccat gaattatata caattctttt gctccaacaa taacctttt    18060 aggacgtgca ggttaaagga catttagtac aggacccaca gtttgttatt ctcgagtatc    18120
gttgctagga agcagatttc ttaccgtcca gctaatcatt taggtgaatg cttactgaag    18180
ggtgttatca tactgaatct acacagctct cttgtacacg actcactgat tgttgaaggt    18240
atttgtccag gcgcacaaaa tgcatgtgat atgaatgagc ctggaatgga cttttttcttc    18300 ccattgtgat gtttagtaag agactggggg ataaaaaaaa cagggtagcc ctgcctggaa    18360
aggtttcctc tctgttctgg atgacacgct agatttattt ccgagctttg ctccaggggg    18420
gtctttgtgc tggagaatgt cagagagcca gtggtggggt gctccttaca ggtcgttggg    18480
ctgactgcct ccgtcggcgt tggagatgct aagaccgcgg aggaagccat gcaacatatc    18540
```

```
tgtaaactct gtgccgccct ggatgcctcc gtgattgcca cagtcagaga caacgttgca    18600
gaactggaac aggtcgttta taagccccag aaaagtaagt ggaggtcagc agcccacacc    18660
tcgcgacttt gtaaccttct gtccctctg cgtcagagac agtggatgaa gtttgatgct     18720
gtatttgttt ggtaaaagca tagtggttac attgcctatc tttctccta gtcaacctct     18780
tctccctagc gacgcatgag tctcaaaggt agccagaaag ggacaaacat ccctactctt    18840
taccagcagc tgagtgaagg aggcagtggg aagattcaag cattttgaaa gcctcaatag    18900
ctagtggcgg aatcaggtct ctgtgctccg ggccctaggc aggggctatg tggccatctt    18960
gttcttgtat gtatctgatc attgtagtgg catgacccga atcatgacag ttcaaaaggc    19020
cagaacatgt ttttaaaatg agcttcatta gaagatggtt attacttatt aactacctgt    19080
gtaagcaggg aggtaccgta gttcccacg gctggatctt ggcctgagca ctcgttctgt     19140
gagttgacag caggatcaat ggcagggtca atggcaggat gagcaatggg ggggtggggg    19200
ttgggatggc acaaccctgg ttcttttctga gagtcccccg tggagagtgt gaagaaggtg   19260
cctccccacc cacgcccacc ccttagcaac actcaagggt ttttctacag tttgagccct    19320
tggagcttag tctacttcaa agtcatttg tgtcactttc tccgtctatg caaaccctct     19380
acgagctatt ctgagggtgt gtcccagctc ctgcgcgcct tccttttttcc cttattattc   19440
atcttgcggc agcttccccg gagagaatga ggtttcctcc cctctttgag agatgccttc    19500
ctggcctgca cctgcttccc agggctctga tgggcgggtt taggagcaca cctttgtttc    19560
cttaaggag tgggtgggtt ggggagcagg gggaggggg agggagggga tagggggttt       19620
ttggagggga aaccaggaaa gggaataaca tttgaaatgt aaataacgaa aatatcttta    19680
aagaaaagaa aagaaaagga aagaaagaaa gaacctgcct tctgtgcagc atagggtagc    19740
tcttgtcagc tctctgtcac tgaaacagga catgtgacag gcagttctt ttctgccaaa     19800
agtacacaaa tgtgaacgat aagctcaatg ggggcactct tgggggctcg gaggtgcgca    19860
ggagaatagg aaatcaggaa aacggggctg gagtatggta tttgccgaaa ccagaaggct    19920
gccagacctg ccacagtaga ggcaccagga aagctgactg agacgctggc ttagactaga    19980
ccaggagaga cactagaatc agaagcagtt ccgaggtcag aggcttctga ccgcctgctg    20040
tgatttgggc cacgtgagct tggagcctgt ggctttaaag gacttaccca ggatggagca    20100
gcttcgggaa atggctgcat aggacctggg ttttccttcag cttactcaca tgcctttgac   20160
cccagtttcc aggaaagtgg catcccggac ttcgaacacg tttaaatgca tcatctctca    20220
gctgatgaag gagacagaga agctagccaa ggatgtctcc gaggaacttg gtaagcctgt    20280
gccaagtcct ggagagagaa atctcatgtt tcctgtccct tccatttaga ggtactcatg    20340
gattgctcgt tagtgtcttc agttttgggt gagattatac tcagaggtgg actgacttat    20400
ttattcacac atatttcttt ctgtctctgt atcttcttta tctcttcatt cttttttgcc    20460
atcatttttt tctccattcc tttttaaaaa gatttatttt tatttgatat gtgtagatgt    20520
ttttgtctgc atgtatgtat gtatatcaca tgtatcagat acccgggaac tggagttaca   20580
gacagttgtg agctaccaca tctgctggga atcgaaccca tgtcctctag aagggtagct    20640
ggtgcgcata accactgagg agcccccatt tctctagctg ttttttaagac aaggttttt    20700
tccctgtgtc cctggttggc ctgaaacttg ctatgaagac aaggctggct ttgaacttgc    20760
agggggtcccc ttgcttcagc ttctgagtcc tggggtctct ggcaagcgcc accataccctg  20820
gctcagatat agactttctt aatcctaggt tgtttaggaa cctttatagga gttctttaat   20880
tctctcttgc cttttctctt ttaaatacaa aacacatcca cctggacata catacctgag    20940
```

```
aaatactgtc tttaaatcat cttctaaatt tcctttcttc cttttttttcc cctcttgaga   21000 tagaatctct gtgttcagtg taggctggcc ttgaactggg aactctgccc ctcctcctcc   21060
tcctcctcct cccaagatgt gcatcatcac tgagctgcca ttagagtgcc attgtccctt   21120
ccaagagcag ttcccccagt gacctaacac tctctcactg tcctcagctc ttgaaagtgt   21180
caccacctcc taacctcaca cactgaggac caaccagcct tttgccacat gagcatccag   21240
aaggcactta gacagtagct aaggcacagc actgggggag gagtttgaat aatgaatcca   21300
ctatgggtcc taaagtagta gggtagcaag catgctctct cctctagagt tttggaaact   21360
ctctgtaagg taaagagtaa agagaccagg tagtcagtac atggctcacc taggaacaag   21420
ataacatggt ctgactaaag tggtggatgg acagacggac aggaatagag ttgtatgact   21480
tacttttttg ttttgttttt gttttttaaaa cagtctgtct gtatagctct gactgtcctg   21540
gaactctctt tgctggcctc aaactcacag agatctgcct gcctctgcct ccggaggcat   21600
tcacacttta gaatcttttc ccacctcctc acattgagta tctgtcaata gctgcctcac   21660
ttcttctgga acttggacgt ttttcattgt gaactgggtg tggtggcacc atctctactc   21720
ccagcagctg ggagcctgag tctgaggcca gcttaggcta catactgagc tcctgtcctt   21780
ggggcggagg ctgggaagaa cttgtcactg tttcttgttg gtacccgtcc tgtgttctgt   21840
tattgcaaat gtgagggaag ccatttaaca cacaaatgca tttcacttct ttgaactgta   21900
ctgtgcttgt ctcaagaagc ccaggacaca aaacaataga gcaagcatct ggggctgttc   21960
ccacttcgcc tttccccccc tacccacacc aatcttcccc tgagtctgaa tcgctgtgaa   22020
tcccacagta gaaccaagca gtcaagacat gcacatgcgc acacagatgc ttccgggata   22080
actgtgtttg actccgcctt gtggttggtg ctgcaagtgc tgctctgaga tcaggtgttt   22140
gggcttcata gcaacataga gcatgctggg aagggtcctg gtgctcccat tttatataa   22200 ctgtctccga tgaagctctt gagacgtgct actctaatgg tatcttcatt ttgaaaggca   22260
aagtgtgtcc ctccttctct tcctcctcct ccttcttcct tacccctctt cttcgttctc   22320
tgttatttct gaactacttt ggctgtcagc cccttaagcc tgcagagcat agacaccaca   22380
gagctaggct tgaattcttg cctcacccac acaatatgag ctttatgaca ttgggggtaa   22440
attagttttc cttttataga agatttattt acttaaaaaa aaattatgtg catgtgcatg   22500
tgcgggatgg tgttgttgcc tccaggggtc agaagagggc gctgaatgcc ctggaactgg   22560
atttacaggt cgttggaagc cacccaatgt gagtgcaggg aactgaactt gggtcctcta   22620
caagggccta actattgagc caccacttct gctccttact caatcttct gaatctgttt   22680 cctctttttt tttttttaaag atttatttat ttattatatg taagtacact gtagctaagc   22740
tatcttcaga cactccagaa gagggagtcg gatcttgtta cggatggttg tgaaccacca   22800
tgtggttgct gggacttgaa ctcaggacct ttggaagaac agtcggtgtt cttatccact   22860
gagccatctc tccagcctgt ttcctctttta aaaaaaaaa ttaaataatg acctcatgaa   22920
attagaaaat ttcaatgcaa ttatgaagct tgattttggg tcatttagta aatagttatt   22980
ttacacactc ctcccccca ccccccgcgc acgcacacag gcacacacac acacacacac   23040
acacacacac acacacacac acatagctta agacccagtc tacttcagga taaacatctt   23100
tcttataatg aataagaaag aaaatcagag gaccggtgct tgcaaatctt ttatttatct   23160
atttatgttc ttaccctgta ggaaagcttt ttcaaattca aaacagagaa ttcggcaccc   23220
agaaatatga acagtggatt gtcggcgtcc acaaagcgtg ctcagtgttt cagatggcag   23280
acaaagagga ggagagccgg gtctgcaaag cgctcttcct gtacacatca catttgcggg   23340
```

```
tacattgctg ctctccaggg cttattctca tcaccgcgcc tcctgggatc tgtactgagg  23400
cagctgagag aacatcagcg tctcaagtct aagagcttag tgaggaactt ttcccgaaag  23460
tcatcactaa ccttatttgt tttctgaaac ttatcatcaa gtctccaaaa actggattaa  23520
aggctcagag tctatgccac acctccctcc agcttgtgac tggtgaccac catctaactg  23580
agctcaaaaa agtggctcct gtggccatat cctgaagctt tcgtggtctt aattttgtta  23640
taaagtcata tattagaatc tcaggggctc tggttaacac agagggaagg agtaactgta  23700
agagccctca gctctgtttg ctatgctctg ggaactattt aaagacttac tccacaccat  23760
gggattgtgg gatctaacgc ttaatggact ttcagcatag gtggtaaggg ccatcgttat  23820
gcaaggccca tgtacacttt aagtatgact tggaatttaa ggggaatgtc aaagctaact  23880
tgcttttgtt attgtttctc aagatatgct gtttctcctc tcccaaggtg gagttttata  23940
atccaaagtg aatctacttt taattttcta gctgagccaa aaatagaagc cagcttttgg  24000
ttcagaggtt tttattgtag acccactaag ggccattcgc cattaaaccc tcagctgtac  24060
tgtatgagaa agattttctg caaaccagtt ttgtgctaaa tacagcgagt tgaacttgag  24120
tgtagtgacc atatgcgacc tcagaaatgt attgagaatc acttttcatt tcaaacagaa  24180
atacaacgat gcactcatca tcagtgagga tgcacagatg acagacgctc taaattacct  24240
caaagccttc ttccacgatg tccgagaagc agcattcgat gagaccgagc gagagcttac  24300
tcggaggttt gaaggtgagg gagatttctg aagtcaggag tccctggggt ctggtggctt  24360
ttgtggcagt gtgcacatcg tagttagcat acgtagccat catgttgggt ttaaggtgag  24420
atttgtaggg gctgtgacgg agcatgacct tagcatggct gaaatcccca gcactaaaaa  24480
acgaacctat gctgaaactt tagagccaac caaccgacaa caggagggtt tggcttcaga  24540
gaaatctaat gcctgtggat ggatctgatg cttgccccac ttttcacttg ggaaaatggg  24600
aaacagtggg atttggaaag ggtgcttcct ctaggtggta ggtagtgcta ttctgattaa  24660
ctcagtaatt cagaaggttt aataacaaca gctcgtgtct gatggtgtca agattgtgct  24720
gtatgtatgt ccttccttcc ttccttcctt ccttccttcc ttccttcctt ccttccttcc  24780
ttccttcctt cctccctccc tccctccctc cctcccccct ttctcttctc ttctcttctc  24840
ttctcttctc ttctcttctc ttctcttctc ttctcttctc ttctcttctc ttctcttctc  24900
cttctcttct tcctcctcct tcatcttctt cttttcttcct cctctcccttt ctccttcttc  24960 ttcaaaacac agtctgtata gccccggctg tcctgaaact cactttgtac accaggctgg  25020
cctcgaactc agaaatctgc ctgcctctgc ctcctgagtg ctgggattaa aggcgtgtgc  25080
caccatgccc agtttgtgca catatatgtg catatgttta ttataaattt tactgataca  25140
ggagatggca tagcacaaaa cacacaaata ataaacacgg agttcatgtt ccacagaatg  25200
cctttggagg tcttttcagt acccttgtgt ccagagccaa ccagagacag caattaccca  25260
atatggagtt ctgaaatgaa agtcagtttt atttcctgtt aatggcagaa ataagaacaa  25320
aacgaaacag cagaagcatt ttggaagctt gcttgtttct cagtgatggg agcaacattt  25380
ttctgagcca gataatagtt tttcaaacac gggtgggaca tttctgcatt tttacgtgat  25440
gcataaacag tagctaaatt taatccccat tatatactta gcactttaca aagtctagcc  25500
agacaataaa ggatgaagca agtgctatct tcatttccat ggtatgggta cttctaggat  25560
caccaatctc caaccatcac catgttgctg aacttgtgta aaattgagca gtaacacaca  25620
ctgacatttc taccattcat acactacagg taagtacaca ctcaagagcg tagataatag  25680
taaactgtaa taaaatgagt taggaaatta ataagcgtgg ctatttgtta catttgtttt  25740
```

```
tagtcattga gctgcaagca taaagagttg aaatttttaat aatagttata tttaaaacca    25800
ggtccacaag tctgaagaac ttaataactg accataatct ggtttgatct ggttctatct    25860
agtacaccac cagtgtgtgt gtgcgtgtgt gctcctatgc atacttatac attaaaaaaa    25920
aaaaagatat cctatgcttc aattttttaac ataaaataac cttctgacag ctgggtggtg    25980
gtggtggtgc atgtctttaa ttgcagcact caggaggcag gggcaggtgg gtctctgggt    26040
tcaaggccag tctggtttac agagccagtt ctaggacagc cagggctaca cagagaaacc    26100
ttgtttcaag acaaaacgaa acaaaacaac cacaaataaa aatatatctt tttgatgtt     26160 tccaaatcag caggtgtata taactcttta actttaatag taacagtgta tttacctcag    26220
tttggtagcc tgggatccat tgagctgttt ctcactaagc agtgttttgg ttgttggttt    26280
tttttttttt ttttttttt ttttgtattt agttcatagt ttcaacactg attgtccttg     26340
gaatcttctt cagagttttt tttttttttt tttttaaag atttatttat ttattatttt     26400
atttaagtac actttagctg acttcagaca caccagaaga gggtgtcaga tctcattacg    26460
gatgttagtg agccaccatg tggttgctgg gatttgaact ctggaccttc ggaagaacag    26520
tcggtgctct taaccactga gccatctctc cagccccaga gttttctaaa tagaactatg    26580
agtcaattcc tatctgtgga ttgctgtatc aaagaacatg tgagttttgt attgctgcgc    26640
tgcttttcta aggggattc ctgatgaaac gagtgtttac tgctctgatc tctggtgaac     26700
agtggaaagg ttaaccgaaa tagaaggcca ctgtttgttc taaagcttta acatttgtaa    26760
gccttttgca aaatgctctc tatttgcaga aaaactagag gaattagaaa aagtttccag    26820
ggatcccagc aatgagaatc ctaaactaag agacctctac ttggtcttac aagaagagta    26880
ccacttaaag ccagagacca agaccattct cttcgtgaag accagagcac tcgtggatgt    26940
aagtgtgtgt gtttacagat tagctctagt ttattgaaaa ggttgcccgt tcttcactgc    27000
cttataatca agtatccata catgtgtgga cctgttctga tgatttgttc ttacaccaat    27060
tgtcattgtt tgtattgacc cacagttata agtcttggtc ctatagagga agccctgcat    27120 ccttttttaaa aatttaaaat ttccacttcc agtcatcctg taggttttga ttaatgacta   27180
atgtgtctta tataccctcac agttatcttc atatcatctt ttaaaaataa tttactcaga   27240
ttttaaaaac cagttttaaa attgggcaat gggctggaga tacagctcaa tggtcaaatg    27300
cttgttcagc atgcatgact ttaatcccca gttctggaaa aagatagata tctctctgtt    27360
tatgtagaat gccttgagtc tggccacagc gcctccctct gtttatgtag aatgcctgca    27420
ttgtttctgc tgagtagtag attacccata gagccagagg cagaaaaagt caagctttat    27480 tatttatga gatccgtgga tcaggatctg gaaaggactg gatacttatg cctcaaggtc      27540
tcctgaggcc acagtcagct cggcactcaa ggctgacctc tcggctcctt ttgcaggttg    27600
ttggcaggct tgtgaagatg agcctccaac atggcagctg cccctgccta cagtgagatg    27660
agagactgag gagaagaggg cctagtagac agacactgcc attttataaa gtccatcttg    27720
gacctgatgt cccaccacat ctcccatatt tcagagataa actacagatt attttttagaa   27780 tataggatgt agaagtcatt aagggtcgct tgtcatgtga tctttgctgt cttcttttgt    27840
taatgaatgg gggtgtttac catgtgcgtg tcgtgcccac agagtccagg aagggggcat    27900
gacatgccct ggaactggag ttaacagaca gttgtaagtt gccatgtagg tgctgggaat    27960
tgaactcagg tcctctggaa gaacaaccag tgctcttaac caccgagcca tctctccagc    28020 ccccttttgct gtgttttatt agcatttttgt catttttagt atagaggtcc tgcatacatt   28080
ttgttagatt catacctagg tattaatttt agtgttgtca ttccgaaatt gtactttcaa    28140
```

```
atatttctca ctgtgggcta ggaagacatc tcagtaaagt gtctaaagta caggcatcag    28200
gacctggctt ccagcaacct ggtaaaaaag ccgagtacag tagagtactc ttgtaatccc    28260
agccctgggg acagagataa gcacaaccct aactggcaat gcccaggtcc cagggagtta    28320
ctcattactc agtcttaggc agaacgaagg tgggtggctg ttaagaaatg atacctaggg    28380
ctggtgagat ggctcagtgg gtaagagcac ctgactgctc ttccgaaggt ccagagttca    28440
aatcccagca accacatggt ggctcacaac catccgtaac gagatctgac tccctcttct    28500
ggtgtgtctg aagacagcta cagtgtactt acatataata aataaataaa tctttaaaaa    28560
aaaaaaaaaa aaaaagaaa tgatacctga ggttgacctc cacatgcatg tacacacaca    28620
cacacacaca cacatgcgtg cgtggacata ctcccctcca acacagtcag ccatgtacac    28680
ctccacacaa cacacagttc ttccaattgc agctgtctgc tgatatttac tgtgtaatta    28740
atttacatgg attgatcttt caccttaaag ccttgctaaa tttcacttac tctatgtctg    28800
aagcttgtct ttttaatcac ttaaaatatc tcctacatta agccataatg aggcagagtt    28860
ctatatcact agcatcaatt gttgtttgga atttaggatt tgccagtctg aaatccattt    28920
ttatctttag ttgtattctc tttttgcata tacatccatt atatcaaatt gatgtgaggt    28980
ttaaagttta caagtggtgt ctaactggcc gttgcttttc acttttaggc tctgaagaaa    29040
tggattgaag aaaatcctgc actaagcttt ctaaagcctg gcatactgac tgggcgtggc    29100
agaacaaacc gggcaacagg tatttatgtc tattgaatta gatttagtat actatgtata    29160
taaaatgtat aaacactaca ttgttttagt gtttctatca gtcagagctc aaccagagaa    29220
ataaagctac tagattatgc atatgtatgt ggtatatatg taagtatgta tgcttatttg    29280
tttgtttgtt tatttatgta cttagagata gggtttctct gtgtaaccct tgctctcctg    29340
gaactcactc tgtggaccag gctggccttg aattcagaaa tccgcctgcc tctgcctccc    29400
gagtgctggg attaaaggtg tgcgccacca ctgcctggcc tatactgtta ttctttaccc    29460
agtagatttt ttttcccat ctactgcctc tttaatagtt ttaaaaaaac agtccaggca    29520
atcctgaact ctagctagtg tggtctaggg aggaaggtta tcatttccca taagaaccct    29580
atgtggctag ctctcatcac agctacgtcc caagtcatat ctcacgactg tatgacctgc    29640
cctcgctgtt cttcctgcca gtgttgttta cactaaacaa gtctccaccc cttctctctc    29700
cgtcctcagg cattgctctt gtacttttcc attgtggaat ttcccgatct cataaacata    29760
gaatggactc aagtgttgaa tgtgtggttt cgagtctaac actaccctaa tgtggctgga    29820
ttttcaaagt tctttgccat ctctccaaca tgaatccaac ttgattttca agctttgcta    29880
ctgacatata aatcgagcct tgaataatat tttgtgtgct catccatgca tgcatggatc    29940
catggatcca atcatgtgtc caaccactca tccacccatc cgtgcatgca tccatctttc    30000
cgtcatgcat ttagacctta ctcagctcct gcttctgtga agaagcagcc atccctgtca    30060
tctaacaccc gaggtgcccc tcccccgcc acgttccat cttacagatc tcaccccact    30120
tcctccacaa tggcttcctg ctcatcatcc ttatagataa agatggaatc tttaagcgtc    30180
atatttctac ctgctcagcc ataacccata attgctgacc gagtgttgga tggatgaatg    30240
aattggttag gatgattctg ctattgttgt tttctggatg attctttctt gttttatagc    30300
taacctggga aaaaggtgg acttttacaa aaagccacag gttgcttggt gtttggacat    30360
tttcagattc ccttatctgt agcattttta cttcctactt tgagacacat gttgtaatgt    30420
ttatgcctta ctatcttcat ctgtcaaatg gaacaataaa tagttgtccc cagctctag     30480 gttaacgaga atggtgaaac ctgagctttt tttttttttt ttttttttt tgtgaaaatg     30540
```

-continued

```
actttggcac ttttagatgg ttcaaaatta gtagccagtt tatgagtgag ttgtacagtg    30600
acctctttat ccaacacagg aatgacgctc ccggcacaga agtgtgtgct ggaggcattc    30660
agagccagcg gagataacaa tattctgatt gctacctcgg tcgctgatga aggcattgac    30720
attgctgagt gcaatctcgt cattctctat gagtacgtgg gcaacgtcat caagatgatc    30780
caaaccagag gtgagagcgg ctgatgtcat tcccgccccg cacccgcttt tctcctttcc    30840
tcagctgtac catgtgattg acagcacagc tgactctggt actcgaaatc taaaagctga    30900
ctgccttggt caggattggg tggttatagg tttacccata atactccatt gcaactctcc    30960
acaatggtac tgcaatttta cccagcgttc aatggcatag tcgtgaaaat atcatatcca    31020
ctaggccaga ggctttgcca gtcggcaagt agaccttttga tgggtgtggt gagtagctct    31080
ctgtactcca gagtctggtc ccacctgaac cagagtctga cttcctttcc ctttcttgtt    31140
tccccaagaa cagcccccac attccctttc cggaataacg tctctgtgcc tgtcactcat    31200
cagtcacatc cattttttcgt cctcctccac cgcttactgt gcggttcagc cagccagact    31260
ccgcttcctg ctcgtccagt ttctcagata ctgtcgctct acatgttagg tcctatctct    31320
gtctctgcca cacacaacct aattcttcta cctagaacaa gcactccttt aaatgcccac    31380
taccgtttat atctgtctct gcaagagcat gacaattgca ttccttttctc cgcattgcag    31440
aagggtcagg tgcgcgtgca cggtgccact gctgcgggct catgccagat tatctgtaaa    31500
ttagtgttgc tggcagtgca gagcaatcag actatgccat tggagacccc atgaaaactg    31560
ccagagatgg cttatctgtg tgctgagcac actggctaga acctgcattt gagtctactc    31620
ttcggttcag cttccctaga aagtaggatg cagtgaatca aagttgaact cgagaaatac    31680
tcctcacatc tctttccagt aacctcagag tttgacatta acacacaaag aaaacgtttt    31740
ctgcaggccg aggaagagca cgagatagca agtgcttcct cctgaccagc agcgctgacg    31800
tgattgaaaa agaaaaggcg aacatgatca aggaaaaaat aatgaatgaa tccatcttaa    31860
gactgcagac atgggatgaa atgaaatttg gaaagacggt aagtctcttt ttctgtgcta    31920
ctcttatgga atctgactag aaataacaaa tgaccatggt tggtcctgag tgtgtgtgtg    31980
tgtgtgtgtg tggtatgtgt ttgtggccat gtgcattttat ttatctttgt gtgctagttt    32040
tggccattca ataaccttt ctgttcgcat gtaggttcac cgcatacagg tgaatgaaaa    32100
actcctcaga gacagtcagc acaaaccaca acctgttcct gacaaagaaa acaagaaact    32160
gctgtgtgga aagtgcaaga attttgcgtg ctacacagct gacattcgag tggttgaggt    32220
gagtggccct ggtgatttag caccggttaa atcttaccat cttccggaga aatggttgta    32280
gcaagaacac tatgttgtgg ggtttcgagt gttgaccatg gtcctgtatt aagaaataaa    32340
atcctgctag gtggtggtgg cacacgcctt taatcccagt acttgggagg cagaggcagg    32400
cggatttctg agttcgaggc cagcctggtc tacagggtga gttccaggac agccagggct    32460
acacagagaa accctgtctt ggaaaaacca aaaaaaaaaa aaaaaaaaag aaataaaatc    32520
ctgcttctat gtgggaacca gaaaggctga tgttatttaa gtccaaaaca gaaatggtg    32580
cttaacggcg agaagaggag gggggtctaa ttgtagctgc cccagacagt caggcaggat    32640
ggataaggtt tcccgttcca ctgcacagca gggtgaatac tgcttatagt ttctgattca    32700
ttacaactct tacaaagaat tagacgagag gaattcatag cttcagacat aaagagatga    32760
aaactgtcca ggcagaaggg aatgctaatt actctggcga gatcattaga tacttagaaa    32820
ttatcacact gcacaccta agtgaggaca actgtgtgct ttgaaagaca gtctcactca    32880
gaccaggctg gcttcaactt gagattcttc tgtgactcag cctccccagt gcaggggactc    32940
```

```
taggcatgca ccaccactct ctccaaagag atagtttttc ccagtgcagg gatagaaaat    33000
gaaggctctg ctagatacag tgttatgtcc ttggttagtt ccagggagga ggaagggcta    33060
ggcataaaaa tctgtcattg atttcttagt tttaacaaat gtgcaactgc attcaaaatg    33120
gaactgggct aaaggcattt gcaaatcttc tgaggcatct ctgtaacttt actgtatgtc    33180
aaagattatg ccaaagaaat gttaaggctc tgattttgaa gtgtacatgg ttctagtata    33240
aacctgccag caaatgaatg gtaaagtggg aaaatactat gaatatgaaa ttataaagat    33300
gcttttgtta tggctacata caacatgagc agtgatatct ttgtcatgac caatgtgggt    33360
ccacctttcc taaggggaa aaaaggctaa tatataaaaa tgacatattc tgctagtgaa     33420
ttctctcttc ctgttttgtt ttctaaactt ccttattgga acagagaatg cttttataat    33480
gaaaacaaaa cacctcattt taaaaaatat aacacttgta ggttagcttt ctactttttc    33540
accccttaaa ctttttttt tttttttga cacaggatct ctctctatag cactgggtat     33600
cttgaaactc attatatgga gattcccttg tccctgcctc ccaaacgctg ggacgtaaag    33660
gcatgtacca ttacacaagg tcttcttaaa acttttaact aaggcaaaaa acctccagag    33720
acgaatcttg cagtcatcat tcctgctacc gatggcgggg gcagatggct gtgctagcta    33780
ggggaggggt acagtcctta ttatgagtga catccacttt ctgagtctga ttctttagat    33840
gcagaaggtc ctttcagctc caaattcaag gcttctcctt cccagtggcc tggagaacga    33900
gatgcttggt ctgcgcttgc gtctgtaggg tacactcttt tttttttaat tggatatttt    33960
ctttatttac ataaagaaca ccttcagttc ccctacactg gggcatctaa gccttcatag    34020
gaccaaggac ctctcttccc attgatgcat gacaaggcca tcctctgcaa cgcacgcagc    34080
tggagccatg tgtactcctt tgtggatggc ttagtcgctg ggagctcttg ggggactggt    34140
tggttgatat tgttttctc cctgtggggt tccttcagtt gtagggtact ctcttaagtc     34200
aagtctaagt ggggtctgtg gacagcatgg ctcctgagcc tgttcacaca catccctgt    34260 gaccctggg tgtcaccagc cctgtgcttt ggtgccttcc tggcctctgg tgaacttgaa     34320
ctttgtatgt gaactcctct ttgcttctga gttggaaagc tgggtttcct cctttctcag    34380
gtgccagacg cccaggaaat gggtcctaat cggcctgggg aagactgtct atatagtttt    34440 ttttttcttcc aacttgtaaa ataaatggga tcccactcat tcctgacttt tagctactga    34500
gtggcttcta agtcatttc agacccgttt ctaacattgt gcgctccatc tcttcctcct    34560
agacgtccca ctacactgtc cttggagacg cttttaagga gcgctttgtg tgtaagccac    34620
accctaaacc aaagatctat gacaattttg agaagaaagc aaagatattc tgcgccaaac    34680
agaactgtag ccacgactgg ggaattttg tgagatacaa gacgttcgag attccagtca     34740
taaaaattga aagtttcgtc gtggaagata ttgtgagcgg agttcagaac cggcactcaa    34800
agtggaagga ctttcatttt gaaaggatac agttcgatcc tgcagaaatg tccgtatgac    34860
ctcaggcttc tccgtctcgt gccgcaggga gccgtgcctt aagcatggag ttgatgagcc    34920
aatgctttct tacccaagct tgcacaatcc tttcttacac aagcctgcac tgtgttgaat    34980
gccagataac ctgactggtt ggtttcaagc tggtgctgtc cacacaaagc acacacgcct    35040
gaactgcggc gccgaatagt ttcttcacca ataactcata gcgtagccct tggccatggt    35100
ggggaggggt taaacttgtc ccttttacac ttttcagaac tgcccgacag gaacgtgca    35160 gccactcggt acaccgagac gcatgatggc tggcgtgctg gaagggttcc cgttctctgt    35220
ctgctcgatc tgctgtaagc tgccttttgcc cttaatgaca gtgcccttaa gaacagtgac   35280
ttagttcttt ttcaggccac cagactgact gccagatccc ttctgtccct tctgtccctt    35340
```

```
gcactgattc ctttccggat tgaccctgc caccctgtca ccctctgcag agtctcctgg    35400
tttctgtctc ttccttggtt tctttgctga ctcaaatttg gtagttgcaa ggttcagtat    35460
gcacacatat atatttaaaa tgacatataa tttaaaatgt aaaagactat agttgacagc    35520
tatgcttact gagatggtat ttctgttctg ttcattacta tacatcttac ccttgctctc    35580
atctgttctt ttaacttggg ccatttcccg tctttgaata gacatctcaa accctgtctg    35640
tatgtctgtc tgtttcccac ctgtttgaga cagggtctct ctgtagacca gaaactccat    35700
atgtagacta tgctggcctt gaactcacag atcccctgc ctctcaagtg ttgaaattaa     35760 aatcttttcac catgcctggc tctagctatt ttcaataaag gctcatgttt aaagtttgaa   35820
ctacttccaa ttcattccct gacgtggctt gttgttgttg tttacttttg gagacactgt    35880
tcctctctgt agccctggct gtgtagacca ggctgccctt ggtcacagag atctgccagc    35940
ttctgcctcc ggagcactga gattgaaggc ctgcatcacc atgcctggct tgcccttcct   36000
tcttaaacat tatatattca aatggcattt ccgtgtttct tctcaaggtg tgccagtgct    36060
tcagagagct tagtttgggg ttcttcagat caagagacaa gtgtctgagc gctgttactg    36120
ccaacagagc aaagtactct tcagttcagg gaaggaacag tgctggtttt gtaggcagta    36180
cagtggtttt aacaccttcc tagaacttac ttgtaattca tcagttgtag accatcaatg    36240
gcctaaacca aactgcagag atcatctgac cacataactc cccttccagg acatttacat   36300
ttgaagacta tcccaagccc acccagagca cagtgggtta cccaaactcc ccaggtcaac    36360
cctggaggtc aacagtatga catgggatag cacaccactt ctcacagatg cctagagaaa    36420
ttacccagca acataactct tgggggaaaa aacacctata gggattaggc ttttaattga    36480
tagaataggt agaaaaaaag atatgtagta gttcttgata gtggttactg gtaaaattct    36540
tagtgcaata aaatgaattt gccgagagct gactttcttt ttttttcttgt tttttgaga    36600 cagggtttct ctgtatagct ttggctgtcc tggaatgcac tctgtagtcc aggctggcct    36660
tcgaactcag aaatccgcct tcctctgcct cccaagtgtt gggattaaag gcgtgcgcca    36720
ccacgcctgg ctgagagctg actttcattt atgtcttta gtctatgttg cctttctttg     36780
ctgctacagt ttaagaactc tacagcttgt ataagatacc tactgaaat tatttgagaa    36840 aaaaaacttg taaacattac aataatttaa ttaattaaaaa atttatgtat tttatgtata   36900
tgggtgtttt tttctgcaag tctgtgtgca cattagaaga gggcattgga tcctctctat    36960
tgttatagtt ttatgctgct gctgttgttg ctgtgtgtgt gtgtgtgtgt gtgtgctatg    37020
aattgaactc aggaccctctg gaagagcagt cagtgctctt aactgctgag ctatctctcc    37080
agtcctggca atgataaatc agttgaagtg aaatagtcct ccccccccctt ttttttttt    37140 gccaatgggg aaaagcagac taaatctgag accaaatgaa gttttgagtt gtacactgac    37200
ttaagccact gccaagcata ccctggaatg gagcaaaccc tgggttacta agtactgaat    37260
gaatacaaca ggaaggtttt gagagatggg aaaatgcttg tctttggact tccctgatgg     37320
aagttgcatc tggactctcc catgagcaca tcaccagtcc ccactagagt cctcacaggt    37380
tgccatccat gtgtccttt tgaggctgag atacaacttg ttctgcaacc acagaccttg      37440
ctgttttgtg gtcagtattg gtatcatagc attttcatcc tgacctggag ccttcagtca    37500
aaggcctcat tgtgcagtaa ggacgctgga ctcctgactc ctatacttaa aacagacttg    37560
gtaatttcaa acaagtcaac cagatgccag tatttctgca tgcatgtctt gtgggatggt    37620
gttgtgaggt cccctgacag atgcactgag tggccaggga gacttttgta ccccttttcca    37680 ttttaacagc ccacgggtca ctgtgttgct tccatcatat taacatcaac ttgaaccagt    37740
```

-continued

```
ggttcctgaa acacttcagt tcattggacc ttgctaatta gcatcctgta aaaacccacc    37800
aacaaatatc aactagacag gtagaatcca agtgaactgt acactcctgg atcatgccag    37860
taactgtttt aataatacac cataaaatat aactacgact tcattttaca aatctgtgtt    37920
taataaacag gtacaggctt gttgggtgcg aacttttaaa actcctaata aaaatgccag    37980
ctatgattat ctttgtttat g                                             38001
```

<210> SEQ ID NO 12
<211> LENGTH: 3435
<212> TYPE: DNA
<213> ORGANISM: Rattus norvegicus
<220> FEATURE:
<221> NAME/KEY: CDS
<222> LOCATION: (370)..(1815)

<400> SEQUENCE: 12

```
cgtttgtagt gtcagccatc ccaattgcct gttccttctc tgtgggagtg gtgtctagac     60
agtccaggca gggtatgcta ggcaggtgcg ttttggttgc ctcagatcgc aacttgactc    120
cataacggtg accaaagaca aagaaggaa accagattaa aaagaaccgg acacagaccc    180
ctgcagaatc tggagcggcc gtggttgggg gcggggctac gacggggcgg actcgggggc    240
gtgggagggc ggggccgggg cggggcccgg agccggctgc ggttgcggtc cctgcgccgg    300
cggtgaaggc gcagcggcgg cgagtggcta ttgcaagcgt ttggataatg tgagacctgg    360 gatgcaggg atg tcg act atc tgc ccc cca cca tct cct gct gtt gcc aag     411
           Met Ser Thr Ile Cys Pro Pro Pro Ser Pro Ala Val Ala Lys
               1               5                  10 aca gag att gct tta agt ggt gaa tca ccc ttg ttg gcg gct acc ttt         459
Thr Glu Ile Ala Leu Ser Gly Glu Ser Pro Leu Leu Ala Ala Thr Phe
15                  20                  25                  30 gct tac tgg gat aat att ctt ggt cct aga gta agg cac att tgg gct         507
Ala Tyr Trp Asp Asn Ile Leu Gly Pro Arg Val Arg His Ile Trp Ala
                35                  40                  45 cca aag aca gac caa gta ctc ctc agt gat gga gaa atc act ttt ctt        555
Pro Lys Thr Asp Gln Val Leu Leu Ser Asp Gly Glu Ile Thr Phe Leu
            50                  55                  60 gcc aac cac act ctg aat gga gaa att ctt cgg aat gcg gag agt ggg        603
Ala Asn His Thr Leu Asn Gly Glu Ile Leu Arg Asn Ala Glu Ser Gly
65                  70                  75 gca ata gat gta aag ttt ttt gtc tta tct gaa aag ggc gtc att att        651
Ala Ile Asp Val Lys Phe Phe Val Leu Ser Glu Lys Gly Val Ile Ile
        80                  85                  90 gtt tca tta atc ttc gac ggg aac tgg aac gga gat cgg agc act tac        699
Val Ser Leu Ile Phe Asp Gly Asn Trp Asn Gly Asp Arg Ser Thr Tyr
95                  100                 105                 110 gga cta tca att ata ctg ccg cag acg gag ctg agt ttc tac ctc cca        747
Gly Leu Ser Ile Ile Leu Pro Gln Thr Glu Leu Ser Phe Tyr Leu Pro
                115                 120                 125 ctg cac aga gtg tgt gtt gac agg cta acg cac atc att cga aaa gga        795
Leu His Arg Val Cys Val Asp Arg Leu Thr His Ile Ile Arg Lys Gly
            130                 135                 140 agg ata tgg atg cac aag gaa aga caa gaa aat gtc cag aaa att gtc        843
Arg Ile Trp Met His Lys Glu Arg Gln Glu Asn Val Gln Lys Ile Val
145                 150                 155 ttg gaa ggc acc gag agg atg gaa gat cag ggt cag agt atc atc cct        891
Leu Glu Gly Thr Glu Arg Met Glu Asp Gln Gly Gln Ser Ile Ile Pro
160                 165                 170
```

```
atg ctt act ggg gag gtc atc cct gtg atg gag ctg ctt gcg tct atg     939
Met Leu Thr Gly Glu Val Ile Pro Val Met Glu Leu Leu Ala Ser Met
175                 180                 185                 190 aga tca cac agt gtt cct gaa gac ctc gat ata gct gat aca gta ctc     987
Arg Ser His Ser Val Pro Glu Asp Leu Asp Ile Ala Asp Thr Val Leu
            195                 200                 205 aat gat gat gac att ggt gac agc tgt cat gaa ggc ttt ctt ctc aat    1035
Asn Asp Asp Asp Ile Gly Asp Ser Cys His Glu Gly Phe Leu Leu Asn
                210                 215                 220 gcc atc agc tca cat ctg cag acc tgc ggc tgt tct gtg gtg gta ggc    1083
Ala Ile Ser Ser His Leu Gln Thr Cys Gly Cys Ser Val Val Val Gly
            225                 230                 235 agc agt gca gag aaa gta aat aag ata gta aga aca ctg tgc ctt ttt    1131
Ser Ser Ala Glu Lys Val Asn Lys Ile Val Arg Thr Leu Cys Leu Phe
240                 245                 250 ctg aca cca gca gag agg aag tgc tcc agg ctg tgt gaa gcc gaa tcg    1179
Leu Thr Pro Ala Glu Arg Lys Cys Ser Arg Leu Cys Glu Ala Glu Ser
255                 260                 265                 270 tcc ttt aaa tac gaa tct gga ctc ttt gta caa ggc ttg cta aag gat    1227
Ser Phe Lys Tyr Glu Ser Gly Leu Phe Val Gln Gly Leu Leu Lys Asp
                275                 280                 285 gcg act ggc agt ttt gta cta cct ttc cgg caa gtt atg tat gcc cct    1275
Ala Thr Gly Ser Phe Val Leu Pro Phe Arg Gln Val Met Tyr Ala Pro
            290                 295                 300 tat ccc acc aca cac atc gat gtg gat gtc aac act gtc aag cag atg    1323
Tyr Pro Thr Thr His Ile Asp Val Asp Val Asn Thr Val Lys Gln Met
            305                 310                 315 cca ccg tgt cat gaa cat att tat aat caa cgc aga tac atg agg tca    1371
Pro Pro Cys His Glu His Ile Tyr Asn Gln Arg Arg Tyr Met Arg Ser
320                 325                 330 gag ctg aca gcc ttc tgg agg gca act tca gaa gag gac atg gct cag    1419
Glu Leu Thr Ala Phe Trp Arg Ala Thr Ser Glu Glu Asp Met Ala Gln
335                 340                 345                 350 gac acc atc atc tac aca gat gag agc ttc act cct gat ttg aat att    1467
Asp Thr Ile Ile Tyr Thr Asp Glu Ser Phe Thr Pro Asp Leu Asn Ile
                355                 360                 365 ttc caa gat gtc tta cac aga gac act cta gtg aaa gcc ttt ctg gat    1515
Phe Gln Asp Val Leu His Arg Asp Thr Leu Val Lys Ala Phe Leu Asp
            370                 375                 380 cag gtc ttc cat ttg aag cct ggc ctg tct ctc agg agt act ttc ctt    1563
Gln Val Phe His Leu Lys Pro Gly Leu Ser Leu Arg Ser Thr Phe Leu
            385                 390                 395 gca cag ttc ctc ctc att ctt cac aga aaa gcc ttg aca cta atc aag    1611
Ala Gln Phe Leu Leu Ile Leu His Arg Lys Ala Leu Thr Leu Ile Lys
400                 405                 410 tac ata gag gat gac acg cag aag ggg aaa aag ccc ttt aag tct ctt    1659
Tyr Ile Glu Asp Asp Thr Gln Lys Gly Lys Lys Pro Phe Lys Ser Leu
415                 420                 425                 430 cgg aac ctg aag ata gat ctt gat tta aca gca gag ggc gac ctt aac    1707
Arg Asn Leu Lys Ile Asp Leu Asp Leu Thr Ala Glu Gly Asp Leu Asn
                435                 440                 445 ata ata atg gct cta gct gag aaa att aag cca ggc cta cac tct ttc    1755
Ile Ile Met Ala Leu Ala Glu Lys Ile Lys Pro Gly Leu His Ser Phe
            450                 455                 460 atc ttc ggg aga cct ttc tac act agt gtc caa gaa cgt gat gtt cta    1803
Ile Phe Gly Arg Pro Phe Tyr Thr Ser Val Gln Glu Arg Asp Val Leu
            465                 470                 475 atg act ttt taa acatgtggtt tgctccgtgt gtctcatgac agtcacactt        1855
Met Thr Phe
    480
```

```
gctgttacag tgtctcagcg ctttggacac atccttcctc cagggtcctg ccgcaggaca    1915
cgttacacta cacttgtcag tagaggtctg taccagatgt caggtacatc gttgtagtga    1975
atgtctcttt tcctagacta gatgtaccct cgtagggact tatgtttaca accctcctaa    2035
gtactagtgc tgtcttgtaa ggatacgaat gaagggatgt aaacttcacc acaactgctg    2095
gttggttttg ttgttttttgt tttttgaaac ttataattca tggtttacat gcatcacact    2155
gaaaccctag ttagcttttt acaggtaagc tgtgagttga ctgcctgtcc ctgtgttctc    2215
tggcctgtac gatctgtggc gtgtaggatc acttttgcaa caactaaaaa ctaaagcact    2275
ttgtttgcag ttctacagaa agcaacttag tctgtctgca gattcgtttt tgaaagaaga    2335
catgagaaag cggagtttta ggtgaagtca gttgttggat cttcctttat agacttagtc    2395
ctttagatgt ggtctgtata gacatgccca accatcatgc atgggcactg aatatcgtga    2455
actgtggtat gctttttgtt ggtttattgt acttctgtca agaaagtgg cattggtttt    2515 tataattgtt gccaagtttt aaggttaatt ttcattattt ttgagccaaa ttaaaatgtg    2575
cacctcctgt gcctttccca atcttggaaa atataaattc ttggcagaag gtcagatttc    2635
agggcccagt cactttcgtc tgacttccct ttgcacagtc cgccatgggc ctggcttaga    2695
agttcttgta aactatgcca gagagtacat tcgctgataa aatcttcttt gcagagcagg    2755
agagcttctt gcctctttcc tttcatttct gcctggactt tggtgttctc cacgttccct    2815
gcatcctaag gacagcagga gaactctgac cccagtgcta tttctctagg tgctattgtg    2875
gcaaactcaa gcggtccgtc tctgtccctg taacgttcgt accttgctgg ctgtgaagta    2935
ctgactggta aagctccgtg ctacagcagt gtagggtata cacaaacaca agtaagtgtt    2995
ttatttaaaa ctgtggactt agcataaaaa gggagactat atttattttt tacaaaaggg    3055
ataaaaatgg aacccttttcc tcacccacca gatttagtca gaaaaaaaca ttctattctg    3115
aaaggtcaca gtggttttga catgacacat cagaacaacg cactctgtcc atgatggctt    3175
atgaactcca agtcactcca tcatggtaaa tgggtagatc cctccttcta gtgtgccaca    3235
ccattgcttc ccacagtaga atcttattta agtgctaagt gttgtctctg ctggtttact    3295
ctgttgtttt agagaatgta agttgtatag tgaataagtt attgaagcat gtgtaaacac    3355
tgttatacat cttttctcct agatggggaa tttggaataa ataccttta aaattcaaaa    3415 aaaaaaaaa aaaaaaaaa                                                   3435
```

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

```
<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 15, 16, 17, 18, 19
<223> OTHER INFORMATION: bases at these positions are RNA

<400> SEQUENCE: 20
cccautccag tttccauca                                              19

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 6, 17, 18, 19, 20, 21
<223> OTHER INFORMATION: bases at these positions are RNA

<400> SEQUENCE: 21
gcggcutgtt tccctccuug u                                           21

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 16, 17, 18, 19, 20
<223> OTHER INFORMATION: bases at these positions are RNA

<400> SEQUENCE: 22
gccccggccc ctagcgcgcg                                             20
```

```
<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 16, 17, 18, 19, 20
<223> OTHER INFORMATION: bases at these positions are RNA

<400> SEQUENCE: 23
cccgaccacg ccccggcccc                                               20

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 16, 17, 18, 19
<223> OTHER INFORMATION: bases at these positions are RNA

<400> SEQUENCE: 24
agccaccttc tccaaccug                                                19

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gccttactct aggaccaaga                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ggtaacttca aactcttggg                                               20
```

```
<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
tacaggctgc ggttgtttcc                                              20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ccggccccgg ccccggcccc                                              20
```

METHODS FOR MONITORING C9ORF72 EXPRESSION

SEQUENCE LISTING

The present application is being filed along with a Sequence Listing in electronic format. The Sequence Listing is provided as a file entitled BIOL0215USASEQ_ST25.txt created Apr. 15, 2015, which is 134 Kb in size. The information in the electronic format of the sequence listing is incorporated herein by reference in its entirety.

FIELD

Provided are methods for reducing expression of C9ORF72 mRNA and protein in an animal. Such methods are useful to treat, prevent, or ameliorate neurodegenerative diseases, including amyotrophic lateral sclerosis (ALS), frontotemporal dementia (FTD), corticalbasal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hintz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The chromosome 9p21ALS-FTD locus in the last major autosomal-dominant gene whose mutation is causative of ALS. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Disclosed herein are biomarkers and methods for monitoring expression of C9ORF72 mRNA and protein in an animal with C9ORF72 specific inhibitors. Such C9ORF72 specific inhibitors include antisense compounds.

Provided herein are methods for modulating levels of C9ORF72 mRNA and protein in cells, tissues, and animals. In certain embodiments, C9ORF72 specific inhibitors modulate expression of C9ORF72 mRNA and protein. In certain embodiments, C9ORF72 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 mRNA levels are reduced. In certain embodiments, C9ORF72 protein levels are reduced. In certain embodiments, certain C9ORF72 mRNA variants are preferentially reduced. In certain embodiments, the C9ORF72 mRNA variants preferentially reduced are variants containing intron 1. In certain embodiments, intron 1 contains a hexanucleotide repeat expansion. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats. In certain embodiments, the hexanucleotide repeat expansion is associated with nuclear foci. In certain embodiments, the hexanucleotide repeat expansion is associated with misregulated expression of various genes. In certain embodiments, the hexanucleotide repeat expansion is associated with nuclear retention of various proteins. In certain embodiments, the methods described herein are useful for reducing C9ORF72 mRNA, C9ORF72 protein levels, and nuclear foci. Such reduction can occur in a time-dependent manner or in a dose-dependent manner. In certain embodiments, the methods described herein are useful for normalizing expression of various genes and reducing nuclear retention of various proteins.

Also provided are methods useful for preventing, treating, and ameliorating diseases, disorders, and conditions associated with C9ORF72. In certain embodiments, such diseases, disorders, and conditions associated with C9ORF72 are neurodegenerative diseases. In certain embodiments, the neurodegenerative disease is ALS, FTD, corticalbasal degeneration syndrome (CBD), atypical Parkinsonian syndrome, and olivopontocerellar degeneration (OPCD).

Such diseases, disorders, and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 specific inhibitor to an individual in need thereof. In certain embodiments, the C9ORF72 specific inhibitor is a nucleic acid. In certain embodiments, the nucleic acid is an antisense compound. In certain embodiments, the antisense compound is a single-stranded antisense oligonucleotide. In certain embodiments, the single-stranded antisense oligonucleotide is complementary to a C9ORF72 nucleic acid.

BRIEF DESCRIPTION OF THE FIGURES

FIG. 1a is a diagram presenting the targeting regions of ASOs 1-5 with respect to the C9ORF72 mRNA variant 1, GENBANK Accession No. NM_145005.4 (designated herein as SEQ ID NO: 6) and mRNA variant 2, GENBANK Accession No. NM_018325.2 (designated herein as SEQ ID NO: 4).

FIG. 1b is a gel showing the total mRNA levels of C9ORF72.

FIG. 2a is a graph depicting C9ORF72 expression in treated and untreated cells.

FIG. 2b is a gel showing expression of ENPP2 mRNA and RSPO3 mRNA in treated and untreated cells.

FIG. 3a is a diagram showing where C9ORF72 ASO targets mRNA variant 1, GENBANK Accession No. NM 145005.4 (designated herein as SEQ ID NO: 6) and mRNA variant 2, GENBANK Accession No. NM 018325.2 (designated herein as SEQ ID NO: 4).

FIG. 3b is a gel depicting expression of C9ORF72 mRNA, C3 mRNA, EDNRB mRNA, and Endothelin mRNA in treated and untreated cells in control fibroblasts and C9ORF72 fibroblasts.

DETAILED DESCRIPTION

Figure 4A:
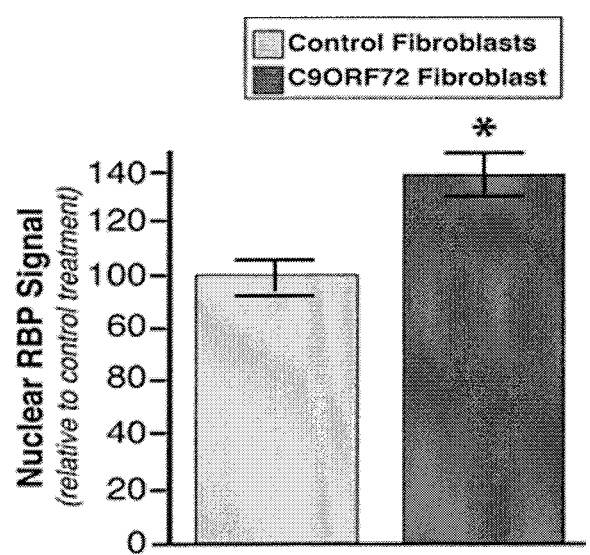
FIG. 4a is a graph showing nuclear retention of ADARB2 in human C9ORF72 fibroblasts and control fibroblasts.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl group" (also 2'-MOE and 2'-OCH$_2$CH$_2$—OCH$_3$ and MOE) refers to an O-methoxyethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-O-methoxyethyl group.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of C9ORF72", it is implied that the C9ORF72 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds. Antisense mechanisms include, without limitation, RNase H mediated antisense; RNAi mechanisms, which utilize the RISC pathway and include, without limitation, siRNA, ssRNA and microRNA mechanisms; and occupancy based mechanisms, including, without limitation uniform modified oligonucleotides. Certain antisense compounds may act through more than one such mechanisms and/or through additional mechanisms.

"Antisense inhibition" means reduction of target nucleic acid levels or target protein levels in the presence of an antisense compound complementary to a target nucleic acid compared to target nucleic acid levels or target protein levels in the absence of the antisense compound Inhibition may by any means including RNase H degradation, such as with a gapmer, and steric blockage/occupancy based mechanisms, such as with a uniformly modified oligonucleotide.

"Antisense oligonucleotide" means a single-stranded oligonucleotide having a nucleobase sequence that permits hybridization to a corresponding segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Biomarker" means a measurable substance in a cell or animal whose presence is indicative of some phenomenon such as disease. In certain embodiments, the substance is the RNA or protein expression product of a gene. In certain embodiments, the gene is any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, ZNF695, EDN1, NEDD4L, FAM3C, CHRDL1, CP, SEPP1, SERPINE2, and/or any other gene described herein. In certain embodiments, the disease is a C9ORF72 associated disease and/or a C9ORF72 hexanucleotide repeat expansion associated disease.

"C9ORF72 associated disease" means any disease associated with any C9ORF72 nucleic acid or expression product thereof. Such diseases may include a neurodegenerative disease. Such neurodegenerative diseases may include ALS and FTD.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise GGGGCC, GGGGGG, GGGGGC, or GGGGCG repeated at least 30 times. Such diseases may include a neurodegenerative disease. Such neurodegenerative diseases may include ALS and FTD.

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 (including genomic DNA comprising introns and exons), and an mRNA sequence encoding C9ORF72. "C9ORF72 mRNA" means an mRNA encoding a C9ORF72 protein.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of pharmaceutical agent sufficient to effectuate a desired physiological outcome in an individual in need of the pharmaceutical agent. The effective amount may vary among individuals depending on the health and physical condition of the individual to be treated, the taxonomic group of the individuals to be treated, the formulation of the composition, assessment of the individual's medical condition, and other relevant factors.

"Expression" means conversion of the information from a C9ORF72 gene into mRNA via transcription and then to protein via translation. Expression may result in a phenotypic manifestation of the C9ORF72 gene.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" (also $GGGGCC_{exp}$ RNA repeat) means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include an antisense compound and a target nucleic acid.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing expression of C9ORF72 mRNA and/or protein levels in the presence of a C9ORF72 specific inhibitor, including a C9ORF72 antisense oligonucleotide, as compared to expression of C9ORF72 mRNA and/or protein levels in the absence of a C9ORF72 specific inhibitor, such as a C9ORF72 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical agent" means the substance or substances in a pharmaceutical composition that provide a therapeutic benefit when administered to an individual. For example, in certain embodiments an antisense oligonucleotide targeted to C9ORF72 is a pharmaceutical agent.

"Pharmaceutical composition" means a mixture of substances suitable for administering to an individual. For example, a pharmaceutical composition may comprise one or more pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

CERTAIN EMBODIMENTS

Provided herein are biomarkers and methods for monitoring expression of a C9ORF72 nucleic acid and protein in an animal with C9ORF72 specific inhibitors. Such C9ORF72 specific inhibitors include antisense compounds. Such biomarkers may include any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, ZNF695, EDN1, NEDD4L, FAM3C, CHRDL1, CP, SEPP1, SERPINE2, and/or any other gene described herein.

Certain embodiments provide methods for decreasing C9ORF72 mRNA and protein expression.

Certain embodiments provide methods for the treatment, prevention, or amelioration of diseases, disorders, and conditions associated with C9ORF72 in an individual in need thereof. Also contemplated are methods for the preparation of a medicament for the treatment, prevention, or amelioration of a disease, disorder, or condition associated with C9ORF72. C9ORF72 associated diseases, disorders, and conditions include neurodegenerative diseases. In certain embodiments, the neurodegenerative disease may be ALS or FTD. In certain embodiments, the neurodegenerative disease may be familial or sporadic.

Certain embodiments provide for the use of a C9ORF72 specific inhibitor for treating, preventing, or ameliorating a C9ORF72 associated disease. Certain embodiments provide for the use of a C9ORF72 specific inhibitor for treating, preventing, or ameliorating a C9ORF72 hexanucleotide repeat expansion associated disease. In certain embodiments, the hexanucleotide repeat expansion may comprise GGGGCC, GGGGGG, GGGGGC, or GGGGCG. In certain embodiments, C9ORF72 specific inhibitors are nucleic acids (including antisense compounds), peptides, antibodies, small molecules, and other agents capable of inhibiting the expression of C9ORF72 mRNA and/or C9ORF72 protein.

Provided herein are methods comprising administering a C9ORF72 antisense compound to an animal for treating a C9ORF72 associated disease and thereby normalizing expression of any of EDN1, NEDD4L, FAM3C, CHRDL1, CP, SEPP1, and SERPINE2.

Described herein are methods comprising administering a C9ORF72 antisense compound to an animal for treating a C9ORF72 associated disease and thereby normalizing expression of any of C3, EDNRB2, and Endothelin.

Provided herein are methods comprising administering a C9ORF72 antisense compound to an animal for treating a C9ORF72 associated disease and thereby normalizing expression of any of EDN1, NEDD4L, FAM3C, CHRDL1, CP, SEPP1, and SERPINE2.

Described herein are methods comprising administering a C9ORF72 antisense compound to an animal for treating a C9ORF72 associated disease and thereby normalizing expression of any of ABCA6, ACVR2A, ADAMTS5, C11orf87, C3, CCL8, CCNL1, CD44, CELF2, CFB, CHRDL1, CLU, CP, CXCL6, DCN, DKK3, EDN1, EDNRB, EFNA5, ENPP2, F10, F3, FAM3C, FOXP2, FYN, IARS, IGSF10, IL6ST, LPAR1, MLXIPL, NEDD4L, ORC4, PDE1C, PPAP2B, PRPS1, REV3L, RSPO3, SCUBE3, SEPP1, SERPINE2, SESTD1, SPON1, TBC1D15, TGFBR3, TNFSF10, TNFSF13B, and WDR52.

Described herein are methods comprising administering a C9ORF72 antisense compound to an animal for treating a C9ORF72 associated disease and thereby normalizing expression of any of ABCA6, ABCA9, ABCB4, ABCC3, ABCC9, ABO, ACAN, ACOT13, ACSM2A, ACSS3, ACVR2A, ACVR2B, ADAMDEC1, ADAMTS5, ADH1A, ADH1B, ADH1C, ADM, AFF3, AGBL3, AHNAK2, AK4, ALDH1A3, ALDH1L2, ALMS1P, ALOX5AP, AMOT, AMPH, ANKRD32, ANLN, ANO3, ANO4, AOX1, APCDD1, APLNR, APOBEC3B, APOL6, APOLD1, AR, ARHGAP11A, ARHGAP28, ARHGAP29, ARHGEF35, ARL17A, ARL4D, ARMS2, ARNT2, ARRDC3, ARSE, ARVP6125, ATOH8, ATP2A2, AURKA, AURKB, BACH1, BAMBI, BCL3, BDH2, BICC1, BNC2, BRCA2, BRIP1, BRWD3, BTF3L4, BUB1, BUB1B, C11orf87, C12orf48, C12orf64, C13orf18, C14orf149, C15orf42, C1orf191, C1orf198, C1orf63, C1QB, C1R, C1S, C2orf63, C3, C3orf16, C3orf31, C3orf59, C4orf29, C4orf31, C4orf49, C5orf13, C5orf23, C6orf105, C6orf223, C1orf63, C9, CA12, CA13, CACHD1, CADPS, CASC5, CASP10, CBWD1, CCDC144B, CCDC144C, CCDC15, CCIN, CCL28, CCL8, CCNA2, CCNB1, CCNB2, CCNF, CCNL1, CCRL1, CD4, CD68, CDC20, CDC25B, CDC45, CDC6, CDC7, CDCA2, CDCA3, CDCA8, CDH6, CDHR4, CDK1, CDK15, CDK2, CDON, CELF2, CENPA, CENPE, CENPF, CENPI, CENPK, CEP55, CFB, CGB, CGB1, CGB5, CH25H, CHRDL1, CHRNA5, CKAP2L, CKS2, CLDN11, CLEC2A, CLGN, CLIC2, CLIC6, CLSPN, CMKLR1, CNKSR2, CNN1, CNR2, CNTNAP3, COL8A1, COLEC12, COMP, CP, CPA4, CPE, CPLX2, CPM, CPXM1, CRABP2, CRISPLD2, CRY1, CTAGE7P, CTNNBIP1, CTSC, CTSL1, CTSS, CXCL14, CXCL6, CXCR7, CYB5A, CYBB, CYP1B1, CYP24A1, CYP26B1, CYP27A1, CYP3A43, CYP7B1, CYTL1, CYYR1, DBF4, DCDC1, DCN, DDIT3, DDIT4, DEFB109P1B, DENND1B, DEPDC1, DES, DGCR14, DHRS3, DIRC1, DKFZp566F0947, DKFZp667F0711, DKK1, DKK3, DLGAP5, DLX2, DMKN, DNA2, DPP4, DPT, DSEL, DTX3L, DTYMK, E2F8, EDN1, EDNRB, EFEMP1, EFNA5, ELL2, EMCN, EMP1, ENKUR, ENPEP, ENPP2, ENPP5, EPB41L4A, EPSTI1, ERCC6, ERCC6L, EREG, ESM1, ETFDH, F10, F2R, F2RL2, F3, FABP3, FAM101B, FAM110B, FAM156A, FAM20A, FAM3C, FAM43A, FAM46C, FAM59A, FAM71A, FAM75C1, FAM83D, FBLN1, FCER1G, FCGR2A, FDPSL2A, FER, FGD4, FIBIN, FKBP14, F1110038, FLJ31356, FLJ39095, FLJ39739, FLJ41170, FLRT3, FMN1, FOLR2, FOLR3, FOSL2, FOXC2, FOXE1, FOXP2, FRRS1, FTLP10, FUT9, FYN, G0S2, GABRE, GABRQ, GEMC1, GFRA1, GLDN, GLIPR2, GLIS3, GOLGA6B, GPNMB, GPR133, GPR31, GPR65, GPRC5B, GRB14, GSTT1, GSTT2, GTPBP8, GTSE1, GUCY1B3, HAS2, HAUS3, HECW2, HELLS, HIST1H1B, HIST1H2AE, HIST1H2AJ, HIST1H2BF, HIST1H2BM, HIST1H3B, HIST1H3J, HIST1H4A, HIST1H4C, HIST1H4D, HIST1H4L, HIST2H2BC, HIST2H3A, HJURP, HMGB2, HMMR, HNRNPK, HOXB2, HOXD10, HOXD11, HSD17B7P2, HTR1B, HUNK, IARS, ICAM1, IDH1, IFI16, IFITM1, IFITM3, IGF1, IGSF10, IL13RA2, IL17RA, IL17RD, IL18R1, IL1R1, IL1RN, IL20RB, IL4R, IL6ST, IQGAP3, IRS1, ITGA6, ITGA8, ITGB3, ITGBL1, JAG1, JAM2, KCNJ2, KCNJ8, KCNK15, KIAA0509, KIAA0802, KIAA1199, KIAA1324L, KIAA1524, KIF11, KIF14, KIF15, KIF16B, KIF18B, KIF20A, KIF20B, KIF23, KIF2C, KIF4A, KIFC1, KIT, KRT19, KRT34, KRTAP1-1, KRTAP1-5, KRTAP2-2, KRTAP2-4, KRTAP4-11, KRTAP4-12, KRTAP4-5, KRTAP4-7, LAMA1, LAMA4, LANCL3, LAP3, LAPTM5, LARP7, LBR, LGI1, LHX5, LHX9, LMCD1, LMNB1, LMO4, LOC100127980, LOC100128001, LOC100128107, LOC100128191, LOC100128402, LOC100129029, LOC100130000, LOC100132167, LOC100132292, LOC100132891, LOC100216479, LOC100287877, LOC100288069, LOC100288560, LOC100505808, LOC100505813, LOC100505820, LOC100506165, LOC100506335, LOC100506456, LOC100507128, LOC100507163, LOC100507425, LOC116437, LOC144438, LOC153910, LOC157503, LOC256374, LOC283868, LOC285944, LOC338667, LOC339822, LOC348120, LOC349408, LOC389332, LOC399884, LOC400684, LOC401022, LOC642006, LOC643551, LOC646743, LOC646804, LOC727820, LOC728264, LOC728640, LOC729420, LOC729978, LOH3CR2A, LOXL4, LPAR1, LRCH2, LRIG3, LRRC37A4, LRRTM1, LYPD6B, MAB21L1, MAFB, MAOA, MAPK13, MARS, MASP1, MASTL, MBD2, MBNL3, MC4R, MCM8, ME2, MEIS3P1, MEST, METTL8, MEX3A, MFAP4, MFGE8, MGC16121, MGC24103, MGP, MIA3, MIER1, MIR125A, MIR138-1, MIR145, MIR199A2, MIRLET7I, MKI67, MLF2, MMD, MME, MMP10, MMP12, MMP27, MOBKL1B, MRAP2, MRPL9, MRPS11, MSC, MST4, MSTN, MTMR7, MTSS1L, MTUS2, MYBL2, MYCT1, MYOCD, MYPN, MZT2A, NACA2, NAIP, NAMPT, NAP1L3, NBEA, NBPF10, NCAPG, NCAPG2, NCAPH, NCRNA00182, NCRNA00205, NCRNA00219, NCRNA00256A, NDC80, NEDD4L, NEK2, NETO2, NEU4, NEUROD6, NFIB, NFIL3, NFKBIZ, NGFR, NKX2-2, NKX2-6, NNMT, NOC2L, NOG, NOTCH3, NOVA1, NOX4, NPTX2, NR2F2, NR4A3, NR5A2, NTN4, NUCKS1, NUF2, NUSAP1, NUTF2, OAS2, OAS3, OBFC2A, OCLM, ODZ2, OGFRL1, OLFML2B, OLR1, OR10Q1, OR14J1, OR1J2, OR1Q1, OR2A1, OR2A7, OR2A9P, OR2B3, OR4D10, OR4L1, OR51A2, OR52W1, OR5AU1, OR5L2, OR6B1, ORC4, OSMR, OSR2, OXTR, P2RX7, PACSIN2, PAPPA, PARP14, PBK, PCDHB13, PCDHB14, PCDHB16, PCDHB2, PCDHB3, PCDHB4, PCYT2, PDE1C, PDE4DIP, PDE5A, PDGFA, PDGFD, PDPN, PDZRN3, PEG10, PHACTR3, PHF11, PHLDB2, PIM1, PITPNM3, PKD2L1, PKDCC, PLA2G4A, PLEKHA3, PLK1, PLK4, PLSCR1, PLXNA2, PLXNC1, PM20D2, PMAIP1, PPAP2B, PPL, PPP1R12B, PRAMEF2, PRC1, PRDM1, PRDM15, PRG4, PRICKLE1, PRICKLE2, PRKAA2, PRKG2, PRPS1, PRUNE2, PRY, PSIP1, psiTPTE22, PTBP2, PTGS1, PTPRC, PTPRN, PYGO1, RAB12, RAD51AP1, RASA4, RASGRF2, RBMS1, RBMX2, RCVRN, RERGL, REV3L, RGPD1, RGPD2, RGPD6, RGS4, RHBDF1, RHOJ, RIMS1, RIPK2, RNASE2, RNF122, RNU2-1, RPL22L1, RPL8, RPRD1A, RPRM, RPS26P11, RPS6KA6, RPS8, RPSAP52, RRP15, RSPO3, RUNX1T1, S100A8, S1PR1, SCIN, SCN2A, SCUBE3, SEPP1, SERPINB3, SERPINB4, SERPINB9, SERPINE2, SERPINF1, SERPING1, SESTD1, SFRP1, SFRP4, SGK1, SGOL1, SGOL2, SHCBP1, SHMT1, SKA1, SKA3, SKIL, SLC1A3, SLC39A8, SLC40A1, SLC43A3, SLC6A15, SLFN11, SLITRK4, SMAD4, SMC4, SNHG1, SNORD32B, SOCS5, SPC24, SPC25, SPDYE8P, SPON1, SRD5A1P1, SRGAP1, SRGN, SRSF10, SSPN, SSTR1, SSX5, ST6GALNAC5, ST8SIA2, STC1, STEAP1, STEAP2, STEAP4, STOM, SV2A, SVEP1, SYNPR, TACC2, TAGLN, TAS2R10, TBC1D15, TBC1D2, TBX3, TEK, TES, TFAP2A, TFPI, TFPI2, TGFBR3, TGOLN2, THAP2, THBS2, THRB, THSD7A, TINAGL1, TLE3, TLE4, TLN2, TLR1, TLR4, TLR5, TLR6, TLR7, TM4SF18, TMEM119, TMEM135, TMEM155, TMEM30B, TMEM49, TMEM65, TMTC1, TNC, TNFAIP3, TNFRSF10C, TNFRSF11B, TNFSF10, TNFSF13B, TNIK, TOP2A, TOR1AIP1, TOX, TPI1, TPM2, TPM3, TPX2, TRA2B, TRAF3IP2, TRIM24, TRIM36, TRIM43, TRIM64, TROAP, TSIX, TTC22, TTK, UBE2C, UHRF1, UNC5B, USP8, VEGFA, VGLL3, VTI1B, VTRNA1-3, VWA5A, WDR17, WDR52, WEE1, WISP1, WISP2, WNT16, WNT2, WWC1, XAGE3, XPO4, ZC3H11A, ZC3H7B, ZDHHC15, ZFP36, ZFP82, ZMYM2, ZNF135, ZNF207, ZNF28, ZNF280B, ZNF284, ZNF285, ZNF322A, ZNF462, ZNF506, ZNF595, ZNF678, ZNF714, ZNF717, ZNF737, ZNF808, ZNHIT2, and ZWINT.

Described herein are methods comprising administering a C9ORF72 antisense compound to an animal for treating a C9ORF72 associated disease and thereby reducing nuclear retention of any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, ZNF695.

Described herein are methods, comprising identifying an animal having a C9ORF72 associated disease; and administering a C9ORF72 antisense compound and thereby normalizing expression of any of EDN1, NEDD4L, FAM3C, CHRDL1, CP, SEPP1, and SERPINE2.

Described herein are methods identifying an animal having a C9ORF72 associated disease; and administering a C9ORF72 antisense compound and thereby normalizing expression of any of C3, EDNRB2, and Endothelin.

Described herein are methods comprising, identifying an animal having a C9ORF72 associated disease; and administering a C9ORF72 antisense compound and thereby normalizing expression of any of ABCA6, ACVR2A, ADAMTS5, C11orf87, C3, CCL8, CCNL1, CD44, CELF2, CFB, CHRDL1, CLU, CP, CXCL6, DCN, DKK3, EDN1, EDNRB, EFNA5, ENPP2, F10, F3, FAM3C, FOXP2, FYN, IARS, IGSF10, IL6ST, LPAR1, MLXIPL, NEDD4L, ORC4, PDE1C, PPAP2B, PRPS1, REV3L, RSPO3, SCUBE3, SEPP1, SERPINE2, SESTD1, SPON1, TBC1D15, TGFBR3, TNFSF10, TNFSF13B, and WDR52.

Described herein are methods comprising, identifying an animal having a C9ORF72 associated disease; and administering a C9ORF72 antisense compound and thereby normalizing expression of any of ABCA6, ABCA9, ABCB4, ABCC3, ABCC9, ABO, ACAN, ACOT13, ACSM2A, ACSS3, ACVR2A, ACVR2B, ADAMDEC1, ADAMTS5, ADH1A, ADH1B, ADH1C, ADM, AFF3, AGBL3, AHNAK2, AK4, ALDH1A3, ALDH1L2, ALMS1P, ALOX5AP, AMOT, AMPH, ANKRD32, ANLN, ANO3, ANO4, AOX1, APCDD1, APLNR, APOBEC3B, APOL6, APOLD1, AR, ARHGAP11A, ARHGAP28, ARHGAP29, ARHGEF35, ARL17A, ARL4D, ARMS2, ARNT2, ARRDC3, ARSE, ARVP6125, ATOH8, ATP2A2, AURKA, AURKB, BACH1, BAMBI, BCL3, BDH2, BICC1, BNC2, BRCA2, BRIP1, BRWD3, BTF3L4, BUB1, BUB1B, C11orf87, C12orf48, C12orf64, C13orf18, C14orf149, C15orf42, C1orf191, C1orf198, C1orf63, C1QB, C1R, C1S, C2orf63, C3, C3orf16, C3orf31, C3orf59, C4orf29, C4orf31, C4orf49, C5orf13, C5orf23, C6orf105, C6orf223, C1orf63, C9, CA12, CA13, CACHD1, CADPS, CASC5, CASP10, CBWD1, CCDC144B, CCDC144C, CCDC15, CCIN, CCL28, CCL8, CCNA2, CCNB1, CCNB2, CCNF, CCNL1, CCRL1, CD4, CD68, CDC20, CDC25B, CDC45, CDC6, CDC7, CDCA2, CDCA3, CDCA8, CDH6, CDHR4, CDK1, CDK15, CDK2, CDON, CELF2, CENPA, CENPE, CENPF, CENPI, CENPK, CEP55, CFB, CGB, CGB1, CGB5, CH25H, CHRDL1, CHRNA5, CKAP2L, CKS2, CLDN11, CLEC2A, CLGN, CLIC2, CLIC6, CLSPN, CMKLR1, CNKSR2, CNN1, CNR2, CNTNAP3, COL8A1, COLEC12, COMP, CP, CPA4, CPE, CPLX2, CPM, CPXM1, CRABP2, CRISPLD2, CRY1, CTAGE7P, CTNNBIP1, CTSC, CTSL1, CTSS, CXCL14, CXCL6, CXCR7, CYB5A, CYBB, CYP1B1, CYP24A1, CYP26B1, CYP27A1, CYP3A43, CYP7B1, CYTL1, CYYR1, DBF4, DCDC1, DCN, DDIT3, DDIT4, DEFB109P1B, DENND1B, DEPDC1, DES, DGCR14, DHRS3, DIRC1, DKFZp566F0947, DKFZp667F0711, DKK1, DKK3, DLGAP5, DLX2, DMKN, DNA2, DPP4, DPT, DSEL, DTX3L, DTYMK, E2F8, EDN1, EDNRB, EFEMP1, EFNA5, ELL2, EMCN, EMP1, ENKUR, ENPEP, ENPP2, ENPP5, EPB41L4A, EPSTI1, ERCC6, ERCC6L, EREG, ESM1, ETFDH, F10, F2R, F2RL2, F3, FABP3, FAM101B, FAM110B, FAM156A, FAM20A, FAM3C, FAM43A, FAM46C, FAM59A, FAM71A, FAM75C1, FAM83D, FBLN1, FCER1G, FCGR2A, FDPSL2A, FER, FGD4, FIBIN, FKBP14, FLJ10038, FLJ31356, FLJ39095, FLJ39739, FLJ41170, FLRT3, FMN1, FOLR2, FOLR3, FOSL2, FOXC2, FOXE1, FOXP2, FRRS1, FTLP10, FUT9, FYN, G0S2, GABRE, GABRQ, GEMC1, GFRA1, GLDN, GLIPR2, GLIS3, GOLGA6B, GPNMB, GPR133, GPR31, GPR65, GPRC5B, GRB14, GSTT1, GSTT2, GTPBP8, GTSE1, GUCY1B3, HAS2, HAUS3, HECW2, HELLS, HIST1H1B, HIST1H2AE, HIST1H2AJ, HIST1H2BF, HIST1H2BM, HIST1H3B, HIST1H3J, HIST1H4A, HIST1H4C, HIST1H4D, HIST1H4L, HIST2H2BC, HIST2H3A, HJURP, HMGB2, HMMR, HNRNPK, HOXB2, HOXD10, HOXD11, HSD17B7P2, HTR1B, HUNK, IARS, ICAM1, IDH1, IFI16, IFITM1, IFITM3, IGF1, IGSF10, IL13RA2, IL17RA, IL17RD, IL18R1, IL1R1, IL1RN, IL20RB, IL4R, IL6ST, IQGAP3, IRS1, ITGA6, ITGA8, ITGB3, ITGBL1, JAG1, JAM2, KCNJ2, KCNJ8, KCNK15, KIAA0509, KIAA0802, KIAA1199, KIAA1324L, KIAA1524, KIF11, KIF14, KIF15, KIF16B, KIF18B, KIF20A, KIF20B, KIF23, KIF2C, KIF4A, KIFC1, KIT, KRT19, KRT34, KRTAP1-1, KRTAP1-5, KRTAP2-2, KRTAP2-4, KRTAP4-11, KRTAP4-12, KRTAP4-5, KRTAP4-7, LAMA1, LAMA4, LANCL3, LAP3, LAPTM5, LARP7, LBR, LGI1, LHX5, LHX9, LMCD1, LMNB1, LMO4, LOC100127980, LOC100128001, LOC100128107, LOC100128191, LOC100128402, LOC100129029, LOC100130000, LOC100132167, LOC100132292, LOC100132891, LOC100216479, LOC100287877, LOC100288069, LOC100288560, LOC100505808, LOC100505813, LOC100505820, LOC100506165, LOC100506335, LOC100506456, LOC100507128, LOC100507163, LOC100507425, LOC116437, LOC144438, LOC153910, LOC157503, LOC256374, LOC283868, LOC285944, LOC338667, LOC339822, LOC348120, LOC349408, LOC389332, LOC399884, LOC400684, LOC401022, LOC642006, LOC643551, LOC646743, LOC646804, LOC727820, LOC728264, LOC728640, LOC729420, LOC729978, LOH3CR2A, LOXL4, LPAR1, LRCH2, LRIG3, LRRC37A4, LRRTM1, LYPD6B, MAB21L1, MAFB, MAOA, MAPK13, MARS, MASP1, MASTL, MBD2, MBNL3, MC4R, MCM8, ME2, MEIS3P1, MEST, METTLE, MEX3A, MFAP4, MFGE8, MGC16121, MGC24103, MGP, MIA3, MIER1, MIR125A, MIR138-1, MIR145, MIR199A2, MIRLET7I, MKI67, MLF2, MMD, MME, MMP10, MMP12, MMP27, MOBKL1B, MRAP2, MRPL9, MRPS11, MSC, MST4, MSTN, MTMR7, MTSS1L, MTUS2, MYBL2, MYCT1, MYOCD, MYPN, MZT2A, NACA2, NAIP, NAMPT, NAP1L3, NBEA, NBPF10, NCAPG, NCAPG2, NCAPH, NCRNA00182, NCRNA00205, NCRNA00219, NCRNA00256A, NDC80, NEDD4L, NEK2, NETO2, NEU4, NEUROD6, NFIB, NFIL3, NFKBIZ, NGFR, NKX2-2, NKX2-6, NNMT, NOC2L, NOG, NOTCH3, NOVA1, NOX4, NPTX2, NR2F2, NR4A3, NR5A2, NTN4, NUCKS1, NUF2, NUSAP1, NUTF2, OAS2, OAS3, OBFC2A, OCLM, ODZ2, OGFRL1, OLFML2B, OLR1, OR10Q1, OR14J1, OR1J2, OR1Q1, OR2A1, OR2A7, OR2A9P, OR2B3, OR4D10, OR4L1, OR51A2, OR52W1, OR5AU1, OR5L2, OR6B1, ORC4, OSMR, OSR2, OXTR, P2RX7, PACSIN2, PAPPA, PARP14, PBK, PCDHB13, PCDHB14, PCDHB16, PCDHB2, PCDHB3, PCDHB4, PCYT2, PDE1C, PDE4DIP, PDE5A, PDGFA, PDGFD, PDPN, PDZRN3, PEG10, PHACTR3, PHF11, PHLDB2, PIM1, PITPNM3, PKD2L1, PKDCC, PLA2G4A, PLEKHA3, PLK1, PLK4, PLSCR1, PLXNA2, PLXNC1, PM20D2, PMAIP1, PPAP2B, PPL, PPP1R12B, PRAMEF2, PRC1, PRDM1, PRDM15, PRG4, PRICKLE1, PRICKLE2, PRKAA2, PRKG2, PRPS1, PRUNE2, PRY, PSIP1, psiTPTE22, PTBP2, PTGS1, PTPRC, PTPRN, PYGO1, RAB12, RAD51AP1, RASA4, RASGRF2, RBMS1, RBMX2, RCVRN, RERGL, REV3L, RGPD1, RGPD2, RGPD6, RGS4, RHBDF1, RHOJ, RIMS1, RIPK2, RNASE2, RNF122, RNU2-1, RPL22L1, RPL8, RPRD1A, RPRM, RPS26P11, RPS6KA6, RPS8, RPSAP52, RRP15, RSPO3, RUNX1T1, S100A8, S1PR1, SCIN, SCN2A, SCUBE3, SEPP1, SERPINB3, SERPINB4, SERPINB9, SERPINE2, SERPINF1, SERPING1, SESTD1, SFRP1, SFRP4, SGK1, SGOL1, SGOL2, SHCBP1, SHMT1, SKA1, SKA3, SKIL, SLC1A3, SLC39A8, SLC40A1, SLC43A3, SLC6A15, SLFN11, SLITRK4, SMAD4, SMC4, SNHG1, SNORD32B, SOCS5, SPC24, SPC25, SPDYE8P, SPON1, SRD5A1P1, SRGAP1, SRGN, SRSF10, SSPN, SSTR1, SSX5, ST6GALNAC5, ST8SIA2, STC1, STEAP1, STEAP2, STEAP4, STOM, SV2A, SVEP1, SYNPR, TACC2, TAGLN, TAS2R10, TBC1D15, TBC1D2, TBX3, TEK, TES, TFAP2A, TFPI, TFPI2, TGFBR3, TGOLN2, THAP2, THBS2, THRB, THSD7A, TINAGL1, TLE3, TLE4, TLN2, TLR1, TLR4, TLR5, TLR6, TLR7, TM4SF18, TMEM119, TMEM135, TMEM155, TMEM30B, TMEM49, TMEM65, TMTC1, TNC, TNFAIP3, TNFRSF10C, TNFRSF11B, TNFSF10, TNFSF13B, TNIK, TOP2A, TOR1AIP1, TOX, TPI1, TPM2, TPM3, TPX2, TRA2B, TRAF3IP2, TRIM24, TRIM36, TRIM43, TRIM64, TROAP, TSIX, TTC22, TTK, UBE2C, UHRF1, UNC5B, USP8, VEGFA, VGLL3, VTI1B, VTRNA1-3, VWA5A, WDR17, WDR52, WEE1, WISP1, WISP2, WNT16, WNT2, WWC1, XAGE3, XPO4, ZC3H11A, ZC3H7B, ZDHHC15, ZFP36, ZFP82, ZMYM2, ZNF135, ZNF207, ZNF28, ZNF280B, ZNF284, ZNF285, ZNF322A, ZNF462, ZNF506, ZNF595, ZNF678, ZNF714, ZNF717, ZNF737, ZNF808, ZNHIT2, and ZWINT.

Described herein are methods comprising, identifying an animal having a C9ORF72 associated disease; and administering a C9ORF72 antisense compound and thereby reducing nuclear retention of any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, ZNF695.

Provided herein are methods, comprising administering a C9ORF72 antisense compound; and monitoring the level of any of ADARB2, NDST1, MITF, DPH2, NUDT6, TCL1B, PGA5, TRIM32, CYP2C9, MPP7, PTER, WBP11, HMGB2, ORAOV1, RANGAP1, ZNF695, SOX6, JARID2, and DAZ2 as a measure of the amount of C9ORF72 nucleic acid containing a hexanucleotide repeat expansion is present in a cell.

Provided herein are methods, comprising identifying an animal having a C9ORF72 associated disease; administering a C9ORF72 antisense compound; and monitoring the level of any of ADARB2, NDST1, MITF, DPH2, NUDT6, TCL1B, PGA5, TRIM32, CYP2C9, MPP7, PTER, WBP11, HMGB2, ORAOV1, RANGAP1, ZNF695, SOX6, JARID2, and DAZ2 as a measure of the amount of C9ORF72 nucleic acid containing a hexanucleotide repeat expansion is present in a cell.

In certain embodiments, the level of any of ADARB2, NDST1, MITF, DPH2, NUDT6, TCL1B, PGA5, TRIM32, CYP2C9, MPP7, PTER, WBP11, HMGB2, ORAOV1, RANGAP1, ZNF695, SOX6, JARID2, and DAZ2 increases after administration of an effective amount of a C9ORF72 antisense compound.

In certain embodiments, the level of any of ADARB2, NDST1, MITF, DPH2, NUDT6, TCL1B, PGA5, TRIM32, CYP2C9, MPP7, PTER, WBP11, HMGB2, ORAOV1, RANGAP1, ZNF695, SOX6, JARID2, and DAZ2 decreases after administration of an effective amount of a C9ORF72 antisense compound.

In certain embodiments, the cell is in vitro.

In certain embodiments, the cell is in an animal.

In certain embodiments, the animal is a human.

In certain embodiments, the antisense compound comprises a single-stranded antisense oligonucleotide complementary to a C9ORF72 nucleic acid.

In certain embodiments, the C9ORF72 nucleic acid is a human C9ORF72 nucleic acid.

In certain embodiments, the C9ORF72 associated disease is a C9ORF72 hexanucleotide repeat expansion associated disease.

In certain embodiments, the C9ORF72 associated disease is amyotrophic lateral sclerosis (ALS) or frontotemporal dementia (FTD).

In certain embodiments, the C9ORF72 hexanucleotide repeat expansion associated disease is amyotrophic lateral sclerosis (ALS) or frontotemporal dementia (FTD).

In certain embodiments, the amyotrophic lateral sclerosis (ALS) is familial ALS or sporadic ALS.

In certain embodiments, the single-stranded antisense oligonucleotide comprises at least one modification.

In certain embodiments, the single-stranded antisense oligonucleotide is specifically hybridizable to a human C9ORF72 nucleic acid.

In certain embodiments, the single-stranded antisense oligonucleotide is at least 75%, at least 80%, at least 85%, at least 90%, or at least 95% complementary to an equal length portion of a human C9ORF72 nucleic acid.

In certain embodiments, the single-stranded antisense oligonucleotide is 100% complementary to an equal length portion of a human C9ORF72 nucleic acid.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the single-stranded oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-(CH2)n-O-2' bridge, wherein n is 1 or 2; and 4'-CH$_2$—O—CH$_2$-2'.

In certain embodiments, the bicyclic sugar comprises a 4'-CH(CH$_3$)—O-2' bridge.

In certain embodiments, the at least one modified nucleoside having a modified sugar comprises a non-bicyclic 2'-modified modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:
 a gap segment consisting of linked deoxynucleosides;
 a 5' wing segment consisting of linked nucleosides;
 a 3' wing segment consisting of linked nucleosides;
 wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:
 a gap segment consisting of ten linked deoxynucleosides;
 a 5' wing segment consisting of five linked nucleosides;
 a 3' wing segment consisting of five linked nucleosides;
 wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15 or 16 linked nucleosides.

In certain embodiments, the single-stranded antisense oligonucleotide consists of 17 linked nucleosides.

In certain embodiments, the single-stranded antisense oligonucleotide consists of 18 linked nucleosides.

In certain embodiments, the single-stranded antisense oligonucleotide consists of 19 linked nucleosides.

In certain embodiments, the single-stranded antisense oligonucleotide consists of 20 linked nucleosides.

In certain embodiments, the single-stranded antisense oligonucleotide consists of 21, 22, 23, 24, or 25 linked nucleosides.

In certain embodiments, the administering is parenteral administration.

In certain embodiments, the parenteral administration is any of injection or infusion.

In certain embodiments, the parenteral administration is any of intrathecal administration or intracerebroventricular administration.

In certain embodiments, at least one symptom of a C9ORF72 associated disease is ameliorated or prevented.

In certain embodiments, at least one symptom of a C9ORF72 hexanucleotide repeat associated disease is ameliorated or prevented.

In certain embodiments, progression of at least one symptom of a C9ORF72 associated disease is slowed.

In certain embodiments, progression of at least one symptom of a C9ORF72 hexanucleotide repeat associated disease is slowed.

In certain embodiments, the at least one symptom is any of muscle weakness, fasciculation and cramping of muscles, difficulty in projecting the voice, shortness of breath, difficulty in breathing and swallowing, inappropriate social behavior, lack of empathy, distractibility, changes in food preferences, agitation, blunted emotions, neglect of personal hygiene, repetitive or compulsive behavior, and decreased energy and motivation.

Described herein are methods comprising administering a C9ORF72 antisense compound to a cell or tissue containing a C9ORF72 hexanucleotide repeat expansion and thereby normalizing expression of any of C3, EDNRB2, and Endothelin.

Described herein are methods comprising administering a C9ORF72 antisense compound to a cell or tissue containing a C9ORF72 hexanucleotide repeat expansion and thereby normalizing expression of any of ABCA6, ACVR2A, ADAMTS5, C11orf87, C3, CCL8, CCNL1, CD44, CELF2, CFB, CHRDL1, CLU, CP, CXCL6, DCN, DKK3, EDN1, EDNRB, EFNA5, ENPP2, F10, F3, FAM3C, FOXP2, FYN, IARS, IGSF10, IL6ST, LPAR1, MLXIPL, NEDD4L, ORC4, PDE1C, PPAP2B, PRPS1, REV3L, RSPO3, SCUBE3, SEPP1, SERPINE2, SESTD1, SPON1, TBC1D15, TGFBR3, TNFSF10, TNFSF13B, and WDR52.

Described herein are methods comprising administering a C9ORF72 antisense compound to a cell or tissue containing a C9ORF72 hexanucleotide repeat expansion and thereby normalizing expression of any of ABCA6, ABCA9, ABCB4, ABCC3, ABCC9, ABO, ACAN, ACOT13, ACSM2A, ACSS3, ACVR2A, ACVR2B, ADAMDEC1, ADAMTS5, ADH1A, ADH1B, ADH1C, ADM, AFF3, AGBL3, AHNAK2, AK4, ALDH1A3, ALDH1L2, ALMS1P, ALOX5AP, AMOT, AMPH, ANKRD32, ANLN, ANO3, ANO4, AOX1, APCDD1, APLNR, APOBEC3B, APOL6, APOLD1, AR, ARHGAP11A, ARHGAP28, ARHGAP29, ARHGEF35, ARL17A, ARL4D, ARMS2, ARNT2, ARRDC3, ARSE, ARVP6125, ATOH8, ATP2A2, AURKA, AURKB, BACH1, BAMBI, BCL3, BDH2, BICC1, BNC2, BRCA2, BRIP1, BRWD3, BTF3L4, BUB1, BUB1B, C11orf87, C12orf48, C12orf64, C13orf18, C14orf149, C15orf42, C1orf191, C1orf198, C1orf63, C1QB, C1R, C1S, C2orf63, C3, C3orf16, C3orf31, C3orf59, C4orf29, C4orf31, C4orf49, C5orf13, C5orf23, C6orf105, C6orf223, C1orf63, C9, CA12, CA13, CACHD1, CADPS, CASC5, CASP10, CBWD1, CCDC144B, CCDC144C, CCDC15, CCIN, CCL28, CCL8, CCNA2, CCNB1, CCNB2, CCNF, CCNL1, CCRL1, CD4, CD68, CDC20, CDC25B, CDC45, CDC6, CDC7, CDCA2, CDCA3, CDCA8, CDH6, CDHR4, CDK1, CDK15, CDK2, CDON, CELF2, CENPA, CENPE, CENPF, CENPI, CENPK, CEP55, CFB, CGB, CGB1, CGB5, CH25H, CHRDL1, CHRNA5, CKAP2L, CKS2, CLDN11, CLEC2A, CLGN, CLIC2, CLIC6, CLSPN, CMKLR1, CNKSR2, CNN1, CNR2, CNTNAP3, COL8A1, COLEC12, COMP, CP, CPA4, CPE, CPLX2, CPM, CPXM1, CRABP2, CRISPLD2, CRY1, CTAGE7P, CTNNBIP1, CTSC, CTSL1, CTSS, CXCL14, CXCL6, CXCR7, CYB5A, CYBB, CYP1B1, CYP24A1, CYP26B1, CYP27A1, CYP3A43, CYP7B1, CYTL1, CYYR1, DBF4, DCDC1, DCN, DDIT3, DDIT4, DEFB109P1B, DENND1B, DEPDC1, DES, DGCR14, DHRS3, DIRC1, DKFZp566F0947, DKFZp667F0711, DKK1, DKK3, DLGAP5, DLX2, DMKN, DNA2, DPP4, DPT, DSEL, DTX3L, DTYMK, E2F8, EDN1, EDNRB, EFEMP1, EFNA5, ELL2, EMCN, EMP1, ENKUR, ENPEP, ENPP2, ENPP5, EPB41L4A, EPSTI1, ERCC6, ERCC6L, EREG, ESM1, ETFDH, F10, F2R, F2RL2, F3, FABP3, FAM101B, FAM110B, FAM156A, FAM20A, FAM3C, FAM43A, FAM46C, FAM59A, FAM71A, FAM75C1, FAM83D, FBLN1, FCER1G, FCGR2A, FDPSL2A, FER, FGD4, FIBIN, FKBP14, FLJ10038, FLJ31356, FLJ39095, FLJ39739, FLJ41170, FLRT3, FMN1, FOLR2, FOLR3, FOSL2, FOXC2, FOXE1, FOXP2, FRRS1, FTLP10, FUT9, FYN, G0S2, GABRE, GABRQ, GEMC1, GFRA1, GLDN, GLIPR2, GLIS3, GOLGA6B, GPNMB, GPR133, GPR31, GPR65, GPRC5B, GRB14, GSTT1, GSTT2, GTPBP8, GTSE1, GUCY1B3, HAS2, HAUS3, HECW2, HELLS, HIST1H1B, HIST1H2AE, HIST1H2AJ, HIST1H2BF, HIST1H2BM, HIST1H3B, HIST1H3J, HIST1H4A, HIST1H4C, HIST1H4D, HIST1H4L, HIST2H2BC, HIST2H3A, HJURP, HMGB2, HMMR, HNRNPK, HOXB2, HOXD10, HOXD11, HSD17B7P2, HTR1B, HUNK, IARS, ICAM1, IDH1, IFI16, IFITM1, IFITM3, IGF1, IGSF10, IL13RA2, IL17RA, IL17RD, IL18R1, IL1R1, IL1RN, IL20RB, IL4R, IL6ST, IQGAP3, IRS1, ITGA6, ITGA8, ITGB3, ITGBL1, JAG1, JAM2, KCNJ2, KCNJ8, KCNK15, KIAA0509, KIAA0802, KIAA1199, KIAA1324L, KIAA1524, KIF11, KIF14, KIF15, KIF16B, KIF18B, KIF20A, KIF20B, KIF23, KIF2C, KIF4A, KIFC1, KIT, KRT19, KRT34, KRTAP1-1, KRTAP1-5, KRTAP2-2, KRTAP2-4, KRTAP4-11, KRTAP4-12, KRTAP4-5, KRTAP4-7, LAMA1, LAMA4, LANCL3, LAP3, LAPTM5, LARP7, LBR, LGI1, LHX5, LHX9, LMCD1, LMNB1, LMO4, LOC100127980, LOC100128001, LOC100128107, LOC100128191, LOC100128402, LOC100129029, LOC100130000, LOC100132167, LOC100132292, LOC100132891, LOC100216479, LOC100287877, LOC100288069, LOC100288560, LOC100505808, LOC100505813, LOC100505820, LOC100506165, LOC100506335, LOC100506456, LOC100507128, LOC100507163, LOC100507425, LOC116437, LOC144438, LOC153910, LOC157503, LOC256374, LOC283868, LOC285944, LOC338667, LOC339822, LOC348120, LOC349408, LOC389332, LOC399884, LOC400684, LOC401022, LOC642006, LOC643551, LOC646743, LOC646804, LOC727820, LOC728264, LOC728640, LOC729420, LOC729978, LOH3CR2A, LOXL4, LPAR1, LRCH2, LRIG3, LRRC37A4, LRRTM1, LYPD6B, MAB21L1, MAFB, MAOA, MAPK13, MARS, MASP1, MASTL, MBD2, MBNL3, MC4R, MCM8, ME2, MEIS3P1, MEST, METTL8, MEX3A, MFAP4, MFGE8, MGC16121, MGC24103, MGP, MIA3, MIER1, MIR125A, MIR138-1, MIR145, MIR199A2, MIRLET7I, MKI67, MLF2, MMD, MME, MMP10, MMP12, MMP27, MOBKL1B, MRAP2, MRPL9, MRPS11, MSC, MST4, MSTN, MTMR7, MTSS1L, MTUS2, MYBL2, MYCT1, MYOCD, MYPN, MZT2A, NACA2, NAIP, NAMPT, NAP1L3, NBEA, NBPF10, NCAPG, NCAPG2, NCAPH, NCRNA00182, NCRNA00205, NCRNA00219, NCRNA00256A, NDC80, NEDD4L, NEK2, NETO2, NEU4, NEUROD6, NFIB, NFIL3, NFKBIZ, NGFR, NKX2-2, NKX2-6, NNMT, NOC2L, NOG, NOTCH3, NOVA1, NOX4, NPTX2, NR2F2, NR4A3, NR5A2, NTN4, NUCKS1, NUF2, NUSAP1, NUTF2, OAS2, OAS3, OBFC2A, OCLM, ODZ2, OGFRL1, OLFML2B, OLR1, OR10Q1, OR14J1, OR1J2, OR1Q1, OR2A1, OR2A7, OR2A9P, OR2B3, OR4D10, OR4L1, OR51A2, OR52W1, OR5AU1, OR5L2, OR6B1, ORC4, OSMR, OSR2, OXTR, P2RX7, PACSIN2, PAPPA, PARP14, PBK, PCDHB13, PCDHB14, PCDHB16, PCDHB2, PCDHB3, PCDHB4, PCYT2, PDE1C, PDE4DIP, PDE5A, PDGFA, PDGFD, PDPN, PDZRN3, PEG10, PHACTR3, PHF11, PHLDB2, PIM1, PITPNM3, PKD2L1, PKDCC, PLA2G4A, PLEKHA3, PLK1, PLK4, PLSCR1, PLXNA2, PLXNC1, PM20D2, PMAIP1, PPAP2B, PPL, PPP1R12B, PRAMEF2, PRC1, PRDM1, PRDM15, PRG4, PRICKLE1, PRICKLE2, PRKAA2, PRKG2, PRPS1, PRUNE2, PRY, PSIP1, psiTPTE22, PTBP2, PTGS1, PTPRC, PTPRN, PYGO1, RAB12, RAD51AP1, RASA4, RASGRF2, RBMS1, RBMX2, RCVRN, RERGL, REV3L, RGPD1, RGPD2, RGPD6, RGS4, RHBDF1, RHOJ, RIMS1, RIPK2, RNASE2, RNF122, RNU2-1, RPL22L1, RPL8, RPRD1A, RPRM, RPS26P11, RPS6KA6, RPS8, RPSAP52, RRP15, RSPO3, RUNX1T1, S100A8, S1PR1, SCIN, SCN2A, SCUBE3, SEPP1, SERPINB3, SERPINB4, SERPINB9, SERPINE2, SERPINF1, SERPING1, SESTD1, SFRP1, SFRP4, SGK1, SGOL1, SGOL2, SHCBP1, SHMT1, SKA1, SKA3, SKIL, SLC1A3, SLC39A8, SLC40A1, SLC43A3, SLC6A15, SLFN11, SLITRK4, SMAD4, SMC4, SNHG1, SNORD32B, SOCS5, SPC24, SPC25, SPDYE8P, SPON1, SRD5A1P1, SRGAP1, SRGN, SRSF10, SSPN, SSTR1, SSX5, ST6GALNAC5, ST8SIA2, STC1, STEAP1, STEAP2, STEAP4, STOM, SV2A, SVEP1, SYNPR, TACC2, TAGLN, TAS2R10, TBC1D15, TBC1D2, TBX3, TEK, TES, TFAP2A, TFPI, TFPI2, TGFBR3, TGOLN2, THAP2, THBS2, THRB, THSD7A, TINAGL1, TLE3, TLE4, TLN2, TLR1, TLR4, TLR5, TLR6, TLR7, TM4SF18, TMEM119, TMEM135, TMEM155, TMEM30B, TMEM49, TMEM65, TMTC1, TNC, TNFAIP3, TNFRSF10C, TNFRSF11B, TNFSF10, TNFSF13B, TNIK, TOP2A, TOR1AIP1, TOX, TPI1, TPM2, TPM3, TPX2, TRA2B, TRAF3IP2, TRIM24, TRIM36, TRIM43, TRIM64, TROAP, TSIX, TTC22, TTK, UBE2C, UHRF1, UNC5B, USP8, VEGFA, VGLL3, VTI1B, VTRNA1-3, VWA5A, WDR17, WDR52, WEE1, WISP1, WISP2, WNT16, WNT2, WWC1, XAGE3, XPO4, ZC3H11A, ZC3H7B, ZDHHC15, ZFP36, ZFP82, ZMYM2, ZNF135, ZNF207, ZNF28, ZNF280B, ZNF284, ZNF285, ZNF322A, ZNF462, ZNF506, ZNF595, ZNF678, ZNF714, ZNF717, ZNF737, ZNF808, ZNHIT2, and ZWINT.

Described herein are methods comprising administering a C9ORF72 antisense compound to a cell or tissue containing a C9ORF72 hexanucleotide repeat expansion and thereby reducing nuclear retention of any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, and ZNF695.

In certain embodiments, the cell or tissue is human fibroblast cells.

In certain embodiments, the cell or tissue is human cortex.

In certain embodiments, the antisense compound comprises a single-stranded antisense oligonucleotide complementary to a C9ORF72 nucleic acid.

In certain embodiments, the C9ORF72 nucleic acid is a human C9ORF72 nucleic acid.

In certain embodiments, the single-stranded antisense oligonucleotide comprises at least one modification.

In certain embodiments, the single-stranded antisense oligonucleotide is specifically hybridizable to a human C9ORF72 nucleic acid.

In certain embodiments, the single-stranded antisense oligonucleotide is at least 75%, at least 80%, at least 85%, at least 90%, or at least 95% complementary to an equal length portion of a human C9ORF72 nucleic acid.

In certain embodiments, the single-stranded antisense oligonucleotide is 100% complementary to an equal length portion of a human C9ORF72 nucleic acid.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the antisense oligonucleotides comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-(CH2)n-O-2' bridge, wherein n is 1 or 2; and 4'-CH$_2$—O—CH$_2$-2'.

In certain embodiments, the bicyclic sugar comprises a 4'-CH(CH$_3$)—O-2' bridge.

In certain embodiments, the at least one modified nucleoside having a modified sugar comprises a non-bicyclic 2'-modified modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises: a gap segment consisting of linked deoxynucleosides;
a 5' wing segment consisting of linked nucleosides;
a 3' wing segment consisting of linked nucleosides;
wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15 linked nucleosides.

In certain embodiments, the single-stranded antisense oligonucleotide consists of 16 linked nucleosides.

In certain embodiments, the single-stranded antisense oligonucleotide consists of 17 linked nucleosides.

In certain embodiments, the single-stranded antisense oligonucleotide consists of 18 linked nucleosides.

In certain embodiments, the single-stranded antisense oligonucleotide consists of 19 linked nucleosides.

In certain embodiments, the single-stranded antisense oligonucleotide consists of 20 linked nucleosides.

In certain embodiments, wherein the single-stranded antisense oligonucleotide consists of 12 to 30 linked nucleosides and comprises a nucleobase sequence comprising at least 8, at least 9, at least 10, at least 11, at least 12, at least 13, at least 14, at least 15, at least 16, at least 17, at least 18, at least 19, or at least 20 contiguous nucleobases of SEQ ID NO: 20-24 or 28-30.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2 and 4'-$CH_2$—O—$CH_2$-2'). Preferably, each distinct region comprises uniform sugar moieties. The wing-gap-wing motif is frequently described as "X—Y-Z", where "X" represents the length of the 5' wing region, "Y" represents the length of the gap region, and "Z" represents the length of the 3' wing region. As used herein, a gapmer described as "X—Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-10-4 gapmer motif.

In certain embodiments, antisense compounds targeted to a C9ORF72 nucleic acid possess a 4-10-4 gapmer motif.

In certain embodiments, antisense compounds targeted to a C9ORF72 nucleic acid possess a 4-10-3 gapmer motif.

In certain embodiments, antisense compounds targeted to a C9ORF72 nucleic acid possess a 5-9-5 gapmer motif.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-$(CH_2)_n$-O-2' bridge, wherein n is 1 or 2; and 4'-$CH_2$—O—$CH_2$-2'. In certain embodiments, the bicyclic sugar is comprises a 4'-CH(CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a C9ORF72 nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleoside is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group. In certain embodiments, uniformly modified antisense compound may target C9ORF72, or any portion thereof, such as a hexanucleotide repeat expansion. In certain embodiments, targeting the hexanucleotide repeat expansion with a uniformly modified antisense compound reduced the repeat RNA by blocking the interaction with RNA binding proteins. In certain embodiments, this results in the toxic RNA being absent from foci and being degraded instead.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain emodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or 5), 4'-S, 2'-F, 2'-$OCH_3$, 2'-$OCH_2CH_3$, 2'—$OCH_2CH_2F$ and 2'-$O(CH_2)_2O$ $CH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—N($R_m$)($R_n$), O—$CH_2$—C(=O)—N($R_m$)($R_n$), and O—$CH_2$—C(=O)—N($R_1$)—$(CH_2)_2$—N($R_m$)($R_n$), where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2; 4'—$(CH_2)_2$—O-2' (ENA); 4'-CH($CH_3$)—O-2' and 4'-CH ($CH_2OCH_3$)—O- 2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N (OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2',4'-(CH$_2$)$_2$-2', 4'-(CH$_2$)$_3$-2',4'-CH$_2$—O-2',4'-(CH$_2$)$_2$—O-2',4'-CH$_2$—O—N(R)-2' and 4'-CH$_2$—N(R)—O-2'—wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

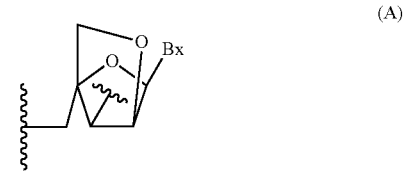

(A)

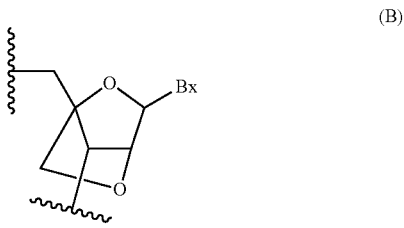

(B)

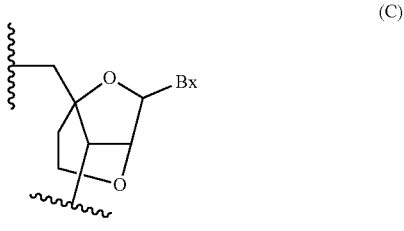

(C)

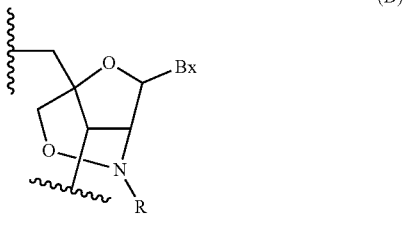

(D)

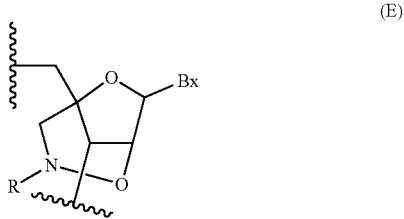

(E)

33

-continued

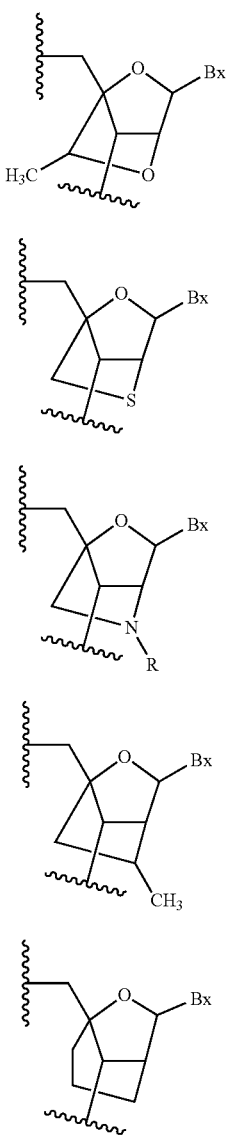

(F)

(G)

(H)

(I)

(J)

wherein Bx is the base moiety and R is independently H, a protecting group or $C_1$-$C_{12}$ alkyl.

In certain embodiments, bicyclic nucleosides are provided having Formula I:

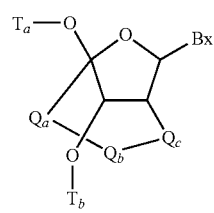

I wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

34

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

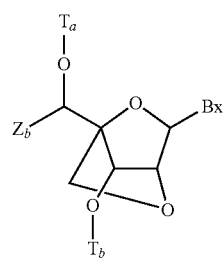

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

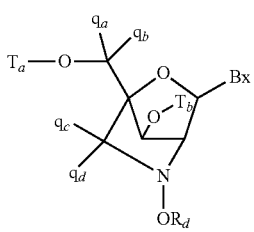

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

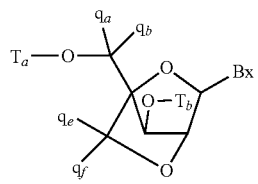

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

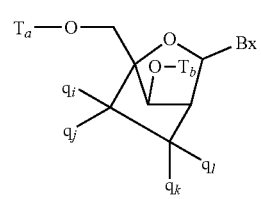

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$, or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)$—

$NH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chian. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

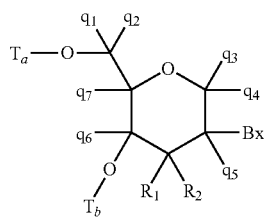

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_mR_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy a basic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of certain variants of C9ORF72. In certain embodiments, the antisense oligonucleotides described herein preferentially inhibit expression of variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell. In certain embodiments, the hexanucleotide repeat expansion causes various expression of various genes to be misregulated. In certain embodiments, antisense oligonucleotides described herein are useful for normalizing expression of various misregulated genes. In certain embodiments, the hexanucleotide repeat expansion causes nuclear retention of various proteins. In certain embodiments, the antisense oligonucleotides described herein are useful for reducing nuclear retention of various proteins.

Based on earlier studies directed to repeat expansions, it is not possible to predict if antisense oligonucleotides targeting C9ORF72 outside of the hexanucleotide repeat expansion would successfully inhibit expression of C9ORF72 for two reasons. First, the C9ORF72 repeat expansion is located in an intron and it is not known if the RNA in the foci contains only the repeats or also the flanking intronic sequence. For example, an earlier study on myotonic dystrophy type 2 (DM2), which is a disease caused by a CCTG expansion mutation in intron 1 of the ZNF9 gene, determined that large DM2 expansions did not prevent allele-specific pre-mRNA splicing, nuclear export of the transcripts, or steady-state mRNA or protein levels. The study further demonstrated that the ribonuclear inclusions found associated with the disease are enriched for the CCUG expansion, but not the flanking intronic sequences. These data suggest that the downstream molecular effects of the DM2 mutation may be triggered by the accumulation of CCUG repeat tract alone. Therefore, this study implies that targeting the CCUG repeat expansion alone would lead to amelioration of the disease, since targeting the flanking sequences, especially the region downstream of the repeat expansion, would not affect the formation of ribonuclear inclusions (Margolis et al. Hum. Mol. Genet., 2006, 15:1808-1815). Second, it is not known how fast intron 1 of C9ORF72, which contains the repeats, is excised and accumulates in foci. Thus, it is not possible to predict if targeting the pre-mRNA would result in elimination of the repeat RNA and foci.

C9OFF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
| --- | --- | --- | --- | --- |
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
| --- | --- | --- | --- | --- |
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
| --- | --- | --- | --- | --- |
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
| --- | --- | --- | --- | --- |
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
| --- | --- | --- | --- | --- |
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Effect of Antisense Inhibition of Human C9ORF72 in Human Primary Fibroblasts Antisense oligonucleotides were designed targeting various regions of the C9ORF72 gene (the complement of GENBANK Accession No. NT_008413.18 truncated from nucleotides 27535000 to 27565000, designated herein as SEQ ID NO: 2). The target start site, target region, and description of each antisense oligonucleotide are specified in Table 6 below. The italicized and underlined nucleosides denote 2'-O-methyl RNA bases; the bolded nucleosides indicate a DNA phosphorothioate backbone. As observed from the Table, several of the antisense oligonucleotides target intron 1 and, therefore, target the pre-mRNA sequence of C9ORF72. Intron 1 of C9ORF72 contains the hexanucleotide repeat.

Additional antisense oligonucleotides were designed targeting various regions of the C9ORF72 gene. The antisense oligonucleotides in Table 7 were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages throughout each gapmer are phosphorothioate linkages. All cytosine residues throughout each gapmer are 5-methylcytosines. Each antisense oligonucleotide listed in Table 7 is targeted to the SEQ ID NO: 2.

each variant (V1 and V2), as well as the expression levels of the pre-mRNA levels of each variant is presented in Table 8. The individual RNA levels were measured with the NanoString nCounter™ gene expression system (NanoString® Technologies).

TABLE 8

% expression of C9ORF72 mRNA variants 1 and 2 after ASO treatment

| ID # | % V1 mRNA | % V2 mRNA | % V1 pre-mRNA | % V2 pre-mRNA |
|---|---|---|---|---|
| 1 | −30 | −25 | −20 | −30 |
| 2 | 66 | 174 | −47 | −10 |
| 3 | 124 | 142 | −35 | −42 |
| 4 | 35 | −46 | −28 | −25 |
| 5 | −49 | −23 | −6 | −15 |
| 577816 | −68 | −83 | −17 | −15 |
| 577083 | −55 | −20 | −15 | −10 |
| 577061 | 30 | −11 | 60 | −12 |

TABLE 6

Antisense oligonucleotides targeting SEQ ID NO: 2

| Sequence | ID # | Target Start Site | Target Stop Site | Target Region | SEQ ID NO |
|---|---|---|---|---|---|
| CCCAUTCCAGTTTCCAUCA | 1 | 8179 | 8197 | Exon 2 | 20 |
| GCGGCUTGTTTCCCTCCUUGU | 2 | 1398 | 1417 | Intron 1 V1 RNA | 21 |
| GCCCCGGCCCCTAGCGCGCG | 3 | 1448 | 1467 | Intron 1 & Repeat | 22 |
| CCCGACCACGCCCCGGCCCC | 4 | 1469 | 1488 | Intron 1 & Repeat | 23 |
| AGCCACCTTCTCCAACCUG | 5 | 3250 | 3268 | Intron 1 | 24 |

TABLE 7

Antisense oligonucleotides targeting SEQ ID NO: 2

| Sequence | ISIS No | Target Start Site | Target Stop Site | Target Region | SEQ ID NO |
|---|---|---|---|---|---|
| GCCTTACTCTAGGACCAAGA | 577816 | 7990 | 8009 | Exon 2 | 28 |
| GGTAACTTCAAACTCTTGGG | 577083 | 3452 | 3471 | Intron 1 | 29 |
| TACAGGCTGCGGTTGTTTCC | 577061 | 1406 | 1425 | Intron 1 | 30 |

The antisense oligonucleotides were tested in human primary fibroblasts. Human primary fibroblasts were plated at 20,000 cells/well and transfected using Cytofectin reagent with 100 nM of antisense oligonucleotide. After an incubation period of 3 days, C9ORF72 total mRNA levels were measured by RT-qPCR (FIG. 1b). The figure presents the total mRNA levels of C9ORF72. GAPDH mRNA levels are also presented to show equal RNA loading of the gel. The data indicates that treatment with ASOs 1, 4, and 5 produce the strongest knockdown of C9ORF72 total mRNA. Table 8 also presents the results of treatment of the cells with ISIS 577816, ISIS 577083, and ISIS 577061.

FIG. 1a also presents the targeting regions of ASOs 1-5 with respect to the C9ORF72 mRNA variant 1, GENBANK Accession No. NM_145005.4 (designated herein as SEQ ID NO: 6) and mRNA variant 2, GENBANK Accession No. NM_018325.2 (designated herein as SEQ ID NO: 4). The percent expression levels of the total mature mRNA levels of Example 2: Effect of Antisense Inhibition of Human C9ORF72 on Aberrant Gene Expression in ALS/FTD Patient Fibroblast To examine the effects of C9ORF72 mutation on gene expression and potential splicing events, several ALS/FTD-derived fibroblast cell lines were propagated and gene array analyses were performed.

Gene array analyses were performed using Human Exon 1.0 ST array (Affymetrix). Induced pluripotent cell lines (iPSC) line 34, iPSC #850 (expansion copy number 916); line 50 iPSC #816 (copy number 1,150); and line 75, iPSC #1280 (copy number 950) were used.

C9orf75 line 50 was compared with cell line 75. Patient-derived cell lines showed a very similar gene expression profile ($R^2$=0.991), even though the patients, from whom the fibroblasts were derived, were not related to each other. Hence, the data suggests that different patient-derived fibroblasts exhibit a similar transcriptome, supporting a C9ORF72-specific ASO therapeutic intervention approach.

The gene expression profile of the C9ORF72 fibroblasts was compared with fibroblasts obtained from ALS patients carrying a different familial gene mutation for SOD1 (SOD1$^{D90A}$). There was very little overlap of altered genes in the C9ORF72 fibroblasts when compared to the ALS mutant SOD1 fibroblasts. The gene expression profile of the C9ORF72 fibroblasts was compared with healthy control fibroblasts.

To confirm that the data from C9ORF72 fibroblasts simulated events in vivo, postmortem brain tissue was obtained from C9ORF72 ALS patients and analyzed. The dysregulated genes discovered in the human fibroblast analyses were similarly altered in the cerebellar tissue of ALS C9ORF72 patients. The expression of one of the genes, ENPP2, which was observed to be upregulated in C9ORF72 fibroblasts, was similarly upregulated in human cerebellar tissue. The expression of another gene, RSPO3, which was not significantly altered in the C9ORF72 fibroblasts, was not altered in human cerebellar tissue either. The results are presented in FIG. 2b. Table 9 provides a comprehensive listing of all aberrantly expressed genes that are either upregulated or downregulated in C9ORF72 fibroblasts as well as the motor cortex from ALS patient brain tissue, compared to healthy controls. The data suggests that the C9ORF72 cell lines may be a suitable surrogate to define human CNS relevant biomarkers and to monitor response to ASO therapy.

TABLE 9

Dysregulated Genes

| Fibroblasts | Human Motor Cortex |
| --- | --- |
| ABCA6 | ABO |
| ABCB4 | ACOT13 |
| ABCC3 | ACSM2A |
| ABCC9 | ACSM2A |
| ACAN | ACVR2B |
| ACSS3 | AGBL3 |
| ADAMTS5 | ALMS1P |
| ADAMTS5 | ALOX5AP |
| ADM | ANKRD32 |
| AHNAK2 | APOLD1 |
| AK4 | ARL17A |
| ALDH1A3 | ARL4D |
| AMOT | ARMS2 |
| AMPH | ARSE |
| ANLN | ARVP6125 |
| ANO3 | ATOH8 |
| ANO4 | BACH1 |
| APCDD1 | BDH2 |
| APLNR | BRWD3 |
| APOBEC3B | BTF3L4 |
| APOL6 | C12orf64 |
| AR | C1QB |
| AR | C1orf191 |
| ARHGAP11A | C2orf63 |
| ARHGAP11A | C3orf16 |
| ARHGAP28 | C3orf59 |
| ARHGAP29 | C4orf29 |
| ARHGAP29 | C6orf105 |
| ARHGEF35 | C6orf223 |
| ARL17A | C9 |
| ARNT2 | CASP10 |
| ARRDC3 | CBWD1 |
| ATP2A2 | CD68 |
| AURKA | CDHR4 |
| AURKB | CH25H |
| BAMBI | CNR2 |
| BCL3 | CNTNAP3 |
| BICC1 | CNTNAP3 |
| BNC2 | CPLX2 |
| BNC2 | CRY1 |

TABLE 9-continued

Dysregulated Genes

| Fibroblasts | Human Motor Cortex |
| --- | --- |
| BNC2 | CTAGE7P |
| BRCA2 | CTNNBIP1 |
| BRIP1 | CTSC |
| BUB1 | CTSS |
| BUB1B | CYB5A |
| C11orf87 | CYBB |
| C12orf48 | CYP26B1 |
| C13orf18 | CYP3A43 |
| C14orf149 | DCDC1 |
| C15orf42 | DEFB109P1B |
| C1orf198 | DENND1B |
| C1orf63 | DGCR14 |
| C1R | DKFZp566F0947 |
| C1S | DKFZp667F0711 |
| C3 | DNA2 |
| C3orf31 | EDN1 |
| C4orf31 | ELL2 |
| C4orf49 | EMP1 |
| C5orf13 | ENPEP |
| C5orf23 | ENPEP |
| CA13 | ETFDH |
| CACHD1 | FAM156A |
| CADPS | FAM59A |
| CASC5 | FAM71A |
| CCDC144B | FAM75C1 |
| CCDC144C | FCER1G |
| CCDC15 | FCGR2A |
| CCIN | FDPSL2A |
| CCL28 | FER |
| CCNA2 | FIBIN |
| CCNB1 | FKBP14 |
| CCNB2 | FLJ31356 |
| CCNF | FLJ39095 |
| CCRL1 | FLJ39739 |
| CD4 | FLJ41170 |
| CDC20 | FOLR2 |
| CDC25B | FTLP10 |
| CDC45 | FUT9 |
| CDC6 | GOLGA6B |
| CDC7 | GPNMB |
| CDCA2 | GPR65 |
| CDCA3 | GSTT1 |
| CDCA8 | GSTT1 |
| CDH6 | GTPBP8 |
| CDK1 | HAUS3 |
| CDK15 | HIST1H4L |
| CDK2 | HNRNPK |
| CDON | HSD17B7P2 |
| CENPA | HTR1B |
| CENPE | IDH1 |
| CENPF | IFI16 |
| CENPI | IFITM3 |
| CENPK | IL17RA |
| CEP55 | IL18R1 |
| CGB | IL4R |
| CGB1 | KIAA0509 |
| CGB5 | KIAA0802 |
| CHRNA5 | LAMA1 |
| CKAP2L | LANCL3 |
| CKS2 | LANCL3 |
| CLDN11 | LAP3 |
| CLDN11 | LAPTM5 |
| CLEC2A | LARP7 |
| CLGN | LGI1 |
| CLIC2 | LHX5 |
| CLIC6 | LOC100128001 |
| CLSPN | LOC100128107 |
| CMKLR1 | LOC100128402 |
| CNKSR2 | LOC100129029 |
| CNN1 | LOC100130000 |
| COL8A1 | LOC100132167 |
| COLEC12 | LOC100132292 |
| COMP | LOC100216479 |
| CPA4 | LOC100287877 |
| CPE | LOC100288069 |
| CPM | LOC100288560 |

TABLE 9-continued

| Dysregulated Genes | |
|---|---|
| Fibroblasts | Human Motor Cortex |
| CPXM1 | LOC100505808 |
| CRABP2 | LOC100505813 |
| CRISPLD2 | LOC100505820 |
| CTSL1 | LOC100506165 |
| CXCL14 | LOC100506335 |
| CXCR7 | LOC100506456 |
| CYP1B1 | LOC100507128 |
| CYP24A1 | LOC100507163 |
| CYP27A1 | LOC100507425 |
| CYP7B1 | LOC116437 |
| CYTL1 | LOC144438 |
| CYYR1 | LOC153910 |
| DBF4 | LOC157503 |
| DDIT3 | LOC256374 |
| DDIT4 | LOC283868 |
| DEPDC1 | LOC285944 |
| DES | LOC339822 |
| DHRS3 | LOC348120 |
| DIRC1 | LOC349408 |
| DKK1 | LOC389332 |
| DLGAP5 | LOC399884 |
| DLX2 | LOC646743 |
| DMKN | LOC646804 |
| DPP4 | LOC729978 |
| DPT | LRRTM1 |
| DSEL | ME2 |
| DTX3L | METTLE |
| DTYMK | MIA3 |
| DTYMK | MIER1 |
| E2F8 | MIR125A |
| EDN1 | MIR138-1 |
| EDNRB | MIRLET7I |
| EFEMP1 | MLF2 |
| EMCN | MOBKL1B |
| ENPP2 | MRPL9 |
| ENPP5 | MRPS11 |
| EPB41L4A | MTMR7 |
| EPSTI1 | NACA2 |
| ERCC6 | NAIP |
| ERCC6 | NCRNA00182 |
| ERCC6L | NCRNA00205 |
| EREG | NEU4 |
| ESM1 | NEUROD6 |
| F2R | NFIL3 |
| F2RL2 | NOC2L |
| F3 | NPTX2 |
| FABP3 | NR2F2 |
| FAM101B | NUCKS1 |
| FAM20A | NUTF2 |
| FAM43A | OCLM |
| FAM46C | OR10Q1 |
| FAM83D | OR14J1 |
| FBLN1 | OR2B3 |
| FGD4 | OR4D10 |
| FIBIN | OR4L1 |
| FLJ10038 | OR51A2 |
| FLRT3 | OR52W1 |
| FMN1 | OR5AU1 |
| FOLR3 | OR5L2 |
| FOSL2 | OR6B1 |
| FOXC2 | PACSIN2 |
| FOXE1 | PARP14 |
| FOXP2 | PCDHB4 |
| FRRS1 | PCYT2 |
| GABRE | PHF11 |
| GABRQ | PHLDB2 |
| GEMC1 | PKD2L1 |
|  | PLEKHA3 |
| GFRA1 | PMAIP1 |
| GLDN | PPP1R12B |
| GLIPR2 | PRAMEF2 |
| GLIS3 | PRY |
| GPR133 | PTPRC |
| GPR31 | PYGO1 |
| GPR65 | RASGRF2 |
| GPRC5B | RBMX2 |

TABLE 9-continued

| Dysregulated Genes | |
|---|---|
| Fibroblasts | Human Motor Cortex |
| GRB14 | RCVRN |
| GSTT2 | RERGL |
| GTSE1 | RGPD6 |
| GUCY1B3 | RHBDF1 |
| HAS2 | RNASE2 |
| HECW2 | RNU2-1 |
| HELLS | RPL8 |
| HIST1H1B | RPRD1A |
| HIST1H2AE | RPRM |
| HIST1H2AJ | RPS6KA6 |
| HIST1H2BF | RPS8 |
| HIST1H2BM | RRP15 |
| HIST1H3B | RRP15 |
| HIST1H3J | S100A8 |
| HIST1H4A | SCIN |
| HIST1H4C | SKIL |
| HIST1H4D | SLITRK4 |
| HIST2H2BC | SMAD4 |
| HIST2H2BC | SMAD4 |
| HIST2H3A | SNORD32B |
| HJURP | SOCS5 |
| HMGB2 | SPDYE8P |
| HMMR | SRGN |
| HOXD10 | SRSF10 |
| HOXD11 | SSX5 |
| HUNK | SYNPR |
| ICAM1 | TACC2 |
| IFI16 | TAS2R10 |
| IFITM1 | TEK |
| IGF1 | TES |
| IGSF10 | TGOLN2 |
| IL13RA2 | THAP2 |
| IL17RA | THSD7A |
| IL17RD | TLR1 |
| IL1R1 | TLR5 |
| IL1RN | TLR6 |
| IL20RB | TLR7 |
| IQGAP3 | TM4SF18 |
| IRS1 | TMEM135 |
| ITGA6 | TMEM49 |
| ITGA8 | TNFSF13B |
| ITGB3 | TOR1AIP1 |
| ITGBL1 | TPI1 |
| JAG1 | TPM3 |
| JAM2 | TRIM24 |
| KCNJ2 | TRIM36 |
| KCNJ8 | TRIM43 |
| KCNK15 | TRIM64 |
| KIAA1199 | TSIX |
| KIAA1324L | TSIX |
| KIAA1524 | TSIX |
| KIF11 | TTC22 |
| KIF14 | VTI1B |
| KIF15 | XAGE3 |
| KIF16B | XPO4 |
| KIF18B | ZC3H11A |
| KIF20A | ZC3H7B |
| KIF20B | ZFP82 |
| KIF23 | ZMYM2 |
| KIF2C | ZNF135 |
| KIF4A | ZNF207 |
| KIFC1 | ZNF28 |
| KIT | ZNF284 |
| KRT19 | ZNF285 |
| KRT34 | ZNF322A |
| KRTAP1-1 | ZNF506 |
| KRTAP1-5 | ZNF595 |
| KRTAP2-2 | ZNF678 |
| KRTAP2-4 | ZNF717 |
| KRTAP4-11 | ZNF737 |
| KRTAP4-11 | ZNF808 |
| KRTAP4-12 | ZNHIT2 |
| KRTAP4-5 | |
| KRTAP4-7 | |
| LAMA4 | |
| LBR | |

TABLE 9-continued

Dysregulated Genes

| Fibroblasts | Human Motor Cortex |
|---|---|
| LHX9 | |
| LMCD1 | |
| LMNB1 | |
| LMO4 | |
| LOC100127980 | |
| LOC100128191 | |
| LOC338667 | |
| LOC400684 | |
| LOC401022 | |
| LOC643551 | |
| LOC727820 | |
| LOC727820 | |
| LOC727820 | |
| LOC728264 | |
| LOC728640 | |
| LOC729420 | |
| LOH3CR2A | |
| LOXL4 | |
| LRCH2 | |
| LRIG3 | |
| LRRC37A4 | |
| LYPD6B | |
| MAB21L1 | |
| MAFB | |
| MAOA | |
| MAOA | |
| MAPK13 | |
| MASP1 | |
| MASTL | |
| MBD2 | |
| MBNL3 | |
| MC4R | |
| MCM8 | |
| MEIS3P1 | |
| MEST | |
| MEX3A | |
| MFAP4 | |
| MFGE8 | |
| MGC16121 | |
| MGC24103 | |
| MGP | |
| MIR145 | |
| MIR199A2 | |
| MIRLET7I | |
| MKI67 | |
| MMD | |
| MME | |
| MMP10 | |
| MMP12 | |
| MMP27 | |
| MRAP2 | |
| MSC | |
| MST4 | |
| MSTN | |
| MTSS1L | |
| MTUS2 | |
| MYBL2 | |
| MYCT1 | |
| MYOCD | |
| MYPN | |
| MZT2A | |
| NAP1L3 | |
| NBEA | |
| NBPF10 | |
| NCAPG | |
| NCAPG2 | |
| NCAPH | |
| NCRNA00219 | |
| NCRNA00256A | |
| NDC80 | |
| NEK2 | |
| NETO2 | |
| NFIB | |
| NFKBIZ | |
| NGFR | |
| NKX2-2 | |
| NKX2-6 | |
| NNMT | |
| NOG | |
| NOTCH3 | |
| NOVA1 | |
| NOX4 | |
| NOX4 | |
| NR4A3 | |
| NR5A2 | |
| NTN4 | |
| NUF2 | |
| NUSAP1 | |
| OAS2 | |
| OAS3 | |
| OBFC2A | |
| ODZ2 | |
| OGFRL1 | |
| OLFML2B | |
| OLR1 | |
| OR1J2 | |
| OR1Q1 | |
| OR2A1 | |
| OR2A7 | |
| OR2A9P | |
| OSMR | |
| OXTR | |
| P2RX7 | |
| PAPPA | |
| PBK | |
| PCDHB13 | |
| PCDHB14 | |
| PCDHB16 | |
| PCDHB2 | |
| PCDHB3 | |
| PDE1C | |
| PDE4DIP | |
| PDE5A | |
| PDGFA | |
| PDGFA | |
| PDGFD | |
| PDPN | |
| PEG10 | |
| PHACTR3 | |
| PIM1 | |
| PKDCC | |
| PLK1 | |
| PLK4 | |
| PLSCR1 | |
| PLXNA2 | |
| PLXNC1 | |
| PM20D2 | |
| PRC1 | |
| PRDM1 | |
| PRDM15 | |
| PRG4 | |
| PRICKLE1 | |
| PRICKLE2 | |
| PRKAA2 | |
| PRKG2 | |
| PRUNE2 | |
| PSIP1 | |
| psiTPTE22 | |
| PTBP2 | |
| PTGS1 | |
| PTPRN | |
| RAB12 | |
| RAD51AP1 | |
| RASA4 | |
| RASA4 | |
| RASA4 | |
| RBMS1 | |
| REV3L | |
| RGS4 | |
| RHOJ | |
| RIMS1 | |
| RIPK2 | |

TABLE 9-continued

Dysregulated Genes

| Fibroblasts | Human Motor Cortex |
|---|---|
| RNF122 | |
| RPL22L1 | |
| RPSAP52 | |
| RSPO3 | |
| RUNX1T1 | |
| RUNX1T1 | |
| RUNX1T1 | |
| S1PR1 | |
| SCN2A | |
| SCUBE3 | |
| SEPP1 | |
| SERPINB3 | |
| SERPINB4 | |
| SERPINB9 | |
| SERPINE2 | |
| SERPINF1 | |
| SERPING1 | |
| SFRP1 | |
| SFRP4 | |
| SGK1 | |
| SGOL1 | |
| SGOL2 | |
| SHCBP1 | |
| SHMT1 | |
| SKA1 | |
| SKA3 | |
| SLC1A3 | |
| SLC39A8 | |
| SLC40A1 | |
| SLC43A3 | |
| SLC6A15 | |
| SLFN11 | |
| SMC4 | |
| SNHG1 | |
| SPC24 | |
| SPC25 | |
| SPON1 | |
| SRGAP1 | |
| ST6GALNAC5 | |
| ST8SIA2 | |
| STC1 | |
| STEAP1 | |
| STEAP2 | |
| STEAP4 | |
| STOM | |
| SV2A | |
| SVEP1 | |
| TBC1D2 | |
| TBX3 | |
| TFAP2A | |
| TFPI | |
| TFPI2 | |
| THBS2 | |
| THRB | |
| TINAGL1 | |
| TLE3 | |
| TLE4 | |
| TLN2 | |
| TLR4 | |
| TMEM119 | |
| TMEM155 | |
| TMEM30B | |
| TMEM49 | |
| TMEM65 | |
| TNC | |
| TNFAIP3 | |
| TNFRSF10C | |
| TNFRSF11B | |
| TNIK | |
| TOP2A | |
| TOX | |
| TPX2 | |
| TPX2 | |
| TRA2B | |
| TRAF3IP2 | |
| TROAP | |

TABLE 9-continued

Dysregulated Genes

| Fibroblasts | Human Motor Cortex |
|---|---|
| TTK | |
| UBE2C | |
| UHRF1 | |
| UNC5B | |
| USP8 | |
| VEGFA | |
| VGLL3 | |
| VTRNA1-3 | |
| VWA5A | |
| WDR17 | |
| WEE1 | |
| WISP1 | |
| WISP2 | |
| WNT16 | |
| WNT2 | |
| WWC1 | |
| ZDHHC15 | |
| ZDHHC15 | |
| ZFP36 | |
| ZNF280B | |
| ZNF462 | |
| ZNF714 | |
| ZWINT | |
| | ADH1A |
| | ADH1B |
| | CFB |
| | ADH1C |
| | NEDD4L |
| | TNFSF10 |
| | IL1R1 |
| | PLSCR1 |
| | NAMPT |
| | NFIB |
| | LOC727820 |
| | PDE4DIP |
| | TGFBR3 |
| | FAM3C |
| | PDE4DIP |
| | G0S2 |
| | CHRDL1 |
| | RGPD2 |
| | SESTD1 |
| | PLA2G4A |
| | FOXP2 |
| | LOC727820 |
| | FYN |
| | DCN |
| | CCL8 |
| | ABCA9 |
| | CA12 |
| | PPAP2B |
| | EFNA5 |
| | AOX1 |
| | WDR52 |
| | RGPD1 |
| | IL6ST |
| | IGSF10 |
| | TNFSF13B |
| | SERPINE2 |
| | CP |
| | ADAMDEC1 |
| | CXCL6 |
| | NFIL3 |
| | FAM110B |
| | ACVR2A |
| | REV3L |
| | PPL |
| | CELF2 |
| | LPAR1 |
| | TBC1D15 |
| | LOC727820 |
| | ORC4 |
| | ABCA6 |
| | CCNL1 |
| | OSR2 |
| | PDZRN3 |

TABLE 9-continued

| Dysregulated Genes | |
|---|---|
| Fibroblasts | Human Motor Cortex |
| LOC100132891 | |
| OSMR | |
| ENKUR | |
| TMTC1 | |
| C7orf63 | |
| RSPO3 | |
| PDE1C | |
| LOC642006 | |
| IARS | |
| AFF3 | |
| TAGLN | |
| SSTR1 | |
| TPM2 | |
| SSPN | |
| ALDH1L2 | |
| MARS | |
| PRPS1 | |
| PITPNM3 | |
| RPS26P11 | |
| OXTR | |
| HOXB2 | |
| SRD5A1P1 | |
| C11orf87 | |
| KRTAP1-5 | |
| F10 | |
| DKK3 | |

Of these genes, the most highly differentially expressed genes known to be expressed in the CNS were selected and are summarized in Table 10. These genes express secreted proteins and may therefore be considered as biomarker candidate genes for ALS/FTD. Treatment of fibroblasts with a mixture of ASOs 1-5 and the ISIS oligonucleotides at a final concentration of 100 nM resulted in normalization of the gene expression of a large number of these genes. For instance, treatment of C9ORF72 fibroblasts with ASO reduced the expression of ENPP2 expression from a ~50% increase (p<0.05 vs. control fibroblasts) in C9ORF72 fibroblasts compared to healthy fibroblasts to a 50% decrease (p<0.05 vs. C9ORF72 fibroblasts) after ASO treatment (FIG. 2a).

TABLE 10

List of genes upregulated or downregulated in C9ORF72 fibroblasts compared to control fibroblasts and effect of ASO treatment

| Accession # | Gene Symbol | Aberrant Fibroblast Expression | Aberrant Human Motor Cortex Expression (±25% Change vs. Control) | Aberrant Human Cerebellum Expression (±25% Change vs. Control) | Rescued with ASO Treatment (±25% Change vs. Control ASO) | Secreted |
|---|---|---|---|---|---|---|
| NM_080284 | ABCA6 | No | ND | ND | ND | No |
| NM_001616 | ACVR2A | Yes | ND | ND | ND | No |
| NM_207645 | C11orf87 | No | ND | ND | ND | NA |
| NM_003739.5 | C3 | No | Yes | Yes | Yes | Yes |
| NM_005623 | CCL8 | No | No | Yes | Yes | Yes |
| NM_020307 | CCNL1 | Yes | Yes | Yes | ND | No |
| NM_000610.3 | CD44 | Yes | No | No | Yes | No |
| NM_001025077 | CELF2 | No | No | No | Yes | No |
| NM_001710 | CFB | No | No | No | Yes | Yes |
| NM_145234 | CHRDL1 | Yes | No | No | Yes | Yes |
| NM_001831.3 | CLU | Yes | Yes | Yes | Yes | Yes |
| NM_000096 | CP | Yes | Yes | Yes | Yes | Yes |
| NM_002993 | CXCL6 | Yes | No | No | Yes | Yes |
| NM_001920 | DCN | No | Yes | Yes | Yes | Yes |
| NM_015881 | DKK3 | No | No | No | Yes | Yes |
| NM_000610.3 | EDN1 | Yes | Yes | Yes | Yes | Yes |
| NM_000115.3 | EDNRB | No | Yes | Yes | Yes | No |
| NM_001962 | EFNA5 | No | No | Yes | Yes | No |
| NM_006209.4 | ENPP2 | No | No | Yes | Yes | Yes |
| NM_000504 | F10 | Yes | Yes | Yes | Yes | Yes |
| NM_001993.4 | F3 | Yes | No | No | Yes | Yes |
| NM_014888 | FAM3C | No | No | Yes | No | Yes |
| NR_033766 | FOXP2 | Yes | ND | ND | ND | No |
| NM_002037 | FYN | No | ND | ND | ND | No |
| NM_013417 | IARS | No | ND | ND | ND | No |
| NM_178822 | IGSF10 | Yes | Yes | Yes | Yes | Yes |
| NM_002184 | IL6ST | No | No | No | Yes | Yes |
| NM_057159 | LPAR1 | No | ND | ND | ND | No |
| NM_032951.2 | MLXIPL | No | ND | ND | ND | No |
| NM_001144966 | NEDD4L | No | No | No | Yes | No |
| NM_181741 | ORC4 | No | ND | ND | ND | No |
| NM_001191059 | PDE1C | No | ND | ND | Yes | ND |
| NM_003713 | PPAP2B | No | ND | ND | ND | No |
| NM_002764 | PRPS1 | No | ND | ND | ND | ND |
| NM_002912 | REV3L | No | No | No | Yes | No |
| NM_032784 | RSPO3 | Yes | No | No | Yes | Yes |
| NM_152753 | SCUBE3 | Yes | ND | ND | ND | Yes |
| NM_005410.2 | SEPP1 | No | No | No | Yes | Yes |
| NM_006216 | SERPINE2 | No | No | No | Yes | Yes |

TABLE 10-continued

List of genes upregulated or downregulated in C9ORF72 fibroblasts compared to control fibroblasts and effect of ASO treatment

| Accession # | Gene Symbol | Aberrant Fibroblast Expression Control) | Aberrant Human Motor Cortex Expression (±25% Change vs. vs. Control) | Aberrant Human Cerebellum Expression (±25% Change vs. Control) | Rescued with ASO Treatment (±25% Change vs. Control ASO) | Secreted |
|---|---|---|---|---|---|---|
| NM_178123 | SESTD1 | Yes | ND | ND | ND | |
| NM_006108 | SPON1 | Yes | Yes | Yes | Yes | |
| NR_027449 | TBC1D15 | No | ND | ND | ND | No |
| NM_003243 | TGFBR3 | No | No | Yes | No | |
| NM_003810 | TNFSF10 | Yes | No | Yes | Yes | |
| NM_006573 | TNFSF13B | Yes | Yes | Yes | Yes | |
| NM_001164496 | WDR52 | No | ND | ND | ND | |
| NM_007038 | ADAMTS5 | Yes | ND | ND | ND | Yes |

The effect of treatment with another gapmer ASO, ASO #1, was assessed in C9ORF72 fibroblasts. C9ORF72 fibroblasts were plated at 20,000 cells/well and transfected using Cytofectin reagent with 100 nM of ASO #1. After an incubation period of 3 days, mRNA levels of C9ORF72, as well as some of the above mentioned potential biomarker genes were measured by RT-qPCR. The data is presented in FIG. 3. The results indicate that treatment with ASO #1 significantly reduced C9ORF72 mRNA levels. Furthermore, there was normalization of the altered gene expression of all the tested genes, complement component C3, endothelin receptor 2 (EDNRB2), and endothelin. Endothelin has been previously implicated in ALS-FTD (Lederer, C. W. et al., BMC Genomics 2007. 8: 26; Rabin, S. J., et al., Hum. Mol. Genet. 2010. 19:313-28). The expression of the housekeeping gene, GAPDH, is shown as a loading control. The data strongly suggest that knocking down C9ORF72 mRNA may be successful in normalization of aberrant gene expression events induced by the C9ORF72 repeat expansion.

Example 3: Effect of Antisense Inhibition of Human C9ORF72 on Nuclear Retention of RNA-Binding Proteins in ALS/FTD Patient Fibroblast The effect of C9ORF72 mutation on the binding of RNA-binding proteins to the repeat expansion, a proteome array analysis, was examined. The effect of treatment with ISIS 576816 targeting C9ORF72 on this binding was also investigated.

C9ORF72 fibroblasts were analyzed by proteome array analysis (method adapted from Hu, S. et al., Cell. 2009. 139: 610-22). The results of the analysis revealed significant interactions between numerous RNA- and DNA-binding proteins, as presented in Table 11 Immunostaining with an ADARB2 antibody using the protocol described in Donnelly et al (Donnelly, C. J. et al., EMBO J. 2011. 30: 4665-4677) of one of the candidate proteins, ADARB2, in human C9ORF72 fibroblasts revealed increased nuclear retention of the protein when compared with healthy control fibroblasts. There was a ~40% increase in nuclear retention in C9ORF72 fibroblasts compared to the control (FIG. 4A). This data suggest that RNA-binding proteins and splicing proteins have a high affinity to the hexanucleotide repeat expansion in C9ORF72 patient cells.

Figure 4B:
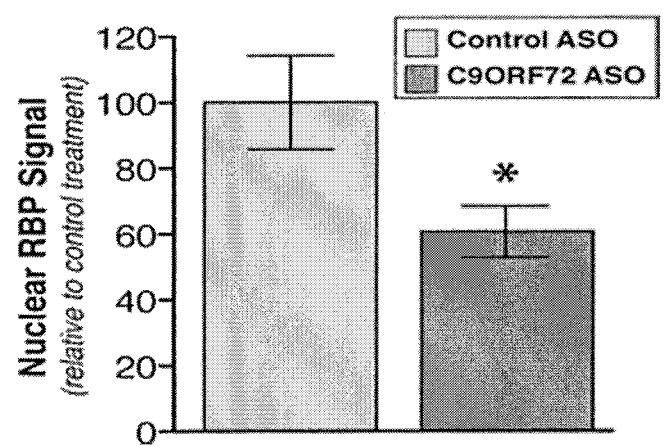
FIG. 4b is a graph showing nuclear retention of ADARB2 in human C9ORF72 fibroblasts after ASO treatment.
Figure 5:
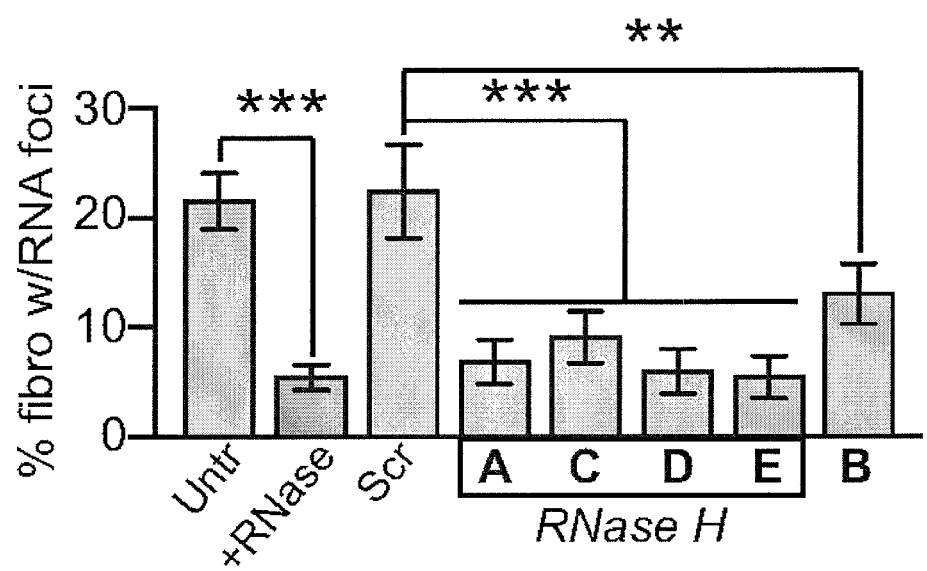
FIG. 5 is a graph showing reduction of foci in ASO treated cells relative to control.
Figure 6:
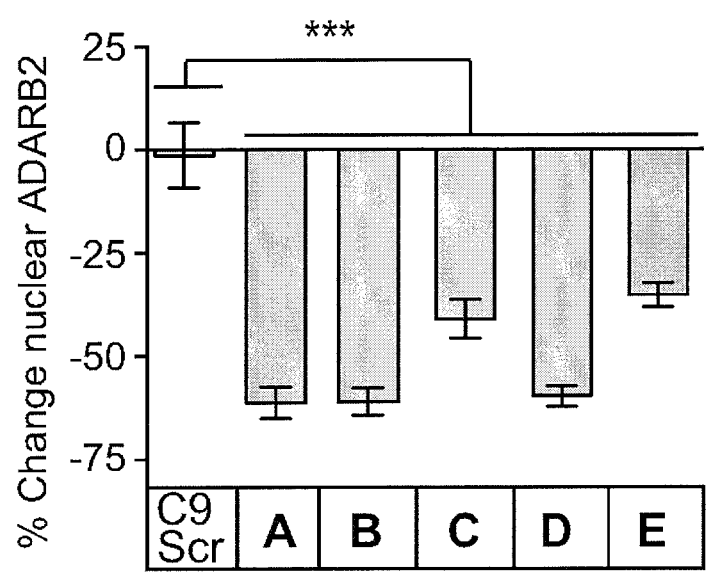
FIG. 6 is a graph showing percent change in nuclear ADARB2 in ASO treated cells relative to control.

To test whether treatment with ISIS 576816 targeting C9ORF72 would rescue human fibroblasts from this phenotype, C9ORF72 fibroblasts were plated at 20,000 cells/well and transfected using Cytofectin (Isis) reagent with 100 nM of ISIS 576816. The cells were then stained for ADARB2. The results are presented in FIG. 4B. The data indicates that antisense inhibition of C9ORF72 mRNA reduced the nuclear staining of ADARB2 back to levels observed in control healthy fibroblasts.

TABLE 11

List of genes of RNA- and DNA-binding proteins from proteome array analysis of C9ORF72 fibroblasts

| Symbol | Name | Accession # |
|---|---|---|
| NDST1 | [Heparan sulfate]-glucosamine N-sulfotransferase 1 | NM_001543.4 |
| MITF | Microphthalmia-associated transcription factor | NM_198159.2 |
| DPH2 | Diphthamide biosynthesis protein 2 | NM_001039589.1 |
| NUDT6 | Nudix (nucleoside diphosphate linked moiety X) - type motif 6 | NM_007083.4 |
| TCL1B | T-Cell leukemia/lymphoma protein 1B | NM_004918.3 |
| PGA5 | Pepsinogen 5 Group1 (pepsinogen A) | XM_002821692.2 |
| TRIM32 | tripartite motif-containing protein 32/E3 ubiquitin-protein ligase | NM_001099679.1 |
| CYP2C9 | Cytochrome P450, family 2, subtype family C, polypeptide 9/(S)-limonene 7-monooxygenase | NM_000771.3 |
| MPP7 | Membrane protein, palmitoylated 7/MAGUK p55 subfamily member | NM_173496.3 |
| PTER | Phosphotriesterase related protein | NM_001001484.1 |
| WBP11 | WW domain binding protein 11/Nwp-38 | NM_016312.2 |
| HMGB2 | High mobility group box 2 | NM_001130688.1 |
| ORAOV1 | Oral cancer overexpressed 1 | NM_153451.2 |
| RANGAP1 | Ran GTPase-activating protiein 1 | NM_002883.2 |
| ZNF695 | Zinc finger protein 695 | NM_001204221.1 |
| SOX6 | SRY (sex determining region Y)-box 6 | NM_001145811.1 |

TABLE 11-continued

List of genes of RNA- and DNA-binding proteins from proteome array analysis of C9ORF72 fibroblasts

| Symbol | Name | Accession # |
|---|---|---|
| JARID2 | Jumonji | NM_004973.2 |
| ADARB2 | adenosine deaminase RNA-specific, B2 | NM_018702.3 |

Example 4: In Vivo Rodent Inhibition and Tolerability with Treatment of C9ORF72 Antisense Oligonucleotides In order to assess the tolerability of inhibition of C9ORF72 expression in vivo, antisense oligonucleotides targeting a murine C9ORF72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 11 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A; wherein 's' denotes a phosphorothioate internucleoside linkage, 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 12 (GENBANK Accession No. NM_001007702.1).

Mouse Experiment 1

Groups of 4 C57BL/6 mice each were injected with 50 µg, 100 µg, 300 µg, 500 µg, or 700 µg of ISIS 571883 administered via an intracerebroventricular bolus injection. A control group of four C57/BL6 mice were similarly treated with PBS. Animals were anesthetized with 3% isofluorane and placed in a stereotactic frame. After sterilizing the surgical site, each mouse was injected −0.2 mm anterioposterior from the bregma na d 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9ORF72 mRNA expression. C9ORF72 mRNA expression was measured by RT-PCR. The data is presented in Table 12. The results indicate that treatment with increasing doses of ISIS 571883 resulted in dose-dependent inhibition of C9ORF72 mRNA expression.

The induction of the microglial marker AIF-1 as a measure of CNS toxicity was also assessed. The data is presented in Table 13. The results indicate that treatment with increasing doses of ISIS 571883 did not result in significant increases in AIF-1 mRNA expression. Hence, the injection of ISIS 571883 was deemed tolerable in this model.

TABLE 12

Percentage inhibition of C9ORF72 mRNA expression compared to the PBS control

| Dose (µg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 13

Percentage expression of AIF-1 mRNA expression compared to the PBS control

| Dose (µg) | Posterior brain | Spinal cord |
|---|---|---|
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 µg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 14 and 15. The results indicate that there were no significant changes in the motor behavior of the mice as a result of antisense inhibition of ISIS 571883 or due to the ICV injection. Hence, antisense inhibition of C9ORF72 was deemed tolerable in this model.

TABLE 14

Latency to fall (sec) in the rotarod assay

| Weeks after injection | PBS | ISIS 571883 |
|---|---|---|
| 0 | 66 | 66 |
| 4 | 91 | 70 |
| 8 | 94 | 84 |

TABLE 15

Mean hindlimb grip strength (g) in the grip strength assay

| Weeks after injection | PBS | ISIS 571883 |
|---|---|---|
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 µg, 1,000 µg, or 3,000 µg of ISIS 603538 administered via an intrathecal bolus injection. A control group of four Sprague-Dawley rats were similarly treated with PBS. Animals were anesthetized with 3% isofluorane and placed in a stereotactic frame. After sterilizing the surgical site, each rat was injected with 30 µL of ASO solution administered via 8 cm intrathecal catheter 2 cm into the spinal canal with a 50 µL flush. The rats were allowed to recover for 4 weeks, after which animals were euthanized according to a humane protocol approved by the Institutional Animal Care and Use Committee.

RNA Analysis

RNA was extracted from 2-3 mm brain section posterior to the injection site, from brain frontal cortex and from the cervical and lumbar sections of the spinal cord tissue for analysis of C9ORF72 mRNA expression. C9ORF72 mRNA expression was measured by RT-PCR. The data is presented in Table 16. The results indicate that treatment with increasing doses of ISIS 603538 resulted in dose-dependent inhibition of C9ORF72 mRNA expression.

The induction of the microglial marker AIF-1 as a measure of CNS toxicity was also assessed. The data is presented in Table 17. The results indicate that treatment with increasing doses of ISIS 603538 did not result in significant increases in AIF-1 mRNA expression. Hence, the injection of ISIS 603538 was deemed tolerable in this model.

TABLE 16

Percentage inhibition of C9ORF72 mRNA expression compared to the PBS control

| Dose (µg) | Brain (1 mm section) | Cortex | Spinal cord (lumbar) | Spinal cord (cervical) |
|---|---|---|---|---|
| 700 | 21 | 4 | 86 | 74 |
| 1000 | 53 | 49 | 88 | 82 |
| 3000 | 64 | 62 | 88 | 80 |

TABLE 17

Percentage expression of AIF-1 mRNA expression compared to the PBS control

| Dose (µg) | Brain (1 mm section) | Cortex | Spinal cord (lumbar) | Spinal cord (cervical) |
|---|---|---|---|---|
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 18. The results indicate that treatment with increasing doses of ISIS 603538 did not have any significant changes in the body weights of the rats.

TABLE 18

Body weights of the rats (% initial body weight)

| | Dose (µg) | Week 1 | Week 2 | Week 3 | Week 4 | Week 5 |
|---|---|---|---|---|---|---|
| PBS | | 100 | 94 | 103 | 105 | 109 |
| ISIS 603538 | 700 | 100 | 94 | 98 | 103 | 107 |
| | 1000 | 100 | 95 | 97 | 101 | 103 |
| | 3000 | 100 | 92 | 98 | 102 | 105 |

Example 5: RNA Binding Protein ADARB2 Interacts with GGGGCC RNA

A proteome array was utilized to identify protein-binding partners for the GGGGCC hexanucleotide repeat expansion. A 5'Cy5-labeled $GGGGCC_{x6.5}$ RNA was synthesized and hybridized to a proteome array containing nearly two-thirds of the annotated human proteome as yeast-expressed, full-length ORFs with N-terminal GST-His$_6$ fusion proteins (a total of 16,368 full length human proteins repeated 2-3 time per chip). See, JEONG et al., "Rapid Identification of Monospecific Monoclonal Antibodies Using a Human Proteome Microarray." Mol. Cell. Proteomics (2012) 11(6): O111.016253-1 to O111.016253-10. A 5'Cy5-labeled scrambled RNA of the same G:C content as the 5'Cy5-labeled $GGGGCC_{x6.5}$ RNA was used as a negative control. For each RNA sequence, 3 proteome arrays were hybridized in parallel as technical replicates. Using this method, 19 ORFs were identified (see Table 19) that consistently exhibited high affinity for the $GGGGCC_{x6.5}$ RNA as compared to the scrambled RNA determined via the AZ-score [$GGGGCC_{x6.5}$ RNA Z-score —G:C scrambled RNA Z-score]. Among this list, ADARB2 was studied further.

TABLE 19

Proteins that Interact with GGGGCC RNA sequence using proteome array.

| Symbol | Name | Accession # | Loci | Z-GC Scrambled | Z-GGGGCC | ΔZ |
|---|---|---|---|---|---|---|
| NDST1 | [Heparan sulfate]-glucosamine N-sulfotransferase 1 | NM_001543.4 | 5q33.1 | 8.06 | 37.08 | 29.03 |
| MITF | Microphthalmia-associated transcription factor | NM_198159 | 3p14.2-p14.1 | 6.71 | 22.49 | 15.78 |
| DPH2 | Diphthamide biosynthesis protein 2 | NM_001039589.1 | 1p34 | 3.43 | 14.04 | 10.61 |
| NUDT6 | Nudix (nucleoside diphosphate linked moiety X) - type motif 6 | NM_007083.4 | 4q26 | 8.38 | 16.66 | 8.28 |
| TCL1B | T-Cell leukemia/lyphoma protein 1B | NM_004918 | 14q32.1 | 5.42 | 12.91 | 7.49 |
| PGA5 | PGA5 pepsinogen 5, group I | NM_014224.2 | 11q13 | 2.96 | 8.93 | 5.97 |
| TRIM32 | Tripartite motif-containing protein 32/E3 ubiquitin-protein ligase | NM_001099679.1 | 9p33.1 | 4.63 | 10.25 | 5.62 |
| CYP2C9 | Cytochrome P450, family 2, subtype family C, polypeptide 9/(S)-limonene 7-monooxygenase | NM_000771.3 | 10q24 | 1.49 | 5.83 | 4.34 |
| MPP7 | Membrane protein, palmitoylated 7/MAGUK p55 subfamily member | NM_173496.3 | 10p21.1 | 0.30 | 4.43 | 4.13 |
| PTER | Phosphotriesterase related protein | NM_001001484.1 | 10p12 | 4.09 | 7.45 | 3.36 |
| WBP11 | WW domain binding protein 11/Nwp-38 | NM_016312.2 | 12p12.3 | −0.17 | 2.84 | 3.02 |
| HMGB2 | High mobility group box 2 | NM_001130688.1 | 4q31 | 1.23 | 4.35 | 3.12 |
| ORAOV1 | Oral cancer overexpressed 1 | NM_153451.2 | 11q13.3 | 0.41 | 3.23 | 2.83 |
| RANGAP1 | Ran GTPase-activating protiein 1 | NM_002883.2 | 22q13 | 1.21 | 3.38 | 2.17 |
| ZNF695 | Zinc finger protein 695 | NM_001204221.1 | 1q44 | 2.18 | 4.76 | 2.58 |
| SOX6 | SRY (sex determining region Y)-box 6 | NM_001145811.1 | 11p15.3 | 1.16 | 3.68 | 2.51 |
| JARID2 | Jumonji | NM_004973.2 | 6p24-p23 | 0.64 | 3.01 | 2.37 |
| ADARB2 | Adenosine deaminase RNA-specific, B2 | NM_018702.3 | 10p15.3 | −0.20 | 2.09 | 2.29 |
| DAZ2 | Deleted in azoospermia 2 | NM_001005785.2 | Yq11.223 | 7.80 | 13.12 | 5.33 |

Z scores are generated by hybridizing a Cy5-labelled GC-scrambled or GGGGCC×6.5 RNA to a proteome array and quantifying the average signal intensity of a single spot on the proteome array that corresponds to a full length ORF (n=3 arrays). High signal intensity indicates a strong binding between the ORF and the labeled RNA. (ΔZ=Z-GGGGCC-Z-GC Scrambled). A positive ΔZ indicates specific affinity for the GGGGCC RNA as compared to the scrambled RNA of the same GC content.

Simultaneous RNA FISH and RBP immunofluorescence (RNA FISH-IF) studies in C9ORF72 iPSNs revealed that ADARB2 protein colocalizes with the nuclear GGGGCC RNA foci, with unchanged levels of mRNA. In addition, RBP:RNA coimmunoprecipitation (RNA co-IP) studies were used to isolate C9ORF72 RNA from the RNA co-IP using primers to exon 1a and the intronic region 5' of the GGGGCC expanded repeat indicating that ADARB2 interacts with endogenous C9ORF72 RNA in living cells. Finally, an electrophoretic gel shift assay (EMSA) was performed with recombinant ADARB2 purified from E. coli. Titrating ADARB2 shows depletion of free RNA and shift to slower mobility or a well shift, the latter of which is presumably due to multimerization of the protein—RNA complexes. Taken together, these data indicate that both biochemically and in living cells, ADARB2 protein interacts with C9ORF72 RNA and has a high binding affinity for the GGGGCC repeat RNA sequence, which could be useful as a readout to monitor C9ORF72-specific drug efficacy.

To determine if these in vitro observations are recapitulated in vivo, the colocalization of ADARB2 protein to GGGGCC RNA foci in human postmortem C9ORF72 patient tissue was examined. RNA FISH-IF confirmed that ADARB2 colocalizes with GGGGCC RNA foci in motor cortex of C9ORF72 ALS patients, while there is no nuclear accumulation or colocalization in non-C9 ALS tissue.

ADARB2 interacts with endogenous C9ORF72 RNA through the GGGGCC repeat sequence. To determine if ADARB2 is required for RNA foci formation, iPSNs were treated with siRNA against ADARB2 and performed RNA FISH for the nuclear GGGGCC RNA foci. siRNA-mediated knockdown of ADARB2 resulted in a statistically significant 48.99% reduction in the number of iPSNs with RNA foci. These studies suggest that an interaction between ADARB2 and the C9ORF72 RNA expansion plays a role in the formation or maintenance of the RNA foci in vitro supporting the hypothesis that interactions of RBPs with the GGGGCC repeat may play a role in C9ORF72$_{exp}$-RNA toxicity. Moreover, ADARB2 statistically accumulates in the nucleus of C9ORF72 iPSN by immunostaining and this was recapitulated in C9ORF72 ALS post-mortem tissue.

Example 6: Identification of Pharmacodynamic Biomarkers to Monitor C9ORF72 Therapy in Human CSF and/or Blood Sequestration of RBPs and the presence of nuclear foci suggest that the hexanucleotide repeat expansion may alter the cellular transcriptome which provide a readout for therapeutic intervention. Using five C9ORF72 ALS fibroblast lines, unique gene expressions changes (p<0.05) were identified as compared to healthy controls, and accounted for significantly altered genes from SOD1$^{mut}$ fibroblasts. Using 4 iPSN lines, a unique population of genes were identified that were dysregulated as compared to control, subtracting the aberrantly expressing genes from SOD$^{D90A}$ iPSN lines. iPSNs that carry a SOD1$^{D90A}$ mutation exhibited a large number of dysregulated genes when compared to control cells, although a subset of expression abnormalities were common between C9ORF72 and SOD1$^{D90A}$ iPSNs. Taken together, these data indicate that the C9ORF72 transcriptome is different from the SOD1$^{mut}$ transcriptome in both fibroblasts and iPSNs. This can be visualized when comparing the expression levels of statistically significant genes in C9ORF72 iPSNs to that of SOD1$^{D90A}$ iPSNs.

Commonalities between C9ORF72 iPS-derived neurons and post-mortem motor cortex (n=3) were examined to evaluate if cultured iPSNs recapitulate the C9ORF72 ALS human brain transcriptome and can, therefore, be used to evaluate future therapeutics. A large number of aberrantly expressed genes (p<0.05) were identified in C9ORF72 ALS motor cortex (compared to control) of which a subset overlapped with genes aberrantly expressed in C9ORF72 iPSNs, including those expressed concordantly. When comparing C9ORF72 fibroblasts to C9ORF72 iPSN and motor cortex, fewer genes were found to be common suggesting that these cell types are not very similar. Only a population of altered genes is shared between the postmortem C9ORF72 human motor cortex and the C9ORF72 iPSNs, most likely due to the cellular heterogeneity of the human motor cortex as compared to a neuron-enriched iPSN culture system. All C9ORF72 cell and tissue gene arrays consistently showed a larger number of downregulated genes than upregulated genes, which was not observed in the SOD1$^{mut}$ samples.

With the goal of identifying genes that might be utilized as therapeutic biomarkers, genes that exhibited altered expression in C9ORF72 iPSNs, fibroblasts, or human motor cortex via exon microarray were selected. Also selected, were genes coding for proteins that are expressed in the CNS and, the majority of which, are secreted as this would allow for quantification of the protein levels in patient cerebrospinal fluid (CSF). Twenty-six target genes were selected and tested their expression in C9ORF72 autopsied CNS tissue against non-ALS control tissue using nanostring gene expression methodologies. Sixteen of the target genes tested were also aberrantly expressed in C9ORF72 ALS patient tissue, of which 7 showed the same direction of dysregulation (up or down) when compared to iPSNs: EDN1, NEDD4L, FAM3C, CHRDL1, CP, SEPP1, and SERPINE2. These genes 7 genes can be used as pharmacodynamic biomarkers to monitor C9ORF72 therapy in human CSF and/or blood.

Example 7: Antisense Oligonucleotides Reduce Nuclear ADARB2 Protein Signals in C9ORF72 iPSNs and Normalize C9ORF72 Gene Expression Pattern Antisense oligonucleotides were designed targeting various regions of the C9ORF72 gene (the complement of GENBANK Accession No. NT_008413.18 truncated from nucleotides 27535000 to 27565000, designated herein as SEQ ID NO: 2). The antisense oligonucleotides are either 2'-O-methyl modified oligonucleotides (denoted "2'OMe") or 2'-MOE antisense oligonucleotides (denoted "2'MOE"). The oligonucleotides are either 5-10-5 MOE gapmers, 5-10-5 2'O-methyl gapmers, or full MOE oligonucleotides. The 5-10-5 MOE gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The 5-10-5 2'OMe gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a 2'OMe modification. The full MOE oligonucleotide is 20 nucleotides in length, wherein each nucleoside has a MOE modification. The internucleoside linkages throughout each oligonucleotide are phosphorothioate linkages (denoted "PT backbone"). All cytosine residues throughout each MOE gapmer are 5-methylcytosines. The target start site, target region, and function (RNase H or blocking) of each antisense oligonucleotide are specified in Table 20 below. The blocking ASO binds the GGGGCC$_{exp}$ RNA repeat to block any RBP interaction but does not degrade the transcript. Each antisense oligonucleotide listed in Table 7 is targeted to the SEQ ID NO: 2.

TABLE 20

Antisense oligonucleotides targeting SEQ ID NO: 2

| Sequence | Oligo ID # | ISIS NO | Target Start Site | Target Stop Site | Chemical Modifications | Function | SEQ ID NO |
|---|---|---|---|---|---|---|---|
| GCCCCGGCCCCTAGCGCGCG | A | N/A | 1448 | 1467 | 5-10-5 2'OMe PT backbone | RNase H | 22 |
| CCGGCCCCGGCCCCGGCCCC | B | 573674 | 1457 | 1476 | Full MOE PT backbone | Block | 31 |
| CCGGCCCCGGCCCCGGCCCC | C | 573716 | 1457 | 1476 | 5-10-5 2'MOE PT backbone | RNase H | 31 |
| GGTAACTTCAAACTCTTGGG | D | 577083 | 3452 | 3471 | 5-10-5 2'MOE PT backbone | RNase H | 29 |
| GCCTTACTCTAGGACCAAGA | E | 576816 | 7990 | 8009 | 5-10-5 2'MOE PT backbone | RNase H | 28 |

Figure 7:
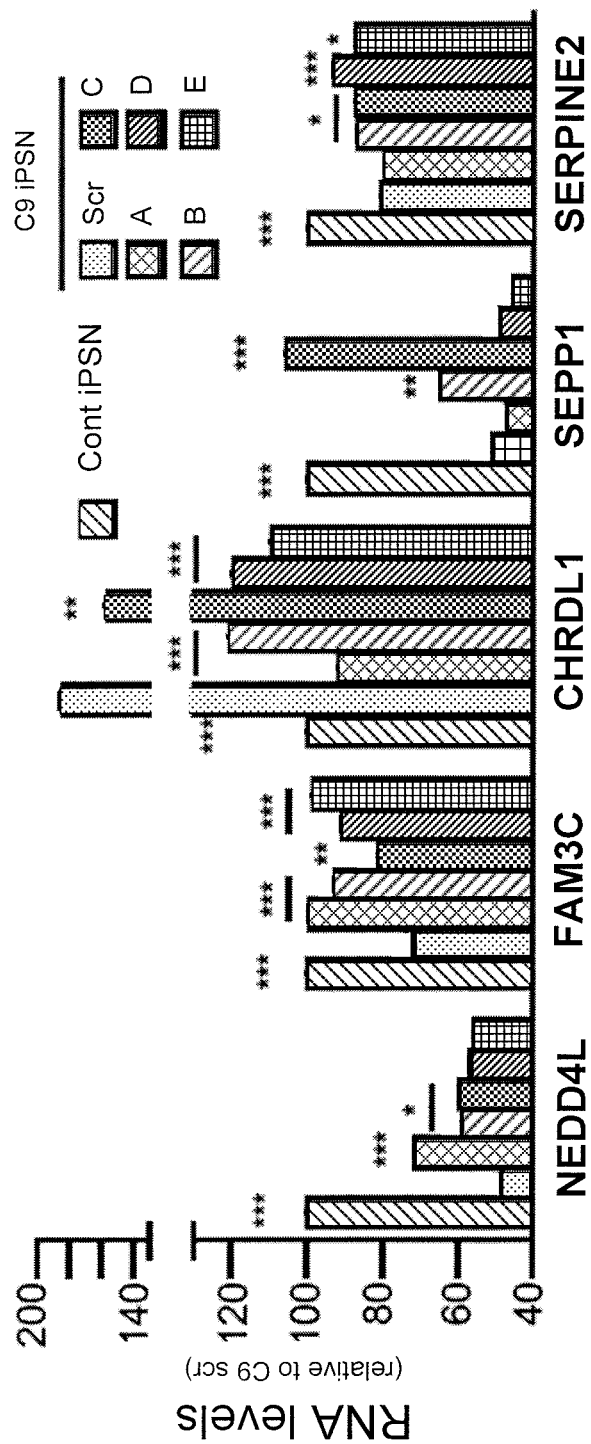
FIG. 7 is a graph showing RNA levels of NEDD4L, FAM3C, CHRDL1, SEPP1, and SERPINE2 after ASO treatment relative to control.
Figure 8:
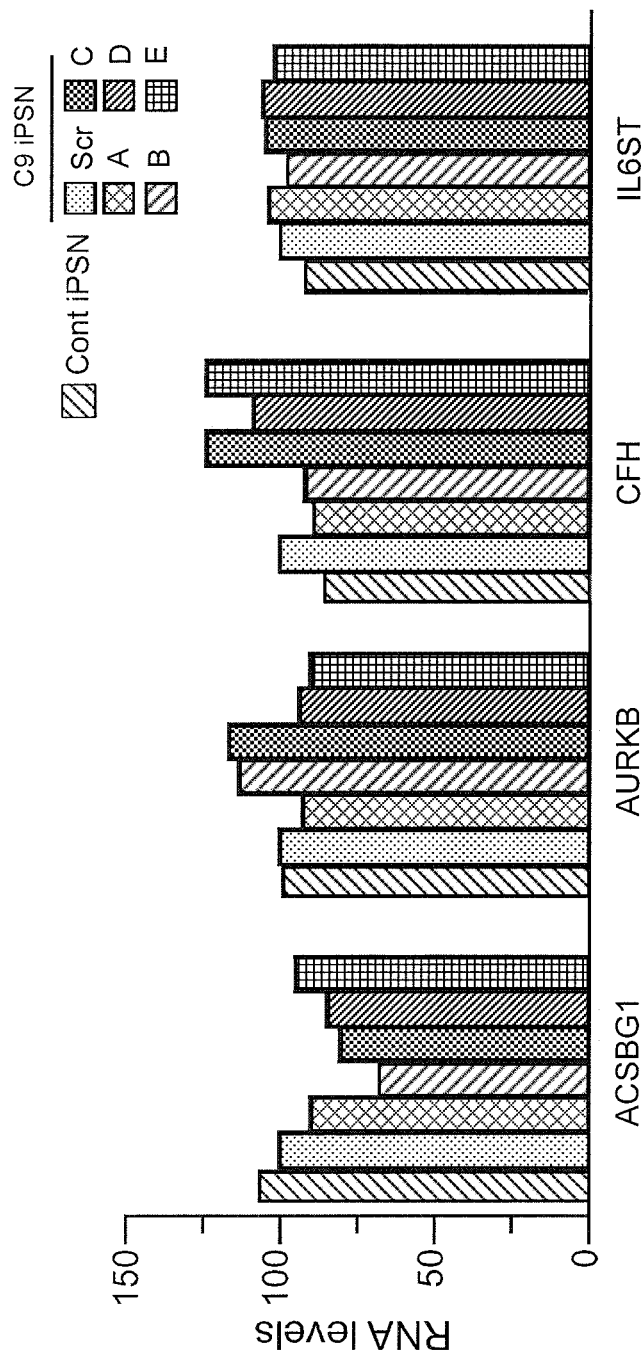
FIG. 8 is a graph showing RNA levels of ACSBG1, AURKB, CRH, and IL6ST after ASO treatment relative to control.

RNase H-mediated antisense oligonucleotides significantly reduced both the percentage of cells that contain GGGGCC$_{exp}$ RNA foci and the number of foci per cell in both fibroblasts and iPSN cultures regardless of the ASO target location or effect on C9ORF72 RNA levels (FIG. 7). In an ADARB2:RNA foci colocalization study, ASOs A, B, C, D, and E reduced the nuclear ADARB2 protein signals in C9ORF72 iPSNs as determined by immunostaining (FIG. 8), suggesting that ADARB2 colocalization with RNA foci is due to protein:GGGGCC$_{exp}$ RNA interaction.

ASO treatment also normalized the dysregulated gene expression of our candidate biomarker genes NEDD4L, FAM3C, CHRDL1, SEPP1, and SERPINE2 in C9ORF72 iPSNs (FIG. 9) independent of the ASO target region. These genes can serve as biomarkers to monitor ASO therapy efficacy. Genes that were not altered between control and C9ORF72 iPSNs did not change when treated with ASOs, suggesting that ASO treatment does not have untoward effects on general gene transcription (FIG. 10).

What is claimed is:

1. A method comprising contacting a cell of a patient with a neurodegenerative disease with a compound comprising an oligonucleotide consisting of 12 to 30 linked nucleosides, wherein the oligonucleotide is at least 90% complementary to a C9ORF72 nucleic acid, wherein the compound reduces nuclear retention of any of ADARB2, CYP2C9, DPH2, HMGB2, JARID2, MITF, MPP7, NDST1, NUDT6, ORAOV1, PGA5, PTER, RANGAP1, SOX6, TCL1B, TRIM32, WBP11, or ZNF695 in the cell.

2. The method of claim 1, wherein the cell is in vivo.

3. The method of claim 1, wherein the C9ORF72 nucleic acid has the nucleobase sequence of any of SEQ ID Nos: 1-10.

4. The method of claim 3, wherein the oligonucleotide is a modified oligonucleotide.

5. The method of claim 4, wherein the modified oligonucleotide is a single-stranded oligonucleotide.

6. The method of claim 5, wherein the single-stranded modified oligonucleotide is a gapmer.

7. The method of claim 6, wherein at least one internucleoside linkage of the modified oligonucleotide is a modified internucleoside linkage.

8. The method of claim 7, wherein the modified internucleoside linkage is a phosphorothioate internucleoside linkage.

9. The method of claim 5, wherein at least one nucleobase of the modified oligonucleotide is a modified nucleobase.

10. The method of claim 9, wherein the modified nucleobase is a 5-methylcytosine.

11. The method of claim 5, wherein at least one nucleoside of the modified oligonucleotide comprises a modified sugar.

12. The method of claim 11, wherein the modified sugar is a bicyclic sugar.

13. The method of claim 12, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently H, C$_1$-C$_6$ alkyl, and C$_1$-C$_6$ alkoxy.

14. The method of claim 13, wherein the chemical bridge is 4'-CH(R)—O-2' and wherein R is methyl.

15. The method of claim 13, wherein the chemical bridge is 4'-CH(R)—O-2' and wherein R is H.

16. The method of claim 13, wherein the chemical bridge is 4'-CH(R)—O-2' and wherein R is CH$_2$—O—CH$_3$.

17. The method of claim 11, wherein the modified sugar comprises a 2'-O-methoxyethyl group.

18. The method of claim 1, wherein the neurodegenerative disease is selected from amyotrophic lateral sclerosis (ALS), frontotemporal dementia (FTD), corticalbasal degeneration syndrome (CBD), atypical Parkinsonian syndrome, and olivopontocerellar degeneration (OPCD).

19. The method of claim 18, wherein the cell is in vitro.

* * * * *